United States Patent [19]

Kuno et al.

[11] Patent Number: 5,968,985

[45] Date of Patent: Oct. 19, 1999

[54] BENZOYLGUANIDINE DERIVATIVES AS MEDICAMENTS

[75] Inventors: Atsushi Kuno; Hiroaki Mizuno, both of Osaka; Kumi Yamasaki, Nishinomiya; Yoshikazu Inoue, Osaka, all of Japan

[73] Assignee: Fujisawa Pharmaceutical Co., Ltd., Osaka, Japan

[21] Appl. No.: 08/776,385

[22] PCT Filed: Jul. 25, 1995

[86] PCT No.: PCT/JP95/01479

§ 371 Date: Feb. 3, 1997

§ 102(e) Date: Feb. 3, 1997

[87] PCT Pub. No.: WO96/04241

PCT Pub. Date: Feb. 15, 1996

[30] Foreign Application Priority Data

Aug. 5, 1994 [GB] United Kingdom .................. 9415852
Nov. 11, 1994 [GB] United Kingdom .................. 9422830
Mar. 15, 1995 [GB] United Kingdom .................. 9505231

[51] Int. Cl.$^6$ .......................... A01N 37/18; C07C 233/00
[52] U.S. Cl. .......................... 514/617; 514/618; 564/180; 564/187
[58] Field of Search .................. 564/180, 187; 514/617, 618

[56] References Cited

FOREIGN PATENT DOCUMENTS 556673  2/1993  European Pat. Off. ............... 514/331
556674  2/1993  European Pat. Off. ............... 514/618

*Primary Examiner*—John Kight
*Assistant Examiner*—Raymond Covington
*Attorney, Agent, or Firm*—Oblon, Spivak, McClelland, Maier & Neustadt, P.C.

[57] ABSTRACT

A process for preparing a pharmaceutical composition which comprises admixing a compound of claim 1 or a pharmaceutically acceptable salt thereof with a pharmaceutically acceptable carrier.

12 Claims, No Drawings

BENZOYLGUANIDINE DERIVATIVES AS MEDICAMENTS

This application is a 371 of PCT/JP95/011479 filed Jul. 25, 1995.

TECHNICAL FIELD

This invention relates to new guanidine derivatives and a pharmaceutically acceptable salts thereof which are useful as a medicament.

DISCLOSURE OF INVENTION

This invention relates to new guanidine derivatives.

One object of this invention is to provide the new and useful guanidine derivatives and pharmaceutically acceptable salts thereof which possess a strong inhibitory activity on $Na^+/H^+$ exchange in cells.

Another object of this invention is to provide processes for preparation of the guanidine derivatives and salts thereof.

A further object of this invention is to provide a pharmaceutical composition comprising said guanidine derivatives or a pharmaceutically acceptable salt thereof.

Still further object of this invention is to provide a use of said guanidine derivatives or a pharmaceutically acceptable salt thereof as a medicament for the treatment and/or prevention of cardiovascular diseases, cerebrovascular diseases, renal diseases, arteriosclerosis, shock and the like in human being and animals.

The object guanidine derivatives of the present invention are novel and can be represented by the following general formula (I):

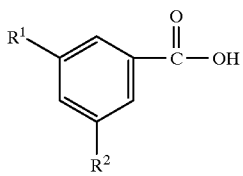

(I)

wherein $R^1$ is hydrogen, hydroxy(lower)alkyl, protected hydroxy(lower)alkyl, acyl(lower)alkoxy, acyl(lower)alkenyl, or acyl, and $R^2$ is ar(lower)alkenyl; aryl substituted with two suitable substituents; indenyl, indanyl, dihydrobenzocycloheptenyl, di(or tetra or hexa or octa or deca)hydronaphthyl, cyclopentenyl, dihydrothienyl, dihydrofuryl or heterobicyclic group, each of which may have suitable substituent(s); lower alkylthienyl; mono(or di)halothienyl; mono(or di or tri)halo(lower)alkylthienyl; acylthienyl; halofuryl; or mono(or di or tri)halo(lower)alkylfuryl.

The object compound (I) of the present invention can be prepared by the following process.

Process (1)

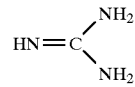

(II)

or its reactive derivative at the carboxy group, or a salt thereof

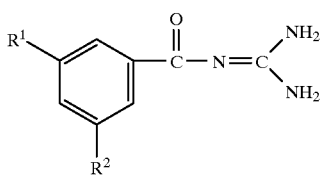

(III)

or its reactive derivative at the imino group, or a salt thereof (I)

or a salt thereof wherein $R^1$ and $R^2$ are each as defined above.

The starting compound can be prepared by the following processes or Preparations mentioned below, or similar manners thereto.

Process (A)

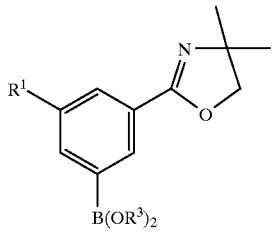

(IV)

or a salt thereof

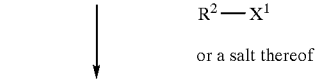

(V)

or a salt thereof

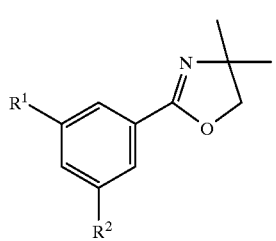

(VI)

or a salt thereof

Process (B)
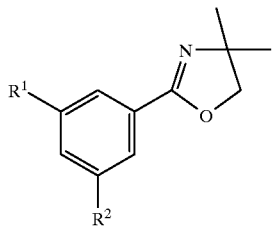
or a salt thereof
(VI)
↓ R⁴—OH
or a salt thereof
(VII)
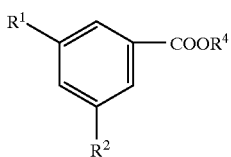
or a salt thereof
(IIa)
Process (C)
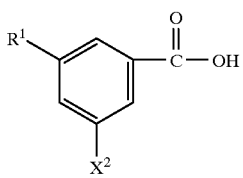
or a salt thereof
(VIII)
↓ R²—B(OR⁵)₂
or a salt thereof
(IX)
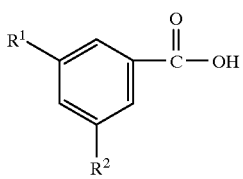
or a salt thereof
(II)
Process (D)
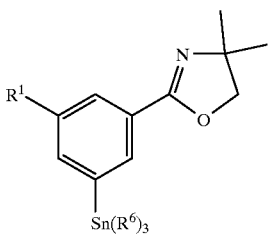
or a salt thereof
(X)
↓ R²—X¹
or a salt thereof
(V)
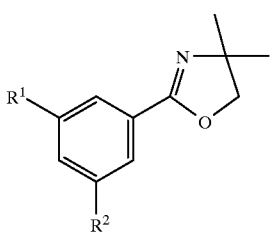
or a salt thereof
(VI)
Process (E)
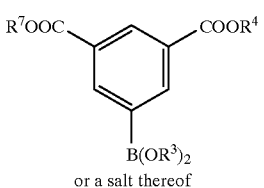
or a salt thereof
(XI)
↓ R²—X¹
or a salt thereof
(V)
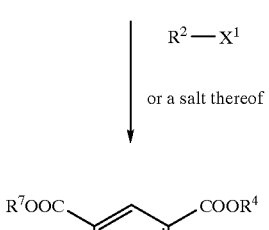
or a salt thereof
(XII)

Process (F)

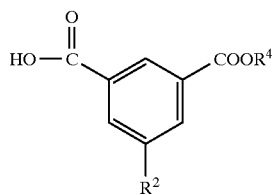

or its reactive derivative at the
carboxy group, or a salt thereof

↓ amidation

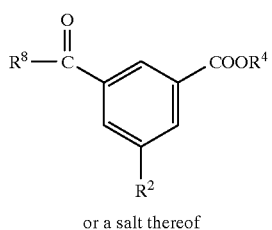

or a salt thereof

Process (G)

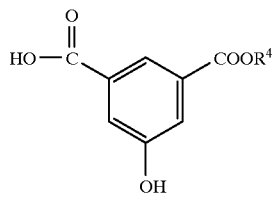

or its reactive derivative at the
carboxy group, or a salt thereof

①  ↓ amidation

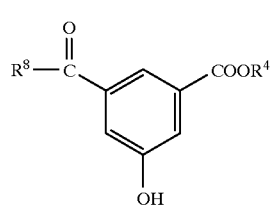

or a salt thereof

②  ↓ introduction of a leaving group (XIIa)

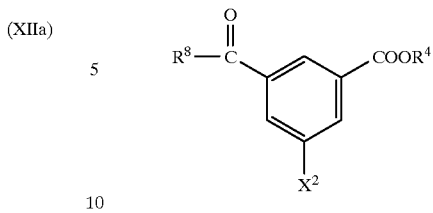
(VIIIa)

Process (H)

(IIb)

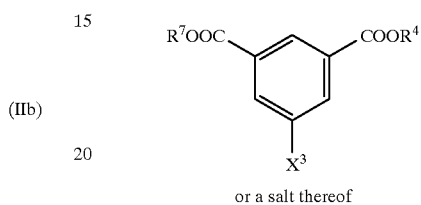
(XV)

↓ 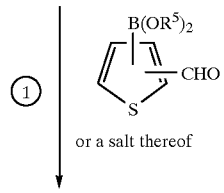 (XVI)

or a salt thereof (XIII)

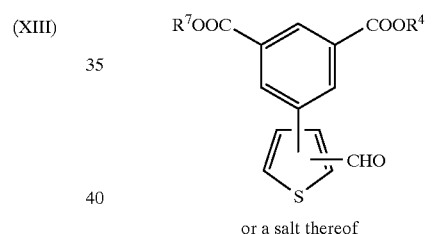
(XVII)

or a salt thereof

② ↓ halogenation (XIV)

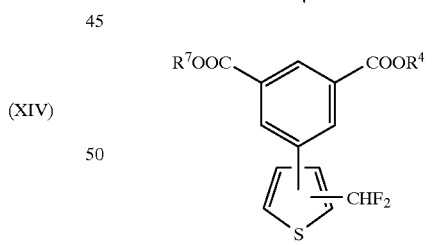
(XIIb)

wherein
$R^1$ and $R^2$ are each as defined above,
$R^3$, $R^4$, $R^5$ and $R^7$ are each hydrogen or lower alkyl,
$R^6$ is lower alkyl,
a group of the formula: —CO—$R^8$ is amidated carboxy, and
$X^1$, $X^2$ and $X^3$ are each a leaving group.

Suitable pharmaceutically acceptable salts of the object compound (I) are conventional non-toxic salts and may include a salt with a base or an acid addition salt such as a salt with an inorganic base, for example, an alkali metal salt (e.g., sodium salt, potassium salt, etc.), an alkaline earth metal salt (e.g., calcium salt, magnesium salt, etc.), an ammonium salt; a salt with an organic base, for example, an organic amine salt (e.g., triethylamine salt, pyridine salt, picoline salt, ethanolamine salt, triethanolamine salt, dicyclohexylamine salt, N,N'-dibenzylethylenediamine salt, etc.); an inorganic acid addition salt (e.g., hydrochloride, hydrobromide, sulfate, phosphate, etc.); an organic carboxylic or sulfonic acid addition salt (e.g., formate, acetate, trifluoroacetate, maleate, tartrate, isethionate, fumarate, methanesulfonate, benzenesulfonate, toluenesulfonate, etc.); a salt with a basic or acidic amino acid (e.g., arginine, aspartic acid, glutamic acid, etc.).

In the above and subsequent descriptions of the present specification, suitable examples and illustration of the various definitions which the present invention intends to include within the scope thereof are explained in detail as follows.

The term "lower" is used to intend a group having 1 to 6, preferably 1 to 4, carbon atom(s), unless otherwise provided.

The term "higher" is used to intend a group having 7 to 20 carbon atoms, unless otherwise provided.

Suitable "lower alkyl" and "lower alkyl moiety" in the terms "hydroxy(lower)alkyl", "protected hydroxy(lower) alkyl", "lower alkylthienyl", "mono(or di or tri)halo(lower) alkylthienyl" and "mono(or di or tri)halo(lower)alkylfuryl" may include straight or branched one having 1 to 6 carbon atom(s), such as methyl, ethyl, propyl, isopropyl, butyl, isobutyl, sec-butyl, tert-butyl, pentyl, tert-pentyl, hexyl, and the like, and in which more preferable example may be $C_1$–$C_4$ alkyl.

Suitable lower alkenyl" and "lower alkenyl moiety" in the terms "ar(lower)alkenyl" and "acyl(lower)alkenyl" may include vinyl, 1-(or 2-)propenyl, 1-(or 2- or 3-)butenyl, 1-(or 2- or 3- or 4-)pentenyl, 1-(or 2- or 3- or 4- or 5-)hexenyl, methylvinyl, ethylvinyl, 1-(or 2- or 3-)methyl-1-(or 2-)propenyl, 1-(or 2- or 3-)ethyl-1-(or 2-)-propenyl, 1-(or 2- or 3- or 4-)methyl-1-(or 2- or 3-)butenyl, and the like, in which more preferable example may be $C_2$–$C_4$ alkenyl.

Suitable "lower alkynyl" may include ethynyl, 1-propynyl, propargyl, 1-methylpropargyl, 1 or 2 or 3-butynyl, 1 or 2 or 3 or 4-pentynyl, 1 or 2 or 3 or 4 or 5-hexynyl, and the like.

Suitable "lower alkoxy" and "lower alkoxy moiety" in the term "acyl(lower)alkoxy" may include methoxy, ethoxy, propoxy, isopropoxy, butoxy, isobutoxy, t-butoxy, pentyloxy, t-pentyloxy, hexyloxy and the like.

Suitable "cyclo(lower)alkyl" may include cyclopentyl, cyclohexyl and the like.

Suitable "cyclo(lower)alkenyl" may include cyclohexenyl, cyclohexadienyl and the like.

Suitable "aryl" and "aryl moiety" in the term "ar(lower) alkenyl" may include phenyl, naphthyl and the like.

Suitable "halogen" and "halogen moiety" in the terms "mono(or di)halothienyl", "mono(or di or tri)halo(lower) alkylthienyl", "halofuryl" and "mono(or di or tri)halo (lower)alkylfuryl" may include fluorine, bromine, chlorine and iodine.

Suitable "leaving group" may include acid residue, lower alkoxy as exemplified above, and the like.

Suitable "acid residue" may include halogen as exemplified above, acyloxy and the like.

Suitable "protected carboxy" may include esterified carboxy and the like. And suitable example of said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, etc.); lower alkenyl ester (e.g., vinyl ester, allyl ester, etc.); lower alkynyl ester (e.g., ethynyl ester, propynyl ester, etc.); lower alkoxy(lower)alkyl ester (e.g., methoxymethyl ester, ethoxymethyl ester, isopropoxymethyl ester, 1-methoxyethyl ester, 1-ethoxyethyl ester, etc.); lower alkylthio(lower)alkyl ester (e.g., methylthiomethyl ester, ethylthiomethyl ester, ethylthioethyl ester, isopropoxythiomethyl ester, etc.); mono(or di or tri)halo(lower)alkyl ester (e.g., 2-iodoethyl ester, 2,2,2-trichloroethyl ester, etc.); lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 1-acetoxyethyl ester, 2-acetoxyethyl ester, 2-propionyloxyethyl ester, etc.); lower alkoxycarbonyloxy (lower)alkyl ester (e.g., methoxycarbonyloxymethyl ester, ethoxycarbonyloxymethyl ester, propoxycarbonyloxymethyl ester, 1-(or 2-)[methoxycarbonyloxy]ethyl ester, 1-(or 2-)[ethoxycarbonyloxy]ethyl ester, 1-(or 2-) [propoxycarbonyloxy]ethyl ester, 1-(or 2-) [isopropoxycarbonyloxy]ethyl ester, etc.); lower alkanesulfonyl(lower)alkyl ester (e.g., mesylmethyl ester, 2-mesylethyl ester, etc.); lower alkoxycarbonyloxy(lower) alkyl ester (e.g., methoxycarbonyloxymethyl ester, ethoxycarbonyloxymethyl ester, propoxycarbonyloxymethyl ester, t-butoxycarbonyloxymethyl ester, 1-(or 2-)methoxycarbonyloxyethyl ester, 1-(or 2-)ethoxycarbonyloxyethyl ester, 1-(or 2-)isopropoxycarbonyloxyethyl ester, etc.); phthalidylidene (lower)alkyl ester; (5-lower alkyl-2-oxo-1,3-dioxol-4-yl) (lower)alkyl ester [e.g., (5-methyl-2-oxo-1,3-dioxol-4-yl) methyl ester, (5-ethyl-2-oxo-1,3-dioxol-4-yl)methyl ester, (5-propyl-2-oxo-1,3-dioxol-4-yl)ethyl ester, etc.]; mono(or di or tri)aryl(lower)alkyl ester, for example, mono(or di or tri)phenyl(lower)alkyl ester which may have one or more suitable substituent(s) (e.g., benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.); aryl ester which may have one or more suitable substituent(s) such as substituted or unsubstituted phenyl ester (e.g., phenyl ester, tolyl ester, t-butylphenyl ester, xylyl ester, mesityl ester, cumenyl ester, 4-chlorophenyl ester, 4-methoxyphenyl ester, etc.); tri(lower)alkyl silyl ester; lower alkylthioester (e.g., methylthioester, ethylthioester, etc.) and the like.

Suitable "hydroxy protective group" in the terms "protected hydroxy" and "protected hydroxy(lower)alkyl" may include acyl, mono(or di or tri)phenyl(lower)alkyl which may have one or more suitable substituent(s) (e.g., benzyl, 4-methoxybenzyl, trityl, etc.), trisubstituted silyl [e.g., tri (lower)alkylsilyl (e.g., trimethylsilyl, t-butyldimethylsilyl, etc.), etc.], tetrahydropyranyl and the like.

Suitable "protected amino" may include acylamino or an amino group substituted by a conventional protective group such as mono (or di or tri)aryl(lower)alkyl, for example, mono(or di or tri)phenyl(lower)alkyl (e.g., benzyl, trityl, etc.) or the like.

Suitable "acyl" and "acyl moiety" in the terms "acylamino", "acyloxy", "acyl(lower)alkoxy" "acyl(lower) alkenyl" and "acylthienyl" may include carbamoyl, aliphatic acyl group and acyl group containing an aromatic ring, which is referred to as aromatic acyl, or heterocyclic ring, which is referred to as heterocyclic acyl.

Suitable example of said acyl may be illustrated as follows:

Carbamoyl; Thiocarbamoyl; Sulfamoyl; Aliphatic acyl such as lower or higher alkanoyl (e.g., formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.);

lower or higher alkoxycarbonyl (e.g., methoxycarbonyl, ethoxycarbonyl, t-butoxycarbonyl, t-pentyloxycarbonyl, heptyloxycarbonyl, etc.);

lower or higher alkylsulfonyl (e.g., methylsulfonyl, ethylsulfonyl, etc.);

lower or higher alkoxysulfonyl (e.g., methoxysulfonyl, ethoxysulfonyl, etc.); cyclo(lower)alkylcarbonyl (e.g., cyclopentylcarbonyl, cyclohexylcarbonyl, etc.); or the like;

Aromatic acyl such as aroyl (e.g., benzoyl, toluoyl, naphthoyl, etc.);

ar(lower)alkanoyl [e.g., phenyl(lower)alkanoyl (e.g., phenylacetyl, phenylpropanoyl, phenylbutanoyl, phenylisobutanoyl, phenylpentanoyl, phenylhexanoyl, etc.), naphthyl(lower)alkanoyl (e.g., naphthylacetyl, naphthylpropanoyl, naphthylbutanoyl, etc.), etc.];

ar(lower)alkenoyl [e.g., phenyl(lower)alkenoyl (e.g., phenylpropenoyl, phenylbutenoyl, phenylmethacryloyl, phenylpentenoyl, phenylhexenoyl, etc.), naphthyl(lower)alkenoyl (e.g., naphthylpropenoyl, naphthylbutenyl, etc.), etc.];

ar(lower)alkoxycarbonyl [e.g., phenyl(lower)alkoxycarbonyl (e.g., benzyloxycarbonyl, etc.), etc.];

aryloxycarbonyl (e.g., phenoxycarbonyl, naphthyloxycarbonyl, etc.);

aryloxy(lower)alkanoyl (e.g., phenoxyacetyl, phenoxypropionyl, etc.);

arylglyoxyloyl (e.g., phenylglyoxyloyl, naphthylglyoxyloyl, etc.);

arylsulfonyl (e.g., phenylsulfonyl, p-tolylsulfonyl, etc.); or the like;

Heterocyclic acyl such as heterocycliccarbonyl; heterocyclic(lower)alkanoyl (e.g., heterocyclicacetyl, heterocyclicpropanoyl, heterocyclicbutanoyl, heterocyclicpentanoyl, heterocyclichexanoyl, etc.);

heterocyclic(lower)alkenoyl (e.g., heterocyclicpropenoyl, heterocyclicbutenoyl, heterocyclicpentenoyl, heterocyclichexenoyl, etc.); heterocyclicglyoxyloyl; or the like;

in which suitable "heterocyclic moiety" in the terms "heterocycliccarbonyl", "heterocyclic(lower)alkanoyl", "heterocyclic(lower)alkenoyl" and "heterocyclicglyoxyloyl" as mentioned above means, in more detail, saturated or unsaturated, monocyclic or polycyclic heterocyclic group containing at least one hetero-atom such as an oxygen, sulfur, nitrogen atom and the like.

And, especially preferable heterocyclic group may be heterocyclic group such as unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, pyrimidinyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;

saturated 3 to 8-membered (more preferably 5 or 6-membered) heteromonocyclic group containing 1 to 4 nitrogen atom(s), for example, pyrrolidinyl, imidazolidinyl, piperidyl, piperazinyl, etc.;

unsaturated condensed heterocyclic group containing 1 to 4 nitrogen atom(s), for example, indolyl, isoindolyl, indolinyl, indolizinyl, benzimidazolyl, quinolyl, isoquinolyl, indazolyl, benzotriazolyl, etc.;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 8-membered (more preferably 5 or 6-membered)heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, dihydrodithionyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered (more preferably 5 or 6-membered) heteromonocyclic group containing an oxygen atom, for example, furyl, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc.; and the like.

The acyl moiety as stated above may have one to ten, same or different, suitable substituent(s) such as lower alkyl as exemplified above, lower alkoxy as exemplified above, lower alkylthio wherein lower alkyl moiety is as exemplified above, lower alkylamino wherein lower alkyl moiety is as exemplified above, cyclo(lower)alkyl as exemplified above, cyclo(lower)alkenyl as exemplified above, halogen as exemplified above, aryl as exemplified above, amino, protected amino as exemplified above, hydroxy, protected hydroxy as exemplified above, cyano, nitro, carboxy, protected carboxy as exemplified above, sulfo, sulfamoyl, imino, oxo, amino (lower)alkyl wherein lower alkyl moiety is as exemplified above, carbamoyloxy, mono(or di or tri)halo(lower)alkyl wherein halogen moiety and lower alkyl moiety are each as exemplified above, diamino(lower)alkylidene (e.g. diaminomethylene, etc.), hydroxy(lower)alkyl wherein lower alkyl moiety is as exemplified above, [di(lower) alkylamino](lower)alkyl wherein lower alkyl moiety is as exemplified above, lower alkylpiperazinyl wherein lower alkyl moiety is as exemplified above, heterocyclic(lower)alkyl wherein heterocyclic moiety and lower alkyl moiety are each as exemplified above, dihydroxy(lower)alkyl wherein lower alkyl moiety is as exemplified above, or the like.

Suitable "lower alkylene" may include straight or branched one such as methylene, ethylene, trimethylene, tetramethylene, pentamethylene, hexamethylene, methylmethylene, ethylethylene, propylene, and the like.

Suitable "amidated carboxy" may include carbamoyl which may be substituted with one or two suitable substituent(s) or a group of the formula:

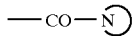

(wherein a group of the formula:

is a heterocyclic group containing at least one nitrogen atom, which may have suitable substituent(s)).

Suitable "heterocyclic group containing at least one nitrogen atom" may include unsaturated 3 to 8-membered (more preferably 5 or 6-membered) heteromonocyclic group containing 1 to 4-nitrogen atom(s), for example, pyrrolyl, pyrrolinyl, imidazolyl, pyrazolyl, dihydropyridyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.; saturated 3 to 8-membered (more preferably 5 or 6-membered) heteromonocyclic group containing 1 to 4 nitrogen atom(s), for example pyrrolidinyl, imidazolidinyl, piperidyl, piperazinyl, etc.;

unsaturated condensed heterocyclic group containing 1 to 4 nitrogen atom(s), for example, indolyl, isoindolyl, indolinyl, benzimidazolyl, indazolyl, benzotriazolyl, etc.;

saturated 3 to 8-membered (more preferably 5 or 6-membered) heteromonocyclic group containing 1 to 2 oxygen atom(s) and 1 to 3 nitrogen atom(s), for example, morpholinyl, etc.;

unsaturated 3 to 8-membered (more preferably 5 or 6-membered) heteromonocyclic group containing 1 to 2 sulfur atom(s) and 1 to 3 nitrogen atom(s), for example, dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated condensed heterocyclic group containing 1 to 2 oxygen atom(s) and 1 to 3 nitrogen atom(s), for example, benzoxazolyl, benzoxadiazolyl, benzoxazinyl, dihydrobenzoxazinyl (e.g. 2H-3,4-dihydro-1,4-benzoxazinyl, etc.);

unsaturated condensed heterocyclic group containing 1 to 2 sulfur atom(s) and 1 to 3 nitrogen atom(s), for example benzothiazolyl, benzothiadiazolyl, benzothiazinyl, dihydrobenzothiazinyl (e.g., 2H-3,4-dihydrobenzothiazinyl, etc.), etc.; and the like.

Suitable "heterobicyclic group" may include unsaturated condensed heterobicyclic group containing 1 to 4 nitrogen atom(s), for example, indolyl, isoindolyl, indolinyl, indolizinyl, benzimidazolyl, quinolyl, isoquinolyl, indazolyl, benzotriazolyl, quinoxalinyl, imidazopyridyl (e.g., imidazo[1,2-a]pyridyl, etc.;

unsaturated condensed heterobicyclic group containing 1 to 2 oxygen atom(s) and 1 to 3 nitrogen atom(s), for example, benzoxazolyl, benzoxadiazolyl, etc.;

unsaturated condensed heterobicyclic group containing 1 to 2 sulfur atom(s) and 1 to 3 nitrogen atom(s), for example, benzothiazolyl, benzothiadiazolyl, etc.;

unsaturated condensed heterobicyclic group containing 1 to 2 oxygen atom(s), benzofuryl(e.g.,benzo[b]furyl, etc.), dihydrobenzofuryl (e.g., 2,3-dihydrobenzo[b]furyl, etc.), lower alkylenedioxyphenyl (e.g., methylenedioxyphenyl, etc.), benzopyranyl (e.g., 2H-1-benzopyranyl, etc.), etc.;

unsaturated condensed heterobicyclic group containing 1 to 2 sulfur atom(s), for example, benzothienyl (e.g., benzo[b]thienyl, etc.), benzodithiinyl, etc.;

unsaturated condensed heterobicyclic group containing an oxygen atom and 1 to 2 sulfur atom(s), for example benzoxathiinyl, etc.; and the like.

Suitable "substituent" in the terms "aryl substituted with two suitable substituents", "carbamoyl which may be substituted with one or two suitable substituent(s)", "amino which may be substituted with one or two suitable substituent(s)" and "heterocyclic group containing at least one nitrogen atom, which may have suitable substituent(s)" may include lower alkyl as exemplified above, lower alkoxy as exemplified above, lower alkenyl as exemplified above, lower alkynyl as exemplified above, mono(or di or tri)halo (lower)alkyl wherein halogen moiety and lower alkyl moiety are each as exemplified above, cyclo(lower)alkyl as exemplified above, cyclo(lower)alkenyl as exemplified above, halogen as exemplified above, carboxy, protected carboxy as exemplified above, hydroxy, protected hydroxy as exemplified above, aryl as exemplified above, ar(lower)alkyl wherein aryl moiety and lower alkyl moiety are each as exemplified above, diamino(lower)alkylidene (e.g., diaminomethylene, etc.), dihydroxy(lower)alkyl wherein lower alkyl moiety is as exemplified above, lower alkylpiperazinyl wherein lower alkyl moiety is as exemplified above, carboxy(lower)alkyl wherein lower alkyl moiety is as exemplified above, protected carboxy(lower)alkyl wherein protected carboxy moiety and lower alkyl moiety are each as exemplified above, nitro, amino, protected amino as exemplified above, di(lower)alkylamino wherein lower alkyl moiety is as exemplified above, amino(lower)alkyl wherein lower alkyl moiety is as exemplified above, protected amino (lower)alkyl wherein protected amino moiety and lower alkyl moiety are each as exemplified above, hydroxy(lower)alkyl wherein lower alkyl moiety is as exemplified above, protected hydroxy(lower)alkyl wherein protected hydroxy moiety and lower alkyl moiety are each as exemplified above, acyl as exemplified above, cyano, [di(lower)alkylamino](lower)alkyl wherein lower alkyl moiety is as exemplified above, heterocyclic(lower)alkyl wherein heterocyclic moiety and lower alkyl moiety are each as exemplified above, sulfo, sulfamoyl, carbamoyloxy, mercapto, lower alkylthio wherein lower alkyl moiety is as exemplified above, imino, and the like.

Suitable "substituent" in the term "indenyl, indanyl, dihydrobenzocycloheptenyl, di(or tetra or hexa or octa or deca)hydronaphthyl, cyclopentenyl, dihydrothienyl, dihydrofuryl or heterobicyclic group, each of which may have suitable substituent(s)" may include lower alkyl as exemplified above, lower alkoxy as exemplified above, lower alkenyl as exemplified above, lower alkynyl as exemplified above, mono(or di or tri)halo(lower)alkyl wherein halogen moiety and lower alkyl moiety are each as exemplified above, cyclo(lower)alkyl as exemplified above, cyclo(lower)alkenyl as exemplified above, halogen as exemplified above, carboxy, protected carboxy as exemplified above, hydroxy, protected hydroxy as exemplified above, lower alkoxy(lower)alkyl wherein lower alkoxy moiety and lower alkyl moiety are each as exemplified above, aryl as exemplified above, ar(lower)alkyl wherein aryl moiety and lower alkyl moiety are each as exemplified above, carboxy(lower) alkyl wherein lower alkyl moiety is as exemplified above, protected carboxy(lower)alkyl wherein protected carboxy moiety and lower alkyl moiety are each as exemplified above, nitro, amino, protected amino as exemplified above, di(lower)alkylamino wherein lower alkyl moiety is as exemplified above, amino(lower)alkyl wherein lower alkyl moiety is as exemplified above, protected amino(lower)alkyl wherein protected amino moiety and lower alkyl moiety are each as exemplified above, hydroxy(lower)alkyl wherein lower alkyl moiety is as exemplified above, protected hydroxy(lower)alkyl wherein protected hydroxy moiety and lower alkyl moiety are each as exemplified above, lower alkylene as exemplified above, acyl as exemplified above, cyano, sulfo, hydroxyimino(lower)alkyl wherein lower alkyl moiety is as exemplified above, protected hydroxyimino (lower)alkyl wherein protected hydroxy and lower alkyl moiety are each as exemplified above, oxo, carbamoyloxy, mercapto, lower alkylthio wherein lower alkyl moiety is as exemplified above, imino, and the like.

Preferred embodiments of the object compound (I) are as follows.

$R^1$ is hydrogen; hydroxy(lower)alkyl; acyloxy(lower) alkyl; [di(lower)alkylamino(lower)alkyl]carbamoyl (lower)alkoxy; [di(lower)alkylamino(lower)alkyl] carbamoyl(lower)alkenyl; carbamoyl which may have diamino(lower)alkylidene, di(lower)alkylamino(lower) alkyl, heterocyclic(lower)alkyl (more preferably morpholinyl(lower)alkyl, pyrrolidinyl(lower)alkyl or piperidyl(lower)alkyl), dihydroxy(lower)alkyl or lower alkylpiperazinyl; or heterocycliccarbonyl (more preferably piperazinylcarbonyl) which may have lower alkyl; and $R^2$ is phenyl(lower)alkenyl; phenyl substituted with two suitable substituents (more preferably two substituents selected from the group consisting of halogen, lower alkoxy, hydroxy, lower alkyl and mono (or di or tri) halo(lower)alkyl); indenyl, indanyl, dihydrobenzocycloheptenyl, di(or tetra or hexa or octa or deca)hydronaphthyl, cyclopentenyl, dihydrothienyl, dihydrofuryl, benzofuryl, dihydrobenzofuryl, benzopyranyl, lower alkylenedioxyphenyl, quinolyl, isoquinolyl, quinoxalinyl, benzoxazolyl, imidazopyridyl, benzothienyl or indolyl, each of which may have 1 to 3 (more preferably one or two) suitable substituent(s) (more preferably substituent selected from the group consisting of oxo, hydroxyimino(lower) alkyl, protected hydroxyimino(lower)alkyl (more preferably acyloxyimino(lower)alkyl), hydroxy(lower) alkyl, protected hydroxy(lower)alkyl (more preferably acyloxy(lower)alkyl), mono(or di or tri)halo(lower) alkyl, halogen, lower alkylene, lower alkyl, lower alkoxy(lower)alkyl and cyano); lower alkylthienyl; mono(or di)halothienyl; [dihalo(lower)alkyl]thienyl; lower alkanoylthienyl; sulfamoylthienyl; halofuryl; or [dihalo(lower)alkyl]furyl.

More preferred embodiments of the object compound (I) are as follows.

$R^1$ is hydrogen; hydroxy(lower)alkyl; acyloxy(lower) alkyl; [di(lower)alkylamino(lower)alkyl]carbamoyl (lower)alkoxy; [di(lower)alkylamino(lower)alkyl] carbamoyl(lower)alkenyl; diamino(lower) alkylidenecarbamoyl; [di(lower)alkylamino(lower) alkyl]carbamoyl; [morpholinyl(lower)alkyl] carbamoyl; [pyrrolidinyl(lower)alkyl]carbamoyl; [piperidyl(lower)alkyl]carbamoyl; [dihydroxy(lower) alkyl]carbamoyl; [lower alkylpiperazinyl]carbamoyl; or lower alkylpiperazinylcarbonyl; and $R^2$ is phenyl(lower)alkenyl, dihalophenyl, di (lower) alkoxyphenyl, dihydroxyphenyl, di(lower)alkylphenyl, bis(trihalo(lower)alkyl)phenyl, indenyl, indanyl which may have oxo (more preferably oxoindanyl), dihydrobenzocycloheptenyl, dihydronaphthyl which may have hydroxyimino(lower)alkyl, hydroxy(lower) alkyl, dihalo(lower)alkyl or lower alkoxy(lower)alkyl (more preferably dihydronaphthyl, [hydroxyimino (lower)alkyl]dihydronaphthyl, [hydroxy(lower)alkyl] dihydronaphthyl, [dihalo(lower)alkyl]dihydronaphthyl or [lower alkoxy(lower)alkyl]dihydronaphthyl), octahydronaphthyl, cyclopentenyl which may have cyano (more preferably cyanocyclopentenyl), dihydrothienyl which may have cyano (more preferably cyanodihydrothienyl), dihydrofuryl which may have cyano (more preferably cyanodihydrofuryl), benzofuryl which may have lower alkyl, halogen or dihalo (lower)alkyl (more preferably benzofuryl, lower alkylbenzofuryl, halobenzofuryl or [dihalo(lower) alkyl]benzofuryl), dihydrobenzofuryl, benzopyranyl which may have one or two substituent(s) selected from the group consisting of lower alkyl, lower alkylene and halogen (more preferably benzopyranyl, di(lower) alkylbenzopyranyl, lower alkylenebenzopyranyl or halobenzopyranyl), methylenedioxyphenyl, auinolyl, isoquinolyl, quinoxalinyl, benzoxazolyl, imidazopyridyl which may have lower alkyl (more preferably lower alkylimidazopyridyl), benzothienyl which may have halogen or dihalo(lower)alkyl (more preferably benzothienyl, halobenzothienyl or dihalo(lower) alkylbenzothienyl), indolyl which may have lower alkyl (more preferably indolyl or lower alkylindolyl), lower alkylthienyl, mono(or di)halothienyl, [dihalo (lower)alkyl]thienyl, lower alkanoylthienyl, sulfamoylthienyl, halofuryl, or [dihalo(lower)alkyl] furyl.

The processes for preparing the object and starting compounds of the present invention are explained in detail in the following.

Process (1)

The compound (I) or a salt thereof can be prepared by reacting the compound (II) or its reactive derivative at the carboxy group, or a salt thereof with the compound (III) or its reactive derivative at the imino group, or a salt thereof.

Suitable reactive derivative at the imino group of the compound (III) may include a silyl derivative formed by the reaction of the compound (III) with a silyl compound such as bis(trimethylsilyl)acetamide, mono(trimethylsilyl) acetamide [e.g. N-(trimethylsilyl)acetamide], bis (trimethylsilyl)urea or the like; a derivative formed by reaction of the compound (III) with phosphorus trichloride or phosgene, and the like.

Suitable reactive derivative at the carboxy group of the compound (II) may include a conventional one such as an acid halide, an acid anhydride, an activated amide, an activated ester, and the like.

Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 1-hydroxy-1H-benzotriazole, 4-substituted imidazole, dimethylpyrazole, triazole or tetrazole; or an activated ester [e.g. cyanomethyl ester, methyl ester, ethyl ester, methoxymethyl ester,

vinyl ester, propargyl ester, 2-trifluoromethylsulfonyl-aminoethyl ester, 2-trifluoromethylsulfonylaminopropyl ester, 2-methyl-2-trifluoromethylsulfonylaminopropyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, benzothiazolyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (II) to be used.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (II) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N-diisopropylcarbodiimide; N-ethyl-N'-(3-dimethylaminopropyl)carbodiimide; N,N'-carbonyl-bis(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl) isoxazolium hydroxide intramolecular salt; 1-(p-chlorobenzenesulfonyloxy)-6-chloro-1H-benzotriazole; a combination of N-lower alkylhalopyridium halide (e.g., 1-methyl-2-chloropyridinium iodide, etc.) and tri(lower) alkylamine (e.g. triethylamine, etc.); so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine (e.g. triethylamine, etc.), pyridine, N-(lower)alkylmorpholine, N,N-di(lower)alkylbenzylamine, alkali metal lower alkoxide (e.g. sodium methoxide, etc.) or the like.

The reaction temperature is not critical, and the reaction is usually carried out under cooling to warming.

Process (A)

The compound (VI) or a salt thereof can be prepared by reacting the compound (IV) or a salt thereof with the compound (V) or a salt thereof.

The reaction can be carried out in the manners disclosed in Preparations 8 and 9 or similar manners thereto.

Process (B)

The compound (IIa) or a salt thereof can be prepared by reacting the compound (VI) or a salt thereof with the compound (VII) or a salt thereof.

The reaction can be carried out in the manner disclosed in Preparation 21 or similar manners thereto.

Process (C)

The compound (II) or a salt thereof can be prepared by reacting the compound (VIII) or a salt thereof with the compound (IX) or a salt thereof.

The reaction can be carried out in the manner disclosed in Preparation 6 or similar manners thereto.

Process (D)

The compound (VI) or a salt thereof can be prepared by reacting the compound (X) or a salt thereof with the compound (V) or a salt thereof.

The reaction can be carried out in the manner disclosed in Preparation 11 or similar manners thereto.

Process (E)

The compound (XII) or a salt thereof can be prepared by reacting the compound (XI) or a salt thereof with the compound (V) or a salt thereof.

The reaction can be carried out in the manner disclosed in Preparation 57 or similar manners thereto.

Process (F)

The compound (IIb) or a salt thereof can be prepared by subjecting the compound (XIIa) or its reactive derivative at the carboxy group, or a salt thereof to amidation reaction.

Suitable amidating reagent to be used in the present amidation reaction may include a compound of the formula:

(wherein $R^8$ is amino which may be substituted with one or two suitable substituent(s) or a group of the formula:

or its reactive derivative or a salt thereof, and the like.

Suitable reactive derivative of the compound (XVIII) may include Schiff's base type imino or its tautomeric enamine type isomer formed by the reaction of the compound (XVIII) with a carbonyl compound such as aldehyde, ketone or the like; a silyl derivative formed by the reaction of the compound (XVIII) with a silyl compound such as bis (trimethylsilyl)acetamide, mono(trimethylsilyl)acetamide [e.g. N-(trimethylsilyl)acetamide], bis(trimethylsilyl)urea or the like; a derivative formed by reaction of the compound (XVIII) with phosphorus trichloride or phosgene, and the like.

Suitable reactive derivative at the carboxy group of the compound (XIIa) may include an acid halide, an acid anhydride, an activated amide, an activated ester, and the like.

Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester,

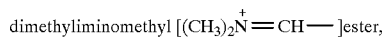

vinyl ester, ethyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethyl hydroxylamine, 1-hydroxy-2-(1H)pyridone, N-hydroxysuccinimide, N-hydroxyphthalimide, 1-hydroxy-1H-benzotriazole, etc.], and the like.

These reactive derivatives can optionally be selected from them according to the kind of the compound (XIIa) to be used.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, toluene, ethyl acetate, N,N-dimethylformamide, pyridine or any other organic solvent which does not adversely influence the reaction. These conventional solvent may also be used in a mixture with water. When the base and/or the starting compound are in liquid, they can be used also as a solvent.

In this reaction, when the compound (XIIa) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonyl-bis(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl) isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to heating.

Process (G)-①

The compound (XIV) or a salt thereof can be prepared by subjecting the compound (XIII) or a salt thereof to amidation reaction.

This reaction can be carried out in a similar manner to that of the aforementioned Process (F), and therefore the reagents to be used and the reaction conditions (e.g., solvent, reaction temperature, etc.) can be referred to those of the Process (F).

Process (G)-②

The compound (VIIIa) or a salt thereof can be prepared by subjecting the compound (XIV) or a salt thereof to introduction reaction of a leaving group.

The reaction can be carried out in the manner disclosed in Preparation 62 or 63 or similar manners thereto.

Process (H)-①

The compound (XVII) or a salt thereof can be prepared by reacting the compound (XV) or a salt thereof with the compound (XVI) or a salt thereof.

The reaction can be carried out in the manner disclosed in Preparation 8 or 9 or similar manners thereto.

Process (H)-②

The compound (XIIb) or a salt thereof can be prepared by subjecting the compound (XVII) or a salt thereof to halogenation reaction.

The reaction can be carried out in the manner disclosed in Preparation 26-(1) or similar manners thereto.

It is to be noted that the object compound (I) may include one or more stereoisomer(s) due to asymmetric carbon atom(s) and double bond(s) and all such isomers and mixture thereof are included within the scope of this invention.

Regarding the object compound (I), it is to be understood that they include tautomeric isomers.

That is, a group of the formula:

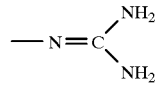

can be also alternatively represented by its tautomeric formula:

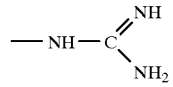

That is, both of the said groups are in the state of equilibrium and such tautomerism can be represented by the following equilibrium.

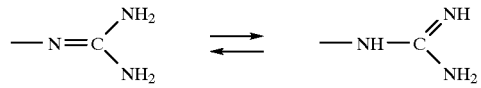

And it is obvious to any person skilled in the arts that both of the tautomeric isomers are easily convertible reciprocally and are included within the same category of the compound per se.

Accordingly, the both of the tautomeric forms of the object compound (I) are clearly included within the scope of the present invention.

In the present specification, the object compound including the group of such tautomeric isomers is represented by using one of the expressions therefor, that is the formula:

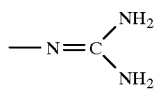

only for the convenient sake.

Suitable salts of the object and starting compounds and their reactive derivatives in Processes (1) and (A)–(H) can be referred to the ones as exemplified for the compound (I).

The new guanidine derivatives (I) and a pharmaceutically acceptable salt thereof of the present invention possess a strong inhibitory activity on $Na^+/H^+$ exchange in cells and therefore are useful as an inhibitor on $Na^+/H^+$ exchange in cells.

Accordingly, the new guanidine derivatives (I) and a pharmaceutically acceptable salt thereof can be used for the expectorant and for the treatment and/or prevention of cardiovascular diseases [e.g. hypertension, angina pectoris, myocardial infarction, heart failure (e.g. congestive heart tailure, acute heart failure, cardiac hypertrophy, etc.), arrhythmia (e.g. ischemic arrhythmia, arrhythmia due to myocardial infarction, arrhythmia after PTCA or after thrombolysis, etc.), restenosis after PTCA, etc.], cerebrovascular diseases [e.g. ischemic stroke, hemorrhagic stroke, etc.], renal diseases [e.g. diabetic nephropathy, ischemic acute renal failure, etc.], arteriosclerosis, shock [e.g. hemorrhagic shock, endotoxin shock, etc.] and the like, and can also be used as an agent for ischemic reperfusion injury, myocardial protection, organ protection in organ transplantation, open heart surgery, and the like.

In order to show the utilities of the guanidine derivatives (I) and a pharmaceutically acceptable salt thereof of the present invention, pharmacological test data of the representative compound of the guanidine derivatives (I) are illustrated in the following.

[1] Test Compound
  (a) [3-(2,3-dichlorophenyl)phenyl]guanidine methanesulfonate

[2] Inhibitory activity on $Na^+/H^+$ exchange in cells
  [i] Test Method
  Procedure was carried out according to a similar manner to the method described in Enzymology 173, 777 (1989).

Cell preparation: One male SD strain weighing 250–300 g was sacrificed with the blow on the head. Then, the thymus was removed into ice-cold NaCl medium (140 mM sodium chloride, 1 mM potassium chloride, 1 mM calcium chloride, 1 mM magnesium chloride, 10 mM glucose and 20 mM N-2-hydroxyethylpiperazine-N'-2-ethanesulfonic acid (HEADS)—pH 7.3), cut in small fragments, and transferred to glass homogenizer. The cells were dissociated by gentle strokes, and the resulting suspension was filtrated through six layers of surgical gauze and the filtrate was centrifuged at 4° C. at 1000 g for 5 minutes. The pellet was resuspended in RPMI 1640 medium (pH 7.3) at room temperature to adjust final cell concentration ($1 \times 10^7$ cells/ml).

Assay: This method detects the swelling that accompanies activation of $Na^+/H^+$ exchanger in cells incubated with sodium propionate. Propionic acid rapidly penetrates through the membrane. Intracellular dissociation brings about cytoplasmic acidification and consequently activation of $Na^+/H^+$ exchanger, which exchange extracellular $Na^+$ for cytoplasmic $H^+$. The uptake of osmotically obliged water is manifested as cell swelling.

Cell sizing and counting were performed electrically with the Coulter Counter-Channelyzer (AT-II). 0.1 ml Thymocytes solution were suspended in 20 ml sodium-propionate medium (140 mM sodium propionate, 1 mM potassium chloride, 1 mM calcium chloride, 1 mM magnesium chloride, 10 mM glucose, 20 mM N-2-hydroxyethylpiperazine-N'-2-ethanesulfonic acid (HEPES)—pH 6.8) including test compound solved in dimethyl sulfoxide (final concentration of dimethyl sulfoxide was 0.1°). During 4 minutes, increase of cell volume induced by $Na^+/H^+$ exchanger was kept linear, and the time course of swelling was observed each minute after the addition of thymocytes. Rate of Swelling (volume/min.) was measured by using 3–5 concentrations of test compound. Then, apparent Ki value of test compound was calculated by using Line weaver-Burk plot.

[3] Test Result:

| Test Compound | Ki (M) |
| --- | --- |
| (a) | $<1.0 \times 10^{-7}$ |

The object compound (I) or its pharmaceutically acceptable salts can usually be administered to mammals including human being in the form of a conventional pharmaceutical composition such as oral dosage form (e.g., capsule, microcapsule, tablet, granule, powder, troche, syrup, aerosol, inhalation, suspension, emulsion, etc.), injection dosage form, suppository, ointment, or the like.

The pharmaceutical composition of this invention can contain various organic or inorganic carrier materials, which are conventionally used for pharmaceutical purpose such as excipient (e.g., sucrose, starch, mannit, sorbit, lactose, glucose, cellulose, talc, calcium phosphate, calcium carbonate, etc.), binding agent (e.g., cellulose, methyl cellulose, hydroxypropylcellulose, polypropylpyrrolidone, gelatin, gum arabic, polyethyleneglycol, sucrose, starch, etc.), disintegrator (e.g., starch, carboxymethyl cellulose, calcium salt of carboxymethyl cellulose, hydroxypropylstarch, sodium glycolestarch, sodium bicarbonate, calcium phosphate, calcium citrate, etc.), lubricant (e.g., magnesium stearate, talc, sodium laurylsulfate, etc.), flavoring agent (e.g., citric acid, mentol, glycine, orange powders, etc.), preservative (e.g., sodium benzoate, sodium bisulfite, methylparaben, propylparaben, etc.), stabilizer (e.g., citric acid, sodium citrate, acetic acid, etc.), suspending agent (e.g., methyl cellulose, polyvinylpyrrolidone, aluminum stearate, etc.), dispersing agent, aqueous diluting agent (e.g., water, etc.), base wax (e.g., cacao butter, polyethyleneglycol, white petrolatum, etc.).

The effective ingredient may usually be administered with a unit dose of 0.01 mg/kg to 500 mg/kg, 1 to 4 times a day. However, the above dosage may be increased or decreased according to age, weight, conditions of the patient or the administering method.

The following Preparations and Examples are given for the purpose of illustrating the present invention in more detail.

PREPARATION 1

To a solution of 3,5-dichlorophenol (3 g), 4-dimethylaminopyridine (0.35 g) and 2,6-lutidine (2.57 ml) in dichloromethane (60 ml) was added dropwise bis (trifluoromethanesulfonic)anhydride (3.72 ml) at −30° C. The reaction mixture was stirred at room temperature for three hours. Saturated ammonium chloride solution was added to the reaction mixture and the product was extracted with dichloromethane twice. Dichloromethane was removed under reduced pressure and the residue was dissolved in ethyl acetate. The solution was washed successively with water, 10% hydrochloric acid, sodium hydrogencarbonate solution and brine. The organic layer was dried over magnesium sulfate and evaporated in vacuo to give 3,5-dichloro-1-trifluoromethylsulfonyloxybenzene.

IR (Neat): 1730, 1580, 1420, 1220 cm$^{-1}$

NMR (DMSO-d$_6$, δ): 7.81 (2H, dd, J=1.7, 1.7 Hz), 7.83 (1H, dd, J=1.7, 1.7 Hz)

Elemental Analysis Calcd. for C$_7$H$_3$Cl$_2$F$_3$O$_3$S: C 28.50, H 1.02 Found: C 28.41, H 1.01

PREPARATION 2

The following compounds were obtained according to a similar manner to that of Preparation 1.

(1) 4-Methoxycarbonyl-3-trifluoromethylsulfonyloxy-2,5-dihydrofuran

IR (Neat): 1730, 1690, 1430, 1210 cm$^{-1}$

NMR (DMSO-d$_6$, δ): 3.75 (3H, s), 4.75–4.88 (4H, m)

(+) APCI MASS: 277 (M+H)$^+$ (2) 4-Cyano-3-trifluoromethylsulfonyloxy-2,5-dihydrothiophene IR (Neat): 2250, 1660, 1430 cm$^{-1}$ NMR (DMSO-d$_6$, δ): 3.96–4.02 (2H, m), 4.13–4.19 (2H, m)

Elemental Analysis Calcd. for C$_6$H$_4$F$_3$NO$_3$S$_2$: C 27.80, H 1.56, N 5.40 Found: C 27.58, H 1.73, N 5.24

(3) 2-Methyl-8-trifluoromethylsulfonyloxyimidazo[1,2-a]-pyridine mp: 63–64° C.

IR (Nujol): 3150, 1540, 1500, 1210 cm$^{-1}$

NMR (DMSO-d$_6$, δ): 2.39 (3H, s), 6.93 (1H, dd, J=7.6, 6.8 Hz), 7.42 (1H, d, J=7.6 Hz), 7.91 (1H, s), 8.59 (1H, d, J=6.8 Hz)

(+) APCI MASS: 281 (M+H)$^+$

Elemental Analysis Calcd. for C$_9$H$_7$F$_3$N$_2$O$_3$S: C 38.58, H 2.52, N 10.00 Found: C 38.38, H 2.37, N 9.82

(4) 5-Trifluoromethylsulfonyloxyquinoline mp: 88–89° C.

IR (Nujol): 1620, 1560, 1490, 1410, 1210 cm$^{-1}$

NMR (DMSO-d$_6$, δ): 7.98–8.11 (2H, m), 8.29 (1H, dd, J=7.4, 2.3 Hz), 9.17 (2H, s)

(+) APCI MASS: 279 (M+H)$^+$

Elemental Analysis Calcd. for C$_9$H$_5$F$_3$N$_2$O$_3$S: C 38.86, H 1.81, N 10.07 Found: C 38.85, H 1.62, N 9.95

(5) 5-Trifluoromethylsulfonyloxyisoquinoline

IR (Neat): 1630, 1590, 1420, 1370, 1210, 1140 cm$^{-1}$

NMR (DMSO-d$_6$, δ): 7.82–7.91 (2H, m), 8.02 (1H, d, J=8.1 Hz), 8.36 (1H, d, J=8.1 Hz), 8.78 (1H, d, J=6.0 Hz), 9.56 (1H, s)

(+) APCI MASS: 278 (M+H)$^+$

Elemental Analysis Calcd. for C$_{10}$H$_6$F$_3$NO$_3$S: C 43.33, H 2.18, N 5.05 Found: C 43.53, H 2.18, N 5.02

(6) 8-Trifluoromethylsulfonyloxyquinoline mp: 65–67° C.

IR (Nujol): 1600, 1490, 1200, 1130 cm$^{-1}$

NMR (DMSO-d$_6$, δ): 7.71–7.80 (2H, m), 7.93 (1H, d, J=7.0 Hz), 8.17 (1H, d, J=7.0 Hz), 8.59 (1H, dd, J=8.4, 1.6 Hz), 9.11 (1H, dd, J=4.2, 1.6 Hz)

(+) APCI MASS: 278 (M+H)$^+$

Elemental Analysis Calcd. for C$_{10}$H$_6$F$_3$NO$_3$S: C 43.33, H 2.18, N 5.05 Found: C 43.47, H 2.01, N 5.02

(7) 1,3-Dichloro-2-trifluoromethylsulfonyloxybenzene

IR (Neat): 1730, 1580, 1420, 1210, 1130 cm$^{-1}$

NMR (DMSO-d$_6$, δ): 7.57 (1H, dd, J=7.4, 7.4 Hz), 7.79 (2H, d, J=7.4 Hz)

Elemental Analysis Calcd. for C$_7$H$_3$Cl$_3$F$_3$O$_3$S: C 28.50, H 1.02 Found: C 28.38, H 0.86

(8) 3,5-Dimethoxy-1-trifluoromethylsulfonyloxybenzene

IR (Neat): 1620, 1480, 1420, 1200 cm$^{-1}$

NMR (DMSO-d$_6$, δ): 3.80 (6H, s), 6.65 (3H, s)

(+) APCI MASS: 287 (M+H)$^+$ (9) 4-Trifluoromethylsulfonyloxybenzofuran

IR (Film): 1425, 1220, 1140, 990 cm$^{-1}$

NMR (DMSO-d$_6$, δ): 7.08 (1H, d, J=2.2 Hz), 7.43 (1H, dd, J=7.9, 1.0 Hz), 7.51 (1H, dd, J=7.9, 7.9 Hz), 7.84 (1H, dd, J=7.9, 1.0 Hz), 8.23 (1H, d, J=2.2 Hz)

(10) 4-Trifluoromethylsulfonyloxybenzoxazole

IR (Film): 1620, 1605, 1420 1220, 1140 cm$^{-1}$

NMR (DMSO-d$_6$, δ): 7.55–7.70 (2H, m), 7.98 (1H, dd, J=7.1, 1.96 Hz), 8.99 (1H, s)

PREPARATION 3

To a solution of 3-methoxycarbonyl-5-iodobenzoic acid (1 g) in tetrahydrofuran (10 ml) was added at −40° C. to −30° C. triethylamine (0.55 ml) followed by slow addition of isobutyl chloroformate (0.51 ml) under nitrogen atmosphere. The reaction mixture was stirred below −20° C. for 45 minutes. Then, triethylamine hydrochloride was filtered off and washed with cold tetrahydrofuran, and the filtrate was added as quickly as possible to a suspension of sodium borohydride (0.37 g) in tetrahydrofuran-water (8:1, 8 ml) at 0° C. with vigorous stirring. The stirring was continued at ambient temperature for 4 hours, followed by acidification of the solution to pH 5. The tetrahydrofuran was removed under reduced pressure, and the product was extracted with ethyl acetate. The organic layer was washed with water and brine and dried over magnesium sulfate. Ethyl acetate was removed under reduced pressure and the residue was purified by column chromatography on silica gel eluting with a mixture of chloroform and methanol (30:1). The fractions containing the desired product were collected and evaporated in vacuo to give methyl 3-hydroxymethyl-5-iodobenzoate.

mp: 57–58° C.

IR (Nujol): 1720, 1560, 1270 cm$^{-1}$

NMR (DMSO-d$_6$, δ): 3.86 (3H, s), 4.54 (2H, d, J=5.8 Hz), 5.44 (1H, t, J=5.8 Hz), 7.92 (1H, dd, J=1.5, 1.5 Hz), 7.94 (1H, dd, J=1.5, 1.5 Hz), 8.09 (1H, dd, J=1.5, 1.5 Hz)

(+) APCI MASS: 293 (M+H)$^+$

Elemental Analysis Calcd. for C$_9$H$_9$IO$_3$: C 37.01, H 3.11 Found: C 37.32, H 2.96

PREPARATION 4

To a cold (−78° C.) solution of 1-bromo-3,5-dichlorobenzene (14 g) and triisopropoxyborane (20.8 ml) in tetrahydrofuran (140 ml) was added dropwise n-butyllithium in hexane (1.66 M, 52.3 ml). The mixture was stirred at −78° C. for one hour and warmed to room temperature over two hours. The reaction mixture was poured onto 2M hydrochloric acid solution (120 ml) and stirred for 10 minutes. The product was extracted with ether (200 ml) 3 times, and the organic layers were combined, washed with brine, dried over magnesium sulfate and evaporated in vacuo. To the residue was added petroleum ether and the crystalline was collected, washed with petroleum ether and dried to give 3,5-dichlorophenyl-dihydroxyborane.

mp: 293° C. (dec.)

IR (Nujol): 1580, 1560, 1290 cm$^{-1}$

NMR (DMSO-d$_6$, δ): 7.58 (1H, dd, J=2.0, 2.0 Hz), 7.75 (2H, dd, J=2.0, 2.0 Hz)

PREPARATION 5

The following compounds were obtained according to a similar manner to that of Preparation 4.

(1) 2,3-Dichlorophenyl-dihydroxyborane
mp: 205–207° C.
IR (Nujol): 3200, 1580, 1400, 1290 cm$^{-1}$
NMR (DMSO-$d_6$, δ): 7.22–7.37 (2H, m), 7.50–7.64 (2H, m), 7.76–7.81 (1H, m)

(2) 3,5-Bis(trifluoromethyl)phenyl-dihydroxyborane
mp: 199–202° C.
IR (Nujol): 3200, 1620 cm$^{-1}$
NMR (DMSO-$d_6$, δ): 8.02–8.11 (2H, m), 8.25 (1H, s), 8.46 (2H, s)

(3) 3,5-Difluorophenyl-dihydroxyborane
mp: >300° C.
IR (Nujol): 3250, 1580, 1330, 1120 cm$^{-1}$
NMR (DMSO-$d_6$, δ): 7.20–7.28 (1H, m), 7.40–7.49 (2H, m)

(4) 3,5-Dimethylphenyl-dihydroxyborane
mp: 163–165° C.
IR (Nujol): 3200, 1600, 1220, 1190 cm$^{-1}$
NMR (DMSO-$d_6$, δ): 2.25 (6H, s), 7.02 (1H, s), 7.38 (2H, s)

(5) (2-Chlorothiophen-3-yl)-dihydroxyborane
mp: 155° C. (dec.)
IR (Nujol): 3250, 1510, 1320 cm$^{-1}$
NMR (DMSO-$d_6$, δ): 7.16 (1H, d, J=5.6 Hz), 7.35 (1H, d, J=5.6 Hz), 8.16 (2H, br s)

(6) 3-(4,4-Dimethyl-4,5-dihydrooxazol-2-yl)phenyl-dihydroxyborane
mp: 105–107° C.
IR (Nujol): 3300 (br), 1640, 1360, 1180 cm$^{-1}$
NMR (DMSO-$d_6$, δ): 1.30 (6H, s), 4.11 (2H, s), 7.39–7.54 (1H, m), 7.82–8.38 (2H, m)

PREPARATION 6

The mixture of 3,5-difluorophenyl-dihydroxyborane (3 g), 3-iodobenzoic acid (3.37 g), sodium carbonate (4.31 g) and palladium(II) acetate (0.030 g) in water (60 ml) was stirred at room temperature for six hours. The reaction mixture was filtered and was washed with ether (30 ml) twice. The aqueous layer was adjusted to pH 2 with 6N hydrochloric acid. The crystalline was collected, washed with water and dried to afford 3-(3,5-difluorophenyl)benzoic acid.
mp: 219–222° C.
IR (Nujol): 1690, 1600, 1310, 1120 cm$^{-1}$
NMR (DMSO-$d_6$, δ): 7.22–7.32 (1H, m), 7.45–7.51 (2H, m), 7.63 (1H, dd, J=7.8, 7.8 Hz), 7.96–8.04 (2H, m), 8.22 (1H, dd, J=1.6, 1.6 Hz)
(−) APCI MASS: 233 (M−H)$^-$

PREPARATION 7

The following compounds were obtained according to a similar manner to that of Preparation 6.

(1) Methyl 3-(3,5-dichlorophenyl)-5-hydroxymethylbenzoate
mp: 128–130° C.
IR (Nujol): 3250, 1720, 1560, 1250 cm$^{-1}$
NMR (DMSO-$d_6$, δ): 3.90 (3H, s), 4.65 (2H, d, J=5.8 Hz), 5.43 (1H, dd, J=5.8 Hz), 7.65 (1H, dd, J=1.8, 1.8 Hz), 7.76 (2H, dd, J=1.8, 1.8 Hz), 7.92 (1H, s), 8.01 (1H, s), 8.08 (1H, s)
(+) APCI MASS: 311 (M+H)$^+$ (2) 3-[3,5-Bis(trifluoromethyl)phenyl]benzoic acid
mp: 205–207° C.
IR (Nujol): 1680, 1280 cm$^{-1}$
NMR (DMSO-$d_6$, δ): 7.67 (1H, dd, J=7.8, 7.8 Hz), 8.03–8.13 (3H, m), 8.31 (1H, s), 8.37 (2H, s)
(−) APCI MASS: 333 (M−H)$^-$ (3) 3-(3,5-Dimethylphenyl)benzoic acid
IR (Nujol): 1680, 1300 cm$^{-1}$
NMR (DMSO-$d_6$, δ): 2.35 (6H, s), 7.03 (1H, s), 7.30 (2H, s), 7.56 (1H, dd, J=7.7, 7.7 Hz), 7.82 (1H, ddd, J=7.7, 1.7, 1.7 Hz), 7.94 (1H, ddd, J=7.7, 1.7, 1.7 Hz), 8.18 (1H, dd, J=1.7, 1.7 Hz)
(+) APCI MASS: 227 (M+H)$^+$ (4) 3-(2-Chlorothiophen-3-yl)benzoic acid
mp: 175–177° C.
IR (Nujol): 2600, 1680, 1310 cm$^{-1}$
NMR (DMSO-$d_6$, δ): 7.31 (1H, d, J=5.7 Hz), 7.58–7.66 (2H, m), 7.84 (1H, ddd, J=7.8, 1.5, 1.5 Hz), 7.97 (1H, ddd, J=7.8, 1.5, 1.5 Hz), 8.16 (1H, dd, J=1.5, 1.5 Hz), 13.16 (1H, br s)
(+) APCI MASS: 239 (M+H)$^+$

PREPARATION 8

A mixture of 3,4-dihydro-1-(trifluoromethylsulfonyloxy)naphthalene (1.0 g), 3-(4,4-dimethyl-4,5-dihydrooxazol-2-yl)phenyl-dihydroxyborane (1.1 g), tetrakis(triphenylphosphine)palladium(0) (0.21 g), lithium chloride (0.46 g), 2M sodium carbonate aqueous solution (5.1 ml) in 1,2-dimethoxyethane (12 ml) was heated at 85° C. and stirred vigorously for 3 hours under nitrogen atmosphere. After being cooled to room temperature, the reaction mixture was concentrated under reduced pressure. The residue was partitioned between dichloromethane (35 ml) and 2N sodium carbonate aqueous solution (35 ml) and conc. ammonia solution (2.0 ml). The aqueous layer was extracted again with dichloromethane (35 ml) and the combined organic extracts are dried over magnesium sulfate. The solvent was evaporated in vacuo and the residue was purified by column chromatography on silica gel eluting with a mixture of toluene and ethyl acetate (30:1). The eluted fractions containing the desired product were collected and evaporated in vacuo to give 2-[3-(3,4-dihydro-1-naphthyl)phenyl]-4,4-dimethyl-4,5-dihydrooxazole (1.05 g).
mp: 84–85° C.
IR (Nujol): 1645, 1595 cm$^{-1}$
NMR (DMSO-$d_6$, δ): 1.28 (6H, s), 2.3–2.5 (2H, m), 2.7–2.9 (2H, m), 4.10 (2H, s), 6.14 (1H, t, J=4.7 Hz), 6.8–6.9 (1H, m), 7.1–7.3 (3H, m), 7.4–7.6 (2H, m), 7.7–7.9 (2H, m)
(+) APCI MASS: 304 (M+H)$^+$
Elemental Analysis Calcd. for $C_{21}H_{21}NO$: C 83.13, H 6.98, N 4.62 Found: C 82.84, H 7.20, N 4.56

PREPARATION 9

A mixture of 4-trifluoromethylsulfonyloxy-benzofuran (2 g), 3-(4,4-dimethyl-4,5-dihydrooxazol-2-yl)phenyldihydroxyborane (2.14 g), tetrakis(triphenylphosphine)palladium(0) (0.26 g) and triethylamine (2.28 g) in N,N-dimethylformamide (40 ml) was heated at 85° C. for 3 hours under nitrogen atmosphere. After evaporating the solvent, the residue was dissolved in a mixture of ethyl acetate (100 ml) and water (100 ml). The organic layer was successively washed with 10% sodium carbonate aqueous solution, brine and dried over magnesium sulfate. The solvent was evaporated in vacuo and the residue was purified by column chromatography on silica gel eluting with toluene. The fractions containing the desired products were collected and evaporated in vacuo to afford 2-[3-(benzofuran-4-yl)phenyl]-4,4-dimethyl-4,5-dihydrooxazole (1.52 g).
IR (Film): 1640, 1600, 1350, 970 cm$^{-1}$
NMR (DMSO-d$_6$, δ): 1.31 (6H, s), 4.15 (2H, s), 7.01–7.03 (1H, m), 7.39–7.49 (2H, m), 7.60–7.69 (2H, m), 7.81–7.93 (2H, m), 8.07–8.12 (2H, m)
(+) APCI MASS: 292 (M+H)$^+$

PREPARATION 10

The following compounds were obtained according to similar manners to those of Preparations 8 and 9.

(1) 4,4-Dimethyl-2-[3-(6-fluoro-2H-1-benzopyran-4-yl)phenyl]-4,5-dihydrooxazole
IR (Film): 2960, 1645, 1595, 1580 cm$^{-1}$
NMR (DMSO-d$_6$, δ): 1.29 (6H, s), 4.12 (2H, s), 4.83 (2H, d, J=4.0 Hz), 6.09 (1H, t, J=4.0 Hz), 6.61 (1H, dd, J=3.0, 9.4 Hz), 6.9–7.1 (2H, m), 7.5–7.9 (4H, m)
(+) APCI MASS: 324 (M+H)$^+$ (2) 2-[3-(4aRS,8aSR-3,4,4a,5,6,7,8,8a-octahydro-1-naphthyl)phenyl]-4,4-dimethyl-4,5-dihydrooxazole
mp: 98–100° C.
IR (Nujol): 1650, 1570 cm$^{-1}$
NMR (DMSO-d$_6$, δ): 0.6–0.8 (1H, m), 1.1–1.8 (16H, m), 2.1–2.3 (3H, m), 4.09 (2H, s), 5.6–5.8 (1H, m), 7.3–7.7 (4H, m)
(+) APCI MASS: 310 (M+H)$^+$ (3) 4,4-Dimethyl-2-[3-(2-hydroxymethyl-3,4-dihydro-1-naphthyl)phenyl]-4,5-dihydrooxazole
IR (Film): 3250, 2950, 1640, 1590 cm$^{-1}$
NMR (DMSO-d$_6$, δ): 1.28 (6H, s), 2.4–2.6 (2H, m), 2.8–2.9 (2H, m), 3.84 (2H, d, J=5.4 Hz), 4.10 (2H, s), 4.76 (1H, t, J=5.4 Hz), 6.42 (1H, d, J=7.3 Hz), 7.0–7.9 (7H, m)
(+) APCI MASS: 334 (M+H)$^+$ (4) 4,4-Dimethyl-2-[3-[spiro[2H-1-benzopyran-2,1'-cyclopentane]-4-yl]phenyl]-4,5-dihydrooxazole
IR (Film): 2960, 1645, 1600 cm$^{-1}$
NMR (DMSO-d$_6$, δ): 1.29 (6H, s), 1.6–2.2 (8H, m), 4.12 (2H, s), 5.90 (1H, s), 6.8–7.9 (8H, m)
(+) APCI MASS: 360 (M+H)$^+$ (5) 4,4-Dimethyl-2-[3-(2,2-dimethyl-2H-1-benzopyran-4-yl)phenyl]-4,5-dihydrooxazole
mp: 110–111° C.
IR (Nujol): 1645, 1595 cm$^{-1}$
NMR (DMSO-d$_6$, δ): 1.29 (6H, s), 1.45 (6H, s), 4.12 (2H, s), 5.81 (1H, s), 6.8–7.0 (3H, m), 7.1–7.3 (1H, m), 7.4–7.6 (2H, m), 7.7–7.9 (2H, m)
(+) APCI MASS: 334 (M+H)$^+$ (6) 2-[3-(2H-1-Benzopyran-4-yl)phenyl]-4,4-dimethyl-4,5-dihydrooxazole
IR (Film): 3050, 2950, 1640, 1600, 1570 cm$^{-1}$
NMR (DMSO-d$_6$, δ): 1.28 (6H, s), 4.11 (2H, s), 4.83 (2H, d, J=4.0 Hz), 5.98 (1H, t, J=4.0 Hz), 6.8–7.0 (3H, m), 7.1–7.3 (1H, m), 7.4–7.6 (2H, m), 7.7–7.9 (2H, m)
(+) APCI MASS: 306 (M+H)$^+$ (7) 2-[3-(6,7-Dihydro-5H-benzocyclohepten-9-yl)phenyl]-4,4-dimethyl-4,5-dihydrooxazole
IR (Film): 2960, 2930, 1645, 1590 cm$^{-1}$
NMR (DMSO-d$_6$, δ): 1.25 (6H, s), 1.8–2.2 (4H, m), 2.5–2.7 (2H, m), 4.06 (2H, s), 6.51 (1H, t, J=7.3 Hz), 6.8–6.9 (1H, m), 7.2–7.8 (7H, m)
(+) APCI MASS: 318 (M+H)$^+$ (8) 2-[3-(3,5-Dichlorophenyl)phenyl]-4,4-dimethyl-4,5-dihydrooxazole
IR (Neat): 1740, 1650, 1580, 1560, 1240 cm$^{-1}$
NMR (DMSO-d$_6$, δ): 1.32 (6H, s), 4.15 (2H, s), 7.58 (1H, dd, J=7.8, 7.8 Hz), 7.63 (1H, dd, J=1.7, 1.7 Hz), 7.73 (2H, dd, J=1.7, 1.7 Hz), 7.87–7.92 (2H, m), 8.07 (1H, dd, J=1.7, 1.7 Hz)
(+) APCI MASS: 320 (M+H)$^+$ (9) Methyl 3-(3,5-dichlorophenyl)-5-methoxycarbonylbenzoate
mp: 117–120° C.
IR (Nujol): 1730, 1560, 1330, 1240 cm$^{-1}$
NMR (DMSO-d$_6$, δ): 3.93 (6H, s), 7.69 (1H, dd, J=1.8, 1.8 Hz), 7.82 (2H, dd, J=1.8, 1.8 Hz), 8.4 (1H, dd, J=1.6, 1.6 Hz), 8.48 (2H, dd, J=1.6, 1.6 Hz)
(+) APCI MASS: 339 (M+H)$^+$

(10) 2-[3-(Benzofuran-7-yl)phenyl]-4,4-dimethyl-4,5-dihydrooxazole
IR (Film): 1635, 1590, 790 cm$^{-1}$
NMR (DMSO-d$_6$, δ): 1.32 (6H, s), 4.15 (2H, s), 7.07 (1H, d, J=2.2 Hz), 7.38 (1H, dd, J=7.6, 7.6 Hz), 7.53–7.75 (3H, m), 7.88–8.05 (2H, m), 8.12 (1H, d, J=2.2 Hz), 8.34–8.35 (1H, m)
(+) APCI MASS: 292 (M+H)$^+$

(11) 4,4-Dimethyl-2-[3-(4-methoxycarbonyl-2,5-dihydrofuran-3-yl)phenyl-4,5-dihydrooxazole
IR (Neat): 1720, 1650, 1430, 1270, 1230 cm$^{-1}$
NMR (DMSO-d$_6$, δ): 1.29 (6H, s), 3.65 (3H, s), 4.12 (2H, s), 4.92 (2H, t-like, J=5.0 Hz), 5.05 (2H, t-like, J=5.0 Hz), 7.50 (1H, dd, J=7.7, 7.7 Hz), 7.66 (1H, ddd, J=7.7, 1.6, 1.6 Hz), 7.87 (1H, ddd, J=7.7, 1.6, 1.6 Hz), 7.94 (1H, dd, J=1.6, 1.6 Hz)
(+) APCI MASS: 302 (M+H)$^+$

(12) 2-[3-(2-Cyano-1-cyclopenten-1-yl)phenyl]-4,4-dimethyl-4,5-dihydrooxazole
mp: 100–102° C.
IR (Nujol): 2200, 1650, 1300, 1180 cm$^{-1}$
NMR (DMSO-d$_6$, δ): 1.30 (6H, s), 2.03 (2H, tt, J=7.5, 7.5 Hz), 2.76–2.85 (2H, m), 2.92–3.01 (2H, m), 4.14 (2H, s), 7.59 (1H, dd, J=7.8, 7.8 Hz), 7.84–7.94 (2H, m), 8.13 (1H, dd, J=1.6, 1.6 Hz)
(+) APCI MASS: 267 (M+H)$^+$
Elemental Analysis Calcd. for C$_{17}$H$_{18}$N$_2$O: C 76.66, H 6.81, N 10.52 Found: C 76.98, H 6.86, N 10.15

(13) 2-Methyl-8-[3-(4,4-dimethyl-4,5-dihydrooxazol-2-yl)phenyl]imidazo[1,2-a]pyridine
IR (Neat): 3300, 1730, 1650, 1590, 1540 cm$^{-1}$
NMR (DMSO-d$_6$, δ): 1.31 (6H, s), 2.37 (3H, s), 4.15 (2H, s), 6.94 (1H, dd, J=7.0, 6.9 Hz), 7.42 (1H, dd, J=7.0, 1.1 Hz), 7.59 (1H, dd, J=7.8, 7.8 Hz), 7.79 (1H, s), 7.88 (1H, ddd, J=7.8, 1.3, 1.3 Hz), 8.26 (1H, ddd, J=7.8, 1.3, 1.3 Hz), 8.32–8.52 (2H, m)
(+) APCI MASS: 306 (M+H)$^+$

(14) 4,4-Dimethyl-2-[3-(5-quinoxalinyl)phenyl]-4,5-dihydrooxazole
IR (Neat): 3300, 1730, 1640, 1350, 1240 cm$^{-1}$
NMR (DMSO-d$_6$, δ): 1.30 (6H, s), 4.13 (2H, s), 7.60 (1H, dd, J=7.7, 7.7 Hz), 7.82 (1H, ddd, J=7.7, 1.7, 1.7 Hz), 7.90–8.01 (3H, m), 8.10 (1H, dd, J=1.7, 1.7 Hz), 8.16 (1H, dd, J=7.3, 2.6 Hz), 8.97 (1H, d, J=1.8 Hz), 9.00 (1H, d, J=1.8 Hz)
(+) APCI MASS: 304 (M+H)$^+$

(15) 4,4-Dimethyl-2-[3-(5-isoquinolyl)phenyl]-4,5-dihydrooxazole
IR (Neat): 1730, 1650 cm$^{-1}$
NMR (DMSO-d$_6$, δ): 1.30 (6H, s), 4.14 (2H, s), 7.61 (1H, d, J=5.9 Hz), 7.65–7.72 (2H, m), 7.76–7.80 (2H, m), 7.92 (1H, s), 7.95–8.01 (1H, m), 8.18–8.24 (1H, m), 8.52 (1H, d, J=6.0 Hz), 9.42 (1H, s)
(+) APCI MASS: 303 (M+H)$^+$

(16) 4,4-Dimethyl-2-[3-(8-quinolyl)phenyl]-4,5-dihydrooxazole
IR (Neat): 3200, 1730, 1640, 1600, 1500, 1350, 1240 cm$^{-1}$ NMR (DMSO-d$_6$, δ): 1.30 (6H, s), 4.13 (2H, s), 7.53–7.62 (2H, m), 7.70 (1H, dd, J=7.8, 7.8 Hz), 7.78–7.83 (2H, m), 7.90 (1H, ddd, J=7.8, 1.4, 1.4 Hz), 8.04 (1H, dd, J=7.8, 1.8 Hz), 8.10 (1H, dd, J=1.4, 1.4 Hz), 8.46 (1H, dd, J=8.3, 1.8 Hz), 8.92 (1H, dd, J=4.1, 1.8 Hz)

(+) APCI MASS: 303 (M+H)$^+$

(17) 4,4-Dimethyl-2-[3-(3,5-dimethoxyphenyl)phenyl]-4,5-dihydrooxazole

IR (Neat): 3400, 1730, 1640, 1580, 1350 cm$^{-1}$

NMR (DMSO-d$_6$, δ): 1.31 (6H, s), 3.84 (6H, s), 4.14 (2H, s), 6.54 (1H, dd, J=2.2, 2.2 Hz), 6.78 (2H, dd, J=2.2, 2.2 Hz), 7.55 (1H, dd, J=7.8, 7.8 Hz), 7.80–7.89 (2H, m), 8.04 (1H, dd, J=1.5, 1.5 Hz)

(+) APCI MASS: 312 (M+H)$^+$

PREPARATION 11

A mixture of 3-trifluoromethylsulfonyloxy-1H-indene (1.0 g), triphenylarsine (92 mg) and tris(dibenzylideneacetone)dipalladium(0) (35 mg) in anhydrous degassed N-methyl-2-pyrrolidone (16 ml) was stirred for 5 minutes, at room temperature. To the reaction mixture was added 3-(4,4-dimethyl-4,5-dihydrooxazol-2-yl)phenyltri(n-butyl)tin (1.93 g) in N-methyl-2-pyrrolidone (8 ml). After stirring for 22 hours at room temperature, the reaction mixture was stirred for 5 hours at 60° C., treated with 1M potassium fluoride aqueous solution, diluted with ethyl acetate and filtered. The organic layer was successively washed with water and brine and dried over magnesium sulfate. The solvent was evaporated in vacuo and the residue was purified by column chromatography on silica gel eluting with a mixture of toluene and ethyl acetate (30:1). The eluted fractions containing the desired product were collected and evaporated in vacuo to give 4,4-dimethyl-2-[3-(1H-inden-3-yl)phenyl]-4,5-dihydrooxazole (0.82 g).

IR (Film): 3060, 2960, 2900, 1645, 1600 cm$^{-1}$

NMR (DMSO-d$_6$, δ): 1.31 (6H, s), 3.5–3.6 (2H, m), 4.14 (2H, s), 6.7–6.8 (1H, m), 7.2–8.1 (8H, m)

(+) APCI MASS: 290 (M+H)$^+$

PREPARATION 12

The following compounds were obtained according to a similar manner to that of Preparation 11.

(1) 2-[3-(4-Cyano-2,5-dihydrothiophen-3-yl)phenyl]-4,4-dimethyl-4,5-dihydrooxazole IR (Neat): 2200, 1650, 1350 cm$^{-1}$ NMR (DMSO-d$_6$, δ): 1.29 (6H, s), 4.10–4.16 (4H, m), 4.39 (2H, t-like, J=4.4 Hz), 7.61 (1H, dd, J=7.8, 7.8 Hz), 7.83–7.88 (1H, m), 7.96 (1H, ddd, J=7.8, 1.5, 1.5 Hz), 8.09 (1H, dd, J=1.5, 1.5 Hz)

(+) APCI MASS: 285 (M+H)$^+$ (2) 2-[3-(2,6-Dichlorophenyl)phenyl]-4,4-dimethyl-4,5-dihydrooxazole IR (Neat): 1730, 1650, 1420, 1310, 1250 cm$^{-1}$ NMR (DMSO-d$_6$, δ): 1.29 (6H, s), 4.13 (2H, s), 7.42–7.50 (2H, m), 7.57–7.69 (4H, m), 7.92 (1H, ddd, J=7.8, 1.4, 1.4 Hz)

(+) APCI MASS: 320 (M+H)$^+$

PREPARATION 13

To a solution of 2-[3-(3,4-dihydro-1-naphthyl)phenyl]-4,4-dimethyl-4,5-dihydrooxazole (0.5 g) in dichloromethane (3.5 ml) was added bis(trifluoromethanesulfonic)anhydride (0.28 ml) under ice cooling. After stirring for 30 minutes under ice cooling, to the reaction mixture was added water. After stirring for 15 minutes at room temperature, the organic layer was successively washed with 1N hydrochloric acid, water and brine and dried over magnesium sulfate. The solvent was evaporated in vacuo and the residue was purified by column chromatography on silica gel eluting with toluene. The eluted fractions containing the desired product were collected and evaporated in vacuo to give 2-methyl-2-trifluoromethylsulfonylaminopropyl 3-(3,4-dihydro-1-naphthyl)benzoate (0.59 g).

mp: 84–85° C.

IR (Nujol): 3250, 2950, 1705 cm$^{-1}$

NMR (DMSO-d$_6$, δ): 1.40 (6H, s), 2.3–2.5 (2H, m), 2.7–2.9 (2H, m), 4.24 (2H, s), 6.18 (1H, t, J=4.6 Hz), 6.8–6.9 (1H, m), 7.1–7.3 (3H, m), 7.6–7.7 (2H, m), 7.9–8.1 (2H, m), 9.31 (1H, s)

(+) APCI MASS: 454 (M+H)$^+$

Elemental Analysis Calcd. for C$_{22}$H$_{22}$F$_3$NO$_4$S: C 58.27, H 4.89, N 3.09 Found: C 58.07, H 5.05, N 3.04

PREPARATION 14

The following compounds were obtained according to a similar manner to that of Preparation 13.

(1) 2-Methyl-2-trifluoromethylsulfonylaminopropyl 3-(6-fluoro-2H-1-benzopyran-4-yl)benzoate IR (Film): 3230, 2970, 1710, 1600, 1580 cm$^{-1}$ NMR (DMSO-d$_6$, δ): 1.41 (6H, s), 4.25 (2H, s), 4.85 (2H, d, J=3.9 Hz), 6.11 (1H, t, J=3–9 Hz), 6.63 (1H, dd, J=3.0, 9.5 Hz), 6.9–7.1 (2H, m), 7.6–7.7 (2H, m), 7.9–8.2 (2H, m), 9.32 (1H, s)

(+) APCI MASS: 474 (M+H)$^+$ (2) 2-Methyl-2-trifluoromethylsulfonylaminopropyl 3-[(4aRS,8aSR)-3,4,4a,5,6,7,8,8a-octahydro-1-naphthyl]benzoate IR (Film): 3230, 2920, 2850, 1700 cm$^{-1}$ NMR (DMSO-d$_6$, δ): 0.5–0.8 (1H, m), 1.0–1.8 (11H, m), 2.1–2.4 (3H, m), 4.23 (2H, s), 5.7–5.8 (1H, m), 7.4–7.6 (2H, m), 7.8–8.0 (2H, m), 9.33 (1H, s)

(+) APCI MASS: 460 (M+H)$^+$ (3) 2-Methyl-2-trifluoromethylsulfonylaminopropyl 3-[spiro[2H-1-benzopyran-2,1'-cyclopentane]-4-yl]benzoate IR (Film): 3230, 2950, 1705, 1600 cm$^{-1}$ NMR (DMSO-d$_6$, δ): 1.41 (6H, s), 1.6–2.2 (8H, m), 4.25 (2H, s), 5.91 (1H, s), 6.8–7.0 (3H, m), 7.1–7.3 (1H, m), 7.6–7.7 (2H, m), 7.9–8.1 (2H, m), 9.31 (1H, s)

(+) APCI MASS: 510 (M+H)$^+$ (4) 2-Methyl-2-trifluoromethylsulfonylaminopropyl 3-(2,2-dimethyl-2H-1-benzopyran-4-yl)benzoate mp: 92–93° C.

IR (Nujol): 3200, 1690, 1600 cm$^{-1}$

NMR (DMSO-d$_6$, δ): 1.42 (6H, s), 1.46 (6H, s), 4.26 (2H, s), 5.83 (1H, s), 6.8–7.0 (3H, m), 7.1–7.3 (1H, m), 7.6–7.7 (2H, m), 7.9–8.1 (2H, m), 9.31 (1H, s)

(+) APCI MASS: 484 (M+H)$^+$

Elemental Analysis Calcd. for C$_{23}$H$_{24}$F$_3$NO$_5$S: C 57.14, H 5.00, N 2.90 Found: C 56.96, H 4.80, N 2.85

(5) 2-Methyl-2-trifluoromethylsulfonylaminopropyl 3-(2H-1-benzopyran-4-yl)benzoate IR (Film): 3230, 2980, 1715, 1600, 1580 cm$^{-1}$ NMR (DMSO-d$_6$, δ): 1.41 (6H, s), 4.26 (2H, s), 4.85 (2H, d, J=3.9 Hz), 6.01 (1H, t, J=3.9 Hz), 6.8–7.0 (3H, m), 7.1–7.3 (1H, m), 7.6–7.7 (2H, m), 7.9–8.1 (2H, m), 9.32 (1H, s)

(+) APCI MASS: 456 (M+H)$^+$ (6) 2-Methyl-2-trifluoromethylsulfonylaminopropyl 3-(1H-inden-3-yl)benzoate IR (Film): 3220, 2980, 2900, 1710, 1600, 1580 cm$^{-1}$ NMR (DMSO-d$_6$, δ): 1.43 (6H, s), 3.5–3.6 (2H, m), 4.29 (2H, s), 6.8–6.9 (1H, m), 7.2–8.3 (8H, m), 9.34 (1H, s)

(+) APCI MASS: 440 (M+H)$^+$ (7) 2-Methyl-2-trifluoromethylsulfonylaminopropyl 3-(6,7-dihydro-5H-benzocyclohepten-9-yl)benzoate IR (Film): 3250, 2950, 2860, 1720, 1700, 1600, 1580 cm$^{-1}$ NMR (DMSO-d$_6$, δ): 1.39 (6H, s), 1.8–2.2 (4H, m), 2.5–2.7 (2H, m), 4.22 (2H, s), 6.56 (1H, t, J=7.2 Hz), 6.8–6.9 (1H, m), 7.2–7.4 (3H, m), 7.5–7.6 (2H, m), 7.85 (1H, s), 7.9–8.0 (1H, m), 9.30 (1H, s)

(+) APCI MASS: 468 (M+H)$^+$ (8) 2-Methyl-2-trifluoromethylsulfonylaminopropyl 3-(benzoxazol-4-yl)benzoate mp: 154–155° C.

IR (Nujol): 3120, 1723, 1195, 750 cm$^{-1}$

NMR (DMSO-d$_6$, δ): 1.45 (6H, s), 4.30 (3H, s), 7.54–7.87 (4H, m), 8.08–8.13 (1H, m), 8.29–8.34 (1H, m), 8.70–8.72 (1H, m), 8.87 (1H, s), 9.36 (1H, s)

(+) APCI MASS: 443 (M+H)$^+$

Elemental Analysis Calcd. for $C_{19}H_{17}F_3N_2$: C 51.58, H 3.87, N 6.33 Found: C 51.34, H 3.79, N 6.14

PREPARATION 15

To a mixture of 3-(3,5-difluorophenyl)benzoic acid (2.3 g) in anhydrous methanol (46 ml) was added concentrated sulfuric acid (2.3 ml). The mixture was heated under reflux for four hours. After cooling to ambient temperature, the mixture was concentrated. Ethyl acetate (200 ml) and water (100 ml) were added and the layers were separated. The organic layer was successively washed with 20% aqueous potassium carbonate solution and brine, dried over magnesium sulfate and evaporated in vacuo. The residue was purified by column chromatography on silica gel with hexane-ethyl acetate (10:1) as an eluent. The fractions containing the object product were collected and evaporated in vacuo to give methyl 3-(3,5-difluorophenyl)benzoate.

mp: 52–54° C.

IR (Nujol): 1720, 1600, 1270, 1120 cm$^{-1}$

NMR (DMSO-d$_6$, δ): 3.91 (3H, s), 7.21–7.32 (1H, m), 7.40–7.52 (2H, m), 7.64 (1H, dd, J=7.7, 7.7 Hz), 8.00 (2H, dd, J=7.7, 1.7 Hz, 8.20 (1H, dd, J=1.7, 1.7 Hz)

(+) APCI MASS: 249 (M+H)$^+$

Elemental Analysis Calcd. for $C_{14}H_{10}F_2O_2$: C 67.74, H 4.06 Found: C 67.51, H 4.06

PREPARATION 16

The following compounds were obtained according to a similar manner to that of Preparation 15.

(1) Methyl 3-[3,5-bis(trifluoromethyl)phenyl]benzoate mp: 78–80° C.

IR (Nujol): 1720, 1280, 1160 cm$^{-1}$

NMR (DMSO-d$_6$, δ): 3.92 (3H, s), 7.69 (1H, dd, J=7.8, 7.8 Hz), 8.04–8.17 (3H, m), 8.32 (1H, dd, J=1.6, 1.6 Hz), 8.37 (2H, s)

(+) APCI MASS: 349 (M+H)$^+$

Elemental Analysis Calcd. for $C_{16}H_{10}F_6O_2$: C 55.19, H 2.89 Found: C 54.82, H 2.75

(2) Methyl 3-(3,5-dimethylphenyl)benzoate

IR (Neat): 1720, 1600, 1250, 1200, 1110 cm$^{-1}$

NMR (DMSO-d$_6$, δ): 2.35 (6H, s), 3.89 (3H, s), 7.04 (1H, s), 7.30 (2H, s), 7.60 (1H, dd, J=7.7, 7.7 Hz), 7.89–7.97 (2H, m), 8.16 (1H, dd, J=1.7, 1.7 Hz)

(+) APCI MASS: 241 (M+H)$^+$ (3) Methyl 3-(2-chlorothiophen-3-yl)benzoate

IR (Neat): 1720, 1580, 1430, 1280 cm$^{-1}$

NMR (DMSO-d$_6$, δ): 3.89 (3H, s), 7.31 (1H, d, J=5.8 Hz), 7.59–7.69 (2H, m), 7.87 (1H, ddd, J=7.9, 1.5, 1.5 Hz), 7.99 (1H, ddd, J=7.9, 1.5, 1.5 Hz), 8.16 (1H, dd, J=1.5, 1.5 Hz)

(+) APCI MASS: 253 (M+H)$^+$

Elemental Analysis Calcd. for $C_{12}H_9ClO_2S$: C 57.03, H 3.59 Found: C 56.84, H 3.17

PREPARATION 17

3-(2,3-Dichlorophenyl)benzoic acid was obtained according to a similar manner to that of Preparation 6, and then the following compound was obtained by treating the compound obtained above according to a similar manner to that of Preparation 15.

Methyl 3-(2,3-dichlorophenyl)benzoate mp: 87.5–89.5° C.

IR (Nujol): 1720, 1310, 1260 cm$^{-1}$

NMR (DMSO-d$_6$, δ): 3.89 (3H, s), 7.39–7.52 (2H, m), 7.61–7.77 (3H, m), 7.98 (1H, dd, J=1.6, 1.6 Hz), 8.04 (1H, ddd, J=7.4, 1.6, 1.6 Hz)

(+) APCI MASS: 281 (M+H)$^+$

Elemental Analysis Calcd. for $C_{14}H_{10}Cl_2O_2$: C 59.81, H 3.59 Found: C 60.16, H 3.61

PREPARATION 18

A mixture of 4,4-dimethyl-2-[3-(4-methoxycarbonyl-2,5-dihydrofuran-3-yl)phenyl]-4,5-dihydrooxazole (1.92 g) and sodium methoxide (0.96 g) in formamide (70 ml) was heated at 100° C. for three hours. The reaction mixture was cooled to room temperature and was poured onto ice-water. The product was extracted with ethyl acetate and the organic layer was washed with water and brine, dried over magnesium sulfate, and evaporated in vacuo. The residue was purified by column chromatography on silica gel eluting with a mixture of chloroform and acetone (5:1). The fractions containing the desired product were collected and evaporated in vacuo to give 2-[3-(4-carbamoyl-2,5-dihydrofuran-3-yl)phenyl]-4,4-dimethyl-4,5-dihydrooxazole.

mp: 120–122° C.

IR (Nujol): 3350, 3150, 1730, 1640, 1240 cm$^{-1}$

NMR (DMSO-d$_6$, δ): 1.29 (6H, s), 4.12 (2H, s), 4.87–4.92 (2H, m), 4.97–5.02 (2H, m), 7.42–7.55 (2H, br s), 7.47 (1H, dd, J=7.8, 7.8 Hz), 7.60 (1H, ddd, J=7.8, 1.6, 1.6 Hz), 7.82 (1H, ddd, J=7.8, 1.6, 1.6 Hz), 7.88 (1H, dd, J=1.6, 1.6 Hz)

(+) APCI MASS: 287 (M+H)$^+$

PREPARATION 19

To a solution of 2-[3-(4-carbamoyl-2,5-dihydrofuran-3-yl)phenyl]-4,4-dimethyl-4,5-dihydrooxazole (0.1 g) in dichloromethane (1 ml) was added dropwise bis (trifluoromethanesulfonic)anhydride (0.0588 ml) at 0° C. and the mixture was stirred at room temperature for two hours. Then water was added to the reaction mixture and the stirring was continued for thirty minutes. The product was extracted with ethyl acetate and the organic layer was washed with brine, dried over magnesium sulfate and evaporated in vacuo. The residue was purified by column chromatography on silica gel eluting with chloroform. The fractions containing the desired product were collected and evaporated in vacuo to give 2-[3-(4-cyano-2,5-dihydrofuran-3-yl)phenyl]-4,4-dimethyl-4,5-dihydrooxazole.

mp: 118–120° C.

IR (Nujol): 2200, 1640 cm$^{-1}$

NMR (DMSO-d$_6$, δ): 1.30 (6H, s), 4.15 (2H, s), 4.92 (2H, t-like, J=4.9 Hz), 5.21 (2H, t-like, J=4.9 Hz), 7.64 (1H, dd, J=7.8, 7.8 Hz), 7.86 (1H, ddd, J=7.8, 1.6, 1.6 Hz), 7.99 (1H, ddd, J=7.8, 1.6, 1.6 Hz), 8.13 (1H, dd, J=1.6, 1.6 Hz)

(+) APCI MASS: 269 (M+H)$^+$

PREPARATION 20

A mixture of methyl 3-(3,5-dimethoxyphenyl)benzoate (0.83 g) and d,l-methionine (9.10 g) in methanesulfonic acid (19.8 ml) was stirred at 40° C. for 10 hours. The mixture was poured onto ice-water and then the product was extracted with ethyl acetate and washed with sodium hydrogencarbonate solution and brine. The organic layer was dried over magnesium sulfate and evaporated in vacuo. The residue was purified by column chromatography on silica gel eluting with a mixture of chloroform and acetone (5:1). The fractions containing the desired product was collected and evaporated in vacuo to give methyl 3-(3,5-dihydroxyphenyl) benzoate.

mp: 148–150° C.

IR (Nujol): 3350, 1700, 1590, 1300, 1260 cm$^{-1}$

NMR (DMSO-d$_6$, δ): 3.89 (3H, s), 6.27 (1H, dd, J=2.1, 2.1 Hz), 6.51 (2H, dd, J=2.1, 2.1 Hz), 7.59 (1H, dd, J=7.8, 7.8 Hz), 7.83 (1H, ddd, J=7.8, 1.6, 1.6 Hz), 7.93 (1H, ddd, J=7.8, 1.6, 1.6 Hz), 8.08 (1H, dd, J=1.6, 1.6 Hz), 9.43 (2H, s)

(+) APCI MASS: 245 (M+H)$^+$

PREPARATION 21

A mixture of 2-[3-(benzofuran-4-yl)phenyl]-4,4-dimethyl-4,5-dihydrooxazole (1.4 g), concentrated sulfuric acid (0.8 ml) and water (1 ml) in methanol (20 ml) was refluxed for 48 hours. After evaporating the solvent, the residue was dissolved in a mixture of ethyl acetate (50 ml) and water (50 ml). The organic layer was successively washed with 10% sodium carbonate aqueous solution, brine and dried over magnesium sulfate. The solvent was evaporated in vacuo and the residue was purified by column chromatography on silica gel eluting with toluene. The fractions containing the desired products were collected and evaporated in vacuo to afford methyl 3-(benzofuran-4-yl)benzoate (0.77 g).

IR (Film): 1720, 1535, 1440, 750 cm$^{-1}$

NMR (DMSO-d$_6$, δ): 3.90 (3H, s), 7.04–7.07 (1H, m), 7.41–7.46 (2H, m), 7.64–7.74 (2H, m), 7.94–8.20 (4H, m)

(+) APCI MASS: 253 (M+H)$^+$

PREPARATION 22

The following compounds were obtained according to a similar manner to that of Preparation 21.

(1) Methyl 3-(4-cyano-2,5-dihydrofuran-3-yl)benzoate
  mp: 99–101° C.
  IR (Nujol): 2200, 1720, 1600 cm$^{-1}$
  NMR (DMSO-d$_6$, δ): 3.90 (3H, s), 4.93 (2H, t-like, J=5.0 Hz), 5.22 (2H, t-like, J=5.0 Hz), 7.71 (1H, dd, J=7.8, 7.8 Hz), 7.95 (1H, ddd, J=7.8, 1.6, 1.6 Hz), 8.09 (1H, ddd, J=7.8, 1.6, 1.6 Hz), 8.30 (1H, dd, J=1.6, 1.6 Hz)
  (+) APCI MASS: 239 (M+H)$^+$ (2) Methyl 3-(4-cyano-2,5-dihydrothiophen-3-yl)benzoate
  mp: 106–108° C.
  IR (Nujol): 2200, 1710, 1430, 1270 cm$^{-1}$
  NMR (DMSO-d$_6$, δ): 3.89 (3H, s), 4.14 (2H, t-like, J=4.4 Hz), 4.41 (2H, t-like, J=4.4 Hz), 7.68 (1H, dd, J=7.8, 7.8 Hz), 7.94 (1H, ddd, J=7.8, 1.8, 1.8 Hz), 8.06 (1H, ddd, J=7.8, 1.8, 1.8 Hz), 8.24 (1H, dd, J=1.8, 1.8 Hz)
  (+) APCI MASS: 246 (M+H)$^+$ (3) Methyl 3-(2-cyano-1-cyclopenten-1-yl)benzoate
  mp: 72–74° C.
  IR (Nujol): 200, 1720, 1290, 1080 cm$^{-1}$
  NMR (DMSO-d$_6$, δ): 2.04 (2H, tt, J=7.5, 7.5 Hz), 2.75–2.86 (2H, m), 2.93–3.03 (2H, m), 3.89 (3H, s), 7.65 (1H, dd, J=7.8, 7.8 Hz), 7.93–8.04 (2H, m), 8.28 (1H, dd, J=1.6, 1.6 Hz)
  (+) APCI MASS: 228 (M+H)$^+$
  Elemental Analysis Calcd. for C$_{14}$H$_{13}$NO$_2$: C 73.99, H 5.77, N 6.16 Found: C 73.81, H 5.68, N 6.10

(4) Methyl 3-(2-methylimidazo[1,2-a]pyridin-8-yl)benzoate
  mp: 102–103° C.
  IR Nujol): 1710, 1290, 1250 cm$^{-1}$
  NMR (DMSO-d$_6$, δ): 2.38 (3H, s), 3.91 (3H, s), 6.95 (1H, dd, J=7.1, 6.9 Hz), 7.46 (1H, dd, J=7.1, 1.1 Hz), 7.66 (1H, dd, J=7.8, 7.8 Hz), 7.80 (1H, s), 8.00 (1H, ddd, J=7.8, 1.3, 1.3 Hz), 8.38 (1H, ddd, J=7.8, 1.3, 1.3 Hz), 8.51 (1H, dd, J=6.9, 1.1 Hz), 8.69 (1H, dd, J=1.3, 1.3 Hz)
  (+) APCI MASS: 267 (M+H)$^+$
  Elemental Analysis Calcd. for C$_{16}$H$_{14}$N$_2$O$_2$: C 72.17, H 5.30, N 10.52 Found: C 71.90, H 5.32, N 10.27

(5) Methyl 3-(5-quinoxalinyl)benzoate
  mp: 114–117° C.
  IR (Nujol): 3400, 1720, 1250 cm$^{-1}$
  NMR (DMSO-d$_6$, δ): 3.89 (3H, s), 7.67 (1H, dd, J=7.7, 7.7 Hz), 7.93–7.99 (3H, m), 8.04 (1H, d, J=7.8 Hz), 8.13–8.20 (1H, m), 8.23 (1H, s), 8.98 (1H, d, J=1.7 Hz), 9.01 (1H, d, J=1.7 Hz)
  (+) APCI MASS: 265 (M+H)$^+$ (6) Methyl 3-(5-isoquinolyl)benzoate
  mp: 104–106° C.
  IR (Nujol): 1720, 1580, 1300, 1240 cm$^{-1}$
  NMR (DMSO-d$_6$, δ): 3.90 (3H, s), 7.61 (1H, d, J=6.0 Hz), 7.69–7.84 (4H, m), 8.05 (1H, s), 8.10 (1H, ddd, J=7.4, 1.6, 1.6 Hz), 8.18–8.26 (1H, m), 8.52 (1H, d, J=6.0 Hz), 9.43 (1H, s)
  (+) APCI MASS: 264 (M+H)$^+$
  Elemental Analysis Calcd. for C$_{17}$H$_{13}$NO$_2$: C 77.55, H 4.98, N 5.32 Found: C 77.13, H 4.89, N 5.27

(7) Metyl 3-(8-quinolyl)benzoate
  mp: 89–91° C.
  IR (Nujol): 1710, 1290, 1250 cm$^{-1}$
  NMR (DMSO-d$_6$, δ): 3.90 (3H, s), 7.57–7.76 (3H, m), 7.83 (1H, dd, J=7.1, 1.6 Hz), 7.92–8.08 (3H, m), 8.26 (1H, dd, J=1.6, 1.6 Hz), 8.47 (1H, dd, J=8.3, 1.8 Hz), 8.94 (1H, dd, J=4.1, 1.8 Hz)
  (+) APCI MASS: 264 (M+H)$^+$ (8) Methyl 3-(2,6-dichlorophenyl)benzoate
  IR (Neat): 1720, 1430, 1290, 1230 cm$^{-1}$
  NMR (DMSO-d$_6$, δ): 3.87 (3H, s), 7.43–7.52 (1H, m), 7.56–7.72 (4H, m), 7.82 (1H, dd, J=1.6, 1.6 Hz), 8.04 (1H, ddd, J=7.5, 1.6, 1.6 Hz)
  (+) APCI MASS: 281 (M+H)$^+$
  Elemental Analysis Calcd. for C$_{14}$H$_{10}$Cl$_2$O$_2$: C 59.81, H 3.59 Found: C 60.01, H 3.66

(9) Methyl 3-(3,5-dimethoxyphenyl)benzoate
  IR (Neat): 1720, 1590, 1270 cm$^{-1}$
  NMR (DMSO-d$_6$, δ): 3.83 (6H, s), 3.90 (3H, s), 6.56 (1H, dd, J=2.1, 2.1 Hz), 6.80 (2H, dd, J=2.1, 2.1 Hz), 7.61 (1H, dd, J=7.8, 7.8 Hz), 7.96 (2H, d, J=7.8 Hz), 8.17 (1H, s)
  (+) APCI MASS: 273 (M+H)$^+$

(10) Methyl 3-(3,5-dichlorophenyl)benzoate
  mp: 103–105° C.
  IR (Nujol): 1710, 1560, 1300 cm$^{-1}$ NMR (DMSO-d$_6$, δ): 3.90 (3H, s), 7.61–7.69 (2H, m), 7.79 (2H, dd, J=1.7, 1.7 Hz), 7.99–8.06 (2H, m), 8.21 (1H, dd, J=1.7, 1.7 Hz)

(+) APCI MASS: 281 (M+H)$^+$

Elemental Analysis Calcd. for C$_{14}$H$_{10}$Cl$_2$O$_2$: C 59.81, H 3.59 Found: C 59.81, H 3.65

(11) Methyl 3-(benzofuran-7-yl)benzoate

IR (Film): 1720, 1435, 1400, 1250, 1030 cm$^{-1}$

NMR (DMSO-d$_6$, δ): 3.91 (3H, s), 7.09 (1H, d, J=2.2 Hz), 7.40 (1H, dd, J=7.6, 7.6 Hz), 7.58 (1H, dd, J=7.6, 1.2 Hz), 7.65–7.75 (2H, m), 7.98–8.20 (3H, m), 8.46–8.47 (1H, m)

(+) APCI MASS: 253 (M+H)$^+$

(12) Methyl 3-(2-methoxymethyl-3,4-dihydro-1-naphthyl)benzoate

IR (Film): 2930, 2820, 1720, 1600, 1580 cm$^{-1}$

NMR (DMSO-d$_6$, δ): 2.4–2.6 (2H, m), 2.8–3.0 (2H, m), 3.11 (3H, s), 3.78 (2H, s), 3.85 (3H, s), 6.42 (1H, d, J=7.4 Hz), 7.0–7.3 (3H, m), 7.4–7.7 (3H, m), 7.9–8.1 (1H, m)

PREPARATION 23

A solution of methyl 3-(furan-3-yl)benzoate (1.0 g) in acetic acid (5 ml) was stirred at 110° C., and to this was slowly added N-chlorosuccinimide (0.66 g). The mixture was heated at 110° C. for 1.5 hours and then cooled to room temperature. The reaction mixture was poured onto water and the product was extracted with ethyl acetate, washed successively with water, hydrochloric acid, and brine. The organic layer was dried over magnesium sulfate and evaporated in vacuo. The residue was purified by column chromatography on silica gel eluting with a mixture of hexane-:toluene (2:1) to afford methyl 3-(2-chlorofuran-3-yl)benzoate (0.24 g).

mp: 36–37° C.

IR (Nujol): 1720, 1600, 1350, 1300, 1250 cm$^{-1}$

NMR (DMSO-d$_6$, δ): 3.89 (3H, s), 7.12 (1H, d, J=2.2 Hz), 7.63 (1H, dd, J=7.7, 7.7 Hz), 7.85 (1H, d, J=2.2 Hz), 7.94 (2H, ddd, J=7.7, 1.7, 1.7 Hz), 8.25 (1H, dd, J=1.7, 1.7 Hz)

(+) APCI MASS (m/z): 237 (M+H)$^+$

Elemental Analysis Calcd. for C$_{12}$H$_9$ClO$_3$: C 60.90, H 3.83 Found: C 61.32, H 3.62

PREPARATION 24

N,N-dimethylformamide (1.7 ml) was stirred at 0° C. and to this was added dropwise phosphorus oxychloride (0.51 ml). The mixture was stirred for 30 minutes and was added a solution of methyl 3-(furan-3-yl)benzoate (1 g) in N,N-dimethylformamide (0.6 ml), and then was stirred at room temperature overnight. The reaction mixture was poured onto ice/water and then adjusted to pH 8 with an aqueous potassium carbonate solution. The product was extracted with ethyl acetate-tetrahydrofuran (1:1, 2×100 ml) and the extracts were combined, washed successively with water and brine, dried over magnesium sulfate and evaporated in vacuo. The residue was purified by column chromatography on silica gel eluting with a mixture of hexane:ethyl acetate (5:1) to afford methyl 3-(2-formylfuran-3-yl)benzoate (0.75 g).

mp: 93–95° C.

IR (Nujol): 1720, 1660, 1300, 1250 cm$^{-1}$

NMR (DMSO-d$_6$, δ): 3.90 (3H, s), 7.16 (1H, d, J=1.8 Hz), 7.66 (1H, dd, J=7.8, 7.8 Hz), 8.00–8.07 (2H, m), 8.20 (1H, d, J=1.8 Hz), 8.24 (1H, dd, J=1.7, 1.7 Hz), 9.72 (1H, s)

(+) APCI MASS (m/z): 231 (M+H)$^+$

Elemental Analysis Calcd. for C$_{13}$H$_{10}$O$_4$: C 67.82, H 4.38 Found: C 67.41, H 4.33

PREPARATION 25

The following compound was obtained according to a similar manner to that of Preparation 24.

Methyl 3-(2-formylthiophen-3-yl)benzoate mp: 101–103° C.

IR (Nujol): 1720, 1640, 1300, 1250 cm$^{-1}$

NMR (DMSO-d$_6$, δ): 3.90 (3H, s), 7.49 (1H, d, J=5.0 Hz), 7.68 (1H, dd, J=7.6, 7.6 Hz), 7.93 (1H, d, J=7.6 Hz), 8.07 (1H, d, J=7.6 Hz), 8.09 (1H, s), 8.22 (1H, d, J=5.0 Hz), 9.80 (1H, s)

Elemental Analysis Calcd. for C$_{13}$H$_{10}$O$_3$S: C 63.40, H 4.09 Found: C 63.41, H 4.02

(+) APCI MASS (m/z): 247 (M+H)$^+$

PREPARATION 26

(1) To a solution of methyl 3-(2-formylfuran-3-yl)benzoate (1 g) in dry dichloromethane (20 ml) was added dropwise at 0° C. a solution of diethylaminosulfur trifluoride (0.689 ml) in dry dichloromethane (20 ml). The mixture was stirred at room temperature overnight and then poured onto water (20 ml). The layers were separated and the organic layer was washed with water, dried over magnesium sulfate and evaporated in vacuo. The residue was purified by column chromatography on silica gel eluting with a mixture of hexane:ethyl acetate (5:1) to afford methyl 3-(2-difluoromethylfuran-3-yl)benzoate (0.29 g).

mp: 55–56° C.

IR (Nujol): 1710, 1410, 1280, 1250 cm$^{-1}$

NMR (DMSO-d$_6$, δ): 3.89 (3H, s), 7.00 (1H, d, J=1.6 Hz), 7.17 (1H, t, J=51.9 Hz), 7.65 (1H, dd, J=7.8, 7.8 Hz), 7.76 (1H, ddd, J=7.8, 1.6, 1.6 Hz), 7.97–8.03 (3H, m)

Elemental Analysis Calcd. for C$_{13}$H$_{10}$F$_2$O$_3$: C 61.91, H 4.00 Found: C 61.45, H 3.83

The following compound was obtained according to a similar manner to that of Preparation 26-(1).

(2) Methyl 3-(2-difluoromethylthiophen-3-yl)benzoate mp: 84–85° C.

IR (Nujol): 1710, 1300, 1250 cm$^{-1}$

NMR (DMSO-d$_6$, δ): 3.89 (3H, s), 7.19 (1H, t, J=54.2 Hz), 7.33–7.38 (1H, m), 7.66 (1H, dd, J=7.6, 7.6 Hz), 7.75 (1H, d, J=7.6 Hz), 7.93 (1H, d, J=5.1 Hz), 8.00 (1H, s), 8.02 (1H, d, J=7.6 Hz)

Elemental Analysis Calcd. for C$_{13}$H$_{10}$F$_2$O$_2$S: C 58.20, H 3.76 Found: C 58.60, H 3.45

PREPARATION 27

A mixture of methyl 3-(thiophen-3-yl)benzoate (2 g) in acetic anhydride (2 g) was heated to 75° C. The oil bath was removed and phosphoric acid (0.063 ml) was added thereto. The reaction mixture was stirred at 140° C. for 2 hours and cooled to room temperature. The mixture was diluted with ethyl acetate and washed successively with water, an aqueous sodium carbonate solution (×2) and brine. The organic layer was dried over magnesium sulfate and evaporated in vacuo. The residue was purified by column chromatography on silica gel eluting with a mixture of hexane:ethyl acetate (10:1) to afford methyl 3-(2-acetylthiophen-3-yl)benzoate (1.44 g).

mp: 68–70° C.

IR (Nujol): 1710, 1640 cm$^{-1}$

NMR (DMSO-d$_6$, δ): 2.19 (3H, s), 3.88 (3H, s), 7.24 (1H, d, J=4.9 Hz), 7.61 (1H, dd, J=7.6, 7.6 Hz), 7.74 (1H, d, J=7.6 Hz), 7.97–8.03 (3H, m)

(+) APCI MASS (m/z): 261 (M+H)⁺

Elemental Analysis Calcd. for $C_{14}H_{12}O_3S$: C 64.60, H 4.65 Found: C 64.71, H 4.53

PREPARATION 28

To chlorosulfonic acid (18 ml, cooled to −5° C.) was added methyl 3-(thiophen-3-yl)benzoate (3 g) with stirring over 15 minutes. The reaction mixture was stirred at −5° C.~−0° C. for 30 minutes and slowly poured onto ice/water. The product was extracted with ethyl acetate, washed with water and brine, dried over magnesium sulfate and evaporated in vacuo. The residue was dissolved in acetone and was added to a mixture of ice aqueous ammonia (75 ml)/acetone (75 ml). The reaction mixture was allowed to warm to room temperature and the solvent was partially removed under vacuum. The resulting basic aqueous layer was then acidified with 6N hydrochloric acid and the product was extracted with ethyl acetate, washed with brine, dried over magnesium sulfate and evaporated in vacuo. The residue was purified by column chromatography on silica gel eluting with a mixture of chloroform:methanol (50:1) to afford methyl 3-(2-sulfamoylthiophen- 3-yl)benzoate (1.97 g) (A) and methyl 3-(5-sulfamoylthiophen-3-yl)benzoate (0.65 g) (B).

(A) mp: 169–170° C.

IR (Nujol): 3300, 3200, 1690, 1350, 1300 cm⁻¹

NMR (DMSO-d₆, δ): 3.87 (3H, s), 7.23 (1H, d, J=5.2 Hz), 7.59 (1H, dd, J=7.8, 7.8 Hz), 7.73 (2H, s), 7.86 (1H, d, J=5.2 Hz), 7.87 (1H, ddd, J=7.8, 1.5, 1.5 Hz), 7.98 (1H, ddd, J=7.8, 1.5, 1.5 Hz), 8.13 (1H, dd, J=1.5, 1.5 Hz)

(+) APCI MASS (m/z): 298 (M+H)⁺

Elemental Analysis Calcd. for $C_{12}H_{11}NO_4S_2$: C 48.47, H 3.73, N 4.71 Found: C 48.95, H 3.58, N 4.41

(B) mp: 140–141° C.

IR (Nujol): 3350, 3250, 1710, 1290 cm⁻¹

NMR (DMSO-d₆, δ): 3.90 (3H, s), 7.62 (1H, dd, J=7.8, 7.8 Hz), 7.75 (2H, s), 7.94 (1H, d, J=7.8 Hz), 8.01 (1H, d, J=1.7 Hz), 8.03 (1H, d, J=7.8 Hz), 8.22 (1H, dd, J=1.6, 1.6 Hz), 8.29 (1H, d, J=1.7 Hz)

(+) APCI MASS (m/z) 298 (M+H)⁺

PREPARATION 29

The following compounds were obtained according to a similar manner to that of Preparation 11.

(1) 2-[3-(3-Chlorothiophen-2-yl)phenyl]-4,4-dimethyl-4,5-dihydrooxazole

IR (Nujol): 1170, 1045 cm⁻¹

NMR (DMSO-d₆, δ): 1.30 (6H, s), 4.14 (2H, s), 7.21 (1H, d, J=5.4 Hz), 7.60 (1H, dd, J=7.8, 7.8 Hz), 7.76 (1H, d, J=5.4 Hz), 7.8–7.9 (2H, m), 8.10 (1H, s)

(+) APCI MASS: 292 (M+H)⁺

(2) 2-[3-(5-Chlorothiophen-3-yl)phenyl]-4,4-dimethyl-4,5-dihydrooxazole

IR (Neat): 3350, 3100, 1640, 1600, 1450, 1350, 1310 cm⁻¹

NMR (DMSO-d₆, δ): 1.30 (6H, s), 4.13 (2H, s), 7.52 (1H, dd, J=7.8, 7.8 Hz), 7.67 (1H, d, J=1.8 Hz), 7.79 (1H, d, J=7.8 Hz), 7.86 (1H, d, J=7.8 Hz), 7.88 (1H, d, J=1.8 Hz), 8.08 (1H, s)

(+) APCI MASS (m/z): 292 (M+H)⁺

(3) 2-[3-(2,5-Dichlorothiophen-3-yl)phenyl]-4,4-dimethyl-4,5-dihydrooxazole

IR (Neat): 2950, 1650, 1600, 1450, 1350, 1300, 1200 cm⁻¹

NMR (DMSO-d₆, δ): 1.30 (6H, s), 4.13 (2H, s), 7.44 (1H, s), 7.58 (1H, dd, J=7.8, 7.8 Hz), 7.73 (1H, ddd, J=7.8, 1.6, 1.6 Hz), 7.89 (1H, ddd, J=7.8, 1.6, 1.6 Hz), 8.02 (1H, dd, J=1.6, 1.6 Hz)

(+) APCI MASS (m/z): 326 (M+H)⁺

Elemental Analysis Calcd. for $C_{15}H_{13}Cl_2NOS$: C 55.22, H 4.02, N 4.29 Found: C 55.13, H 4.26, N 3.98

PREPARATION 30

The following compounds were obtained according to a similar manner to that of Preparation 21.

(1) Methyl 3-(3-chlorothiophen-2-yl)benzoate mp: 46–47° C.

IR (Nujol): 1720, 1110, 885 cm⁻¹

NMR (DMSO-d₆, δ): 3.90 (3H, s), 7.23 (1H, d, J=5.4 Hz), 7.66 (1H, dd, J=7.8, 7.8 Hz), 7.79 (1H, d, J=5.4 Hz), 7.92 (1H, d, J=7.8 Hz), 8.00 (1H, d, J=7.8 Hz), 8.20 (1H, s)

Elemental Analysis Calcd. for $C_{12}H_9ClO_2S$: C 57.03, H 3.59 Found: C 57.40, H 3.67

(2) Methyl 3-(5-chlorothiophen-3-yl)benzoate

IR (Neat): 1720, 1580, 1440, 1280, 1220 cm⁻¹

NMR (DMSO-d₆, δ): 3.89 (3H, s), 7.58 (1H, dd, J=7.8, 7.8 Hz), 7.70 (1H, d, J=1.7 Hz), 7.88–7.92 (2H, m), 7.98 (1H, d, J=7.8 Hz), 8.21 (1H, s)

(+) APCI MASS (m/z): 253 (M+H)⁺

(3) Methyl 3-(2,5-dichlorothiophen-3-yl)benzoate mp: 72–73° C.

IR (Nujol): 1730, 1280, 1260, 1210 cm⁻¹

NMR (DMSO-d₆, δ): 3.89 (3H, s), 7.46 (1H, s), 7.65 (1H, dd, J=7.8, 7.8 Hz), 7.86 (1H, ddd, J=7.8, 1.6, 1.6 Hz), 8.00 (1H, ddd, J=7.8, 1.6, 1.6 Hz), 8.14 (1H, dd, J=1.6, 1.6 Hz)

(+) APCI MASS (m/z) 287 (M+H)⁺

Elemental Analysis Calcd. for $C_{12}H_8Cl_2O_2S$: C 50.19, H 2.81 Found: C 50.38, H 2.62

PREPARATION 31

The following compounds were obtained according to a similar manner to that of Preparation 4.

(1) (5-Methylthiophen-2-yl)dihydroxyborane mp: 170–171° C.

IR (Nujol): 3180 cm⁻¹

NMR (DMSO-d₆, δ): 2.45 (3H, s), 6.83 (1H, d, J=3.3 Hz), 7.45 (1H, d, J=3.3 Hz), 8.03 (2H, s)

(2) (3-Methylthiophen-2-yl)dihydroxyborane mp: >250° C.

IR (Nujol): 3170 cm⁻¹

NMR (DMSO-d₆, δ): 2.51 (3H, s), 6.98 (1H, d, J=4.6 Hz), 7.55 (1H, d, J=4.6 Hz)

(3) (2-Methylthiophen-3-yl)dihydroxyborane mp: 188–192° C.

IR (Nujol): 1525 cm⁻¹

NMR (DMSO-d₆, δ): 2.52 (3H, s), 7.14 (1H, d, J=5.1 Hz), 7.23 (1H, d, J=5.1 Hz)

(4) (4-Methylthiophen-3-yl)dihydroxyborane mp: 172–175° C.

IR (Nujol): 3200 cm⁻¹

NMR (DMSO-d₆, δ): 2.32 (3H, s), 7.01–7.06 (1H, m), 7.78–7.85 (1H, m), 7.88 (2H, s)

PREPARATION 32

The following compounds were obtained according to a similar manner to that of Preparation 6.

(1) 3-(5-Methylthiophen-2-yl)benzoic acid mp: 159–160° C.

IR (Nujol): 1670 cm⁻¹

NMR (DMSO-d₆, δ): 2.48 (3H, s), 6.86 (1H, d, J=3.3 Hz), 7.40 (1H, d, J=3.3 Hz), 7.52 (1H, dd, J=7.7, 7.7 Hz), 7.78–7.88 (2H, m), 8.07 (1H, s), 13.14 (1H, s)

(2) 3-(3-Methylthiophen-2-yl)benzoic acid
  mp: 174–176° C.
  IR (Nujol): 1677 cm$^{-1}$
  NMR (DMSO-d$_6$, δ): 2.31 (3H, s), 7.04 (1H, d, J=5.1 Hz), 7.52 (1H, d, J=5.1 Hz), 7.59 (1H, dd, J=7.7, 7.7 Hz), 7.74 (1H, d, J=7.7 Hz), 7.92 (1H, d, J=7.7 Hz), 7.99 (1H, s), 13.16 (1H, s)
(3) 3-(2-Methylthiophen-3-yl)benzoic acid
  mp: 151–153° C.
  IR (Nujol): 1680 cm$^{-1}$
  NMR (DMSO-d$_6$, δ): 2.49 (3H, s), 7.16 (1H, d, J=5.3 Hz), 7.39 (1H, d, J=5.3 Hz), 7.57 (1H, dd, J=7.6, 7.6 Hz), 7.65–7.74 (1H, m), 7.86–7.98 (2H, m), 13.07 (1H, s)
(4) 3-(4-Methylthiophen-3-yl)benzoic acid
  mp: 142–143° C.
  IR (Nujol): 1680 cm$^{-1}$
  NMR (DMSO-d$_6$, δ): 2.24 (3H, s), 7.30–7.34 (1H, m), 7.51–7.62 (2H, m), 7.65–7.74 (1H, m), 7.87–7.98 (2H, m), 13.06 (1H, s)
(5) Methyl 3-(2-chlorothiophen-3-yl)-5-hydroxymethylbenzoate
  IR (Neat): 3350, 1700, 1600 cm$^{-1}$
  NMR (DMSO-d$_6$, δ): 3.89 (3H, s), 4.63 (2H, d, J=5.8 Hz), 5.43 (1H, t, J=5.8 Hz), 7.28 (1H, d, J=5.8 Hz), 7.60 (1H, d, J=5.8 Hz), 7.78 (1H, s), 7.96 (1H, s), 8.02 (1H, s)
  (+) APCI MASS (m/z): 283 (M+H)$^+$
  Elemental Analysis Calcd. for C$_{13}$H$_{11}$ClO$_3$S: C 55.22, H 3.92 Found: C 55.11, H 3.87
(6) Methyl 3-(2-chlorothiophen-3-yl)-5-methoxycarbonylbenzoate
  mp: 153–155° C.
  IR (Nujol): 1720, 1320, 1250 cm$^{-1}$
  NMR (DMSO-d$_6$, δ): 3.93 (6H, s), 7.38 (1H, d, J=5.8 Hz), 7.64 (1H, d, J=5.8 Hz), 8.37 (2H, dd, J=1.6, 1.6 Hz), 8.47 (1H, dd, J=1.6, 1.6 Hz)
  (+) APCI MASS (m/z): 311 (M+H)$^+$
  Elemental Analysis Calcd. for C$_{14}$H$_{11}$ClO$_4$S: C 54.11, H 3.57 Found: C 54.56, H 3.35
(7) Methyl 3-(5-chlorothiophen-2-yl)benzoate
  mp: 46–47° C.
  IR (Nujol): 1720, 1230, 1105, 995 cm$^{-1}$
  NMR (DMSO-d$_6$, δ): 3.89 (3H, s), 7.19 (1H, d, J=4.0 Hz), 7.51 (1H, d, J=4.0 Hz), 7.58 (1H, dd, J=8.0, 8.0 Hz), 7.8–7.93 (2H, m), 8.08 (1H, dd, J=1.6, 1.6 Hz)

PREPARATION 33

The following compounds were obtained according to a similar manner to that of Preparation 15.
(1) Methyl 3-(5-methylthiophen-2-yl)benzoate
  IR (Film): 1720 cm$^{-1}$
  NMR (DMSO-d$_6$, δ): 2.49 (3H, s), 3.89 (3H, s), 6.86 (1H, d, J=3.5 Hz), 7.42 (1H, d, J=3.5 Hz), 7.55 (1H, dd, J=7.8, 7.8 Hz), 7.81–7.92 (2H, m), 8.08 (1H, s)
  (+) APCI MASS: 233 (M+H)$^+$
(2) Methyl 3-(3-methylthiophen-2-yl)benzoate
  IR (Film): 1720 cm$^{-1}$
  NMR (DMSO-d$_6$, δ): 2.31 (3H, s), 3.89 (3H, s), 7.04 (1H, d, J=5.1 Hz), 7.53 (1H, d, J=5.1 Hz), 7.62 (1H, dd, J=7.7, 7.7 Hz), 7.77 (1H, d, J=7.7 Hz), 7.94 (1H, d, J=7.7 Hz), 8.00 (1H, s)
  (+) APCI MASS: 233 (M+H)$^+$
(3) Methyl 3-(2-methylthiophen-3-yl)benzoate
  IR (Film): 1720 cm$^{-1}$
  NMR (DMSO-d$_6$, δ): 2.48 (3H, s), 3.88 (3H, s), 7.17 (1H, d, J=5.3 Hz), 7.40 (1H, d, J=5.3 Hz), 7.60 (1H, dd, J=7.6, 7.6 Hz), 7.68–7.77 (1H, m), 7.88–7.99 (2H, m)
  (+) APCI MASS: 233 (M+H)$^+$
(4) Methyl 3-(4-methylthiophen-3-yl)benzoate
  IR (Film): 1720 cm$^{-1}$
  NMR (DMSO-d$_6$, δ): 2.24 (3H, s), 3.88 (3H, s), 7.30–7.35 (1H, m), 7.54–7.64 (2H, m), 7.69–7.77 (1H, m), 7.90–7.98 (2H, m)
  (+) APCI MASS: 233 (M+H)$^+$

PREPARATION 34

A mixture of 2-carboxy-4-iodobenzo[b]thiophene (2 g) and copper powder (0.05 g) in quinoline (10 ml) was heated at 200° C. for 2 hours. The reaction mixture was cooled to room temperature and diluted with ethyl acetate (50 ml) and ether (50 ml). The mixture was washed with 5% hydrochloric acid solution (3 times) and brine, dried over magnesium sulfate and evaporated in vacuo. The residue was purified by column chromatography on silica gel eluting with toluene to afford 4-iodobenzo[b]thiophene (1.55 g).

IR (Neat): 3100, 1530, 1430, 1400, 1200 cm$^{-1}$

NMR (DMSO-d$_6$, δ): 7.14 (1H, dd, J=7.8, 7.8 Hz), 7.38 (1H, d, J=5.0 Hz), 7.83 (1H, d, J=7.8 Hz), 7.92 (1H, d, J=5.6 Hz), 8.06 (1H, d, J=7.8 Hz)

PREPARATION 35

To a solution of 2-hydroxy-6-trimethylsilylbenzaldehyde (8.1 g) in carbon tetrachloride (160 ml) was added bromine (2.15 ml) dropwise at 0° C., and the mixture was stirred at room temperature overnight. To the mixture was added aqueous sodium hydrogencarbonate solution, and the layers were separated. The aqueous layer was extracted with dichloromethane and the organic layers were combined, washed with sodium thiosulfate solution, dried over magnesium sulfate and evaporated in vacuo. The residue was purified by column chromatography on silica gel eluting with a mixture of hexane and toluene (4:1) to afford 6-bromo-2-hydroxybenzaldehyde (4.74 g).

IR (Neat): 3050, 2850, 1650, 1430, 1270 cm$^{-1}$

NMR (DMSO-d$_6$, δ): 7.04 (1H, dd, J=7.8, 7.8 Hz), 7.80 (1H, dd, J=7.8, 1.6 Hz), 7.90 (1H, dd, J=7.8, 1.6 Hz), 10.09 (1H, s), 11.32 (1H, s)

Elemental Analysis Calcd. for C$_7$H$_5$BrO$_2$: C 41.83, H 2.51 Found: C 42.21, H 2.23

PREPARATION 36

A mixture of 6-bromo-2-hydroxybenzaldehyde (4.48 g), ethyl chloroacetate (3.55 g) and powdered potassium carbonate (6.16 g) in N,N-dimethylformamide (56 ml) was stirred at 120° C. for one hour. Insoluble materials were filtered off and the solvent was removed under reduced pressure. Ethyl acetate and water were added to the residue, and the mixture was acidified by hydrochloric acid solution. The layers were separated and the organic layer was washed with water and brine, dried over magnesium sulfate and evaporated in vacuo. The residue was purified by column chromatography on silica gel eluting with a mixture of hexane and toluene (1:1) to afford 4-bromo-2-ethoxycarbonylbenzofuran (4.20 g).

IR (Neat): 1720, 1570, 1280 cm$^{-1}$

NMR (DMSO-d$_6$, δ): 1.36 (3H, t, J=7.1 Hz), 4.40 (2H, q, J=7.1 Hz), 7.33 (1H, dd, J=7.8, 7.8 Hz), 7.78 (1H, d, J=7.8 Hz), 7.83 (1H, d, J=7.8 Hz), 7.88 (1H, s)

(+) APCI MASS: 269, 271 (M+H)$^+$

PREPARATION 37

To a solution of 4-bromo-2-ethoxycarbonylbenzo[b]furan (0.5 g) in tetrahydrofuran (5 ml) was slowly added sodium borohydride (0.21 g) at room temperature. After 5 minutes, methanol (0.5 ml) was added thereto dropwise. The reaction mixture was stirred at room temperature for one hour and then ethyl acetate and water were added thereto. The mixture was adjusted to pH 5, and the layers were separated. The organic layer was washed with water and brine, dried over magnesium sulfate and evaporated to afford 4-bromo-2-hydroxymethylbenzofuran (0.36 g).

mp: 86–88° C.

IR (Nujol): 3150 (br), 1420, 1270, 1230 cm$^{-1}$

NMR (DMSO-d$_6$, δ): 4.63 (2H, s), 4.95 (1H, br s), 6.93 (1H, s), 7.18 (1H, dd, J=7.8, 7.8 Hz), 7.51 (1H, d, J=7.8 Hz), 7.62 (1H, d, J=7.8 Hz)

Elemental Analysis Calcd. for C$_9$H$_7$BrO$_2$: C 47.61, H 3.11 Found: C 47.65, H 2.89

PREPARATION 38

A mixture of 4-bromo-2-hydroxymethylbenzofuran (0.3 g) and manganese dioxide (0.75 g) in ethyl acetate (3 ml) was heated to reflux for 4 hours. Manganese dioxide was removed by filtration and washed with ethyl acetate. Ethyl acetate was removed under reduced pressure and the residue was purified by column chromatography on silica gel eluting with a mixture of hexane and ethyl acetate (5:1) to give 4-bromo-2-formylbenzofuran (0.24 g).

mp: 93–94° C.

IR (Nujol): 1660, 1280, 1110 cm$^{-1}$

NMR (DMSO-d$_6$, δ): 7.36 (1H, dd, J=7.8, 7.8 Hz), 7.84 (1H, d, J=7.8 Hz), 7.93 (1H, d, J=7.8 Hz), 8.11 (1H, s), 9.92 (1H, s)

(+) APCI MASS: 225, 227 (M+H)$^+$

Elemental Analysis Calcd. for C$_9$H$_5$BrO$_2$: C 48.04, H 2.24 Found: C 47.85, H 2.06

PREPARATION 39

To a mixture of phosphorus oxychloride (3 g) and N-methylformanilide (3 g) was added a solution of methyl 3-(benzofuran-3-yl)benzoate (3 g) in N-methylformamide (1.5 g) at room temperature. The mixture was stirred overnight at room temperature and was poured onto aqueous sodium acetate solution. The product was extracted with ethyl acetate and the organic layer was washed with hydrochloric acid solution, water and brine. The layer was dried over magnesium sulfate and evaporated in vacuo. The residue was purified by column chromatography on silica gel eluting with a mixture of hexane and ethyl acetate (5:1) to afford methyl 3-(2-formylbenzofuran-3-yl)benzoate (2.39 g).

mp: 133–134° C.

IR (Nujol): 1730, 1670 cm$^{-1}$

NMR (DMSO-d$_6$, δ): 3.91 (3H, s), 7.48 (1H, dd, J=7.9, 7.9 Hz), 7.65–7.87 .(4H, m), 8.07–8.17 (2H, m), 8.28 (1H, dd, J=1.6, –1.6 Hz), 9.82 (1H, s)

(+) APCI MASS: 281 (M+H)$^+$

Elemental Analysis Calcd. for C$_{17}$H$_{12}$O$_4$: C 72.85, H 4.32 Found: C 72.54, H 4.03

PREPARATION 40

To a suspension of sodium hydride (0.20 g) in anhydrous toluene (23 ml) was added a hot solution of methyl 3-(indol-4-yl)benzoate (1.16 g) in toluene (5.8 ml). Since a sodium salt did not form, N,N-dimethylformamide (0.5 ml) was introduced. An evolution of gas occurred with the formation of the orange sodium salt of the indole. After being stirred for 20 minutes methyl iodide was added thereto and the mixture was stirred at 60° C. for four hours. Then the sodium iodide was filtered off and washed with toluene. The filtrate was concentrated under reduced pressure and the residue was purified by column chromatography on silica gel eluting with a mixture of hexane and acetone (20:1) to afford methyl 3-(1-methylindol-4-yl)benzoate (0.35 g).

mp: 91–93° C.

IR (Nujol): 1710, 1250, 1210 cm$^{-1}$

NMR (DMSO-d$_6$, δ): 3.85 (3H, s), 3.90 (3H, s), 6.52 (1H, d, J=3.1 Hz), 7.17 (1H, d, J=7.3 Hz), 7.29 (1H, dd, J=7.3, 7.3 Hz), 7.43 (1H, d, J=3.1 Hz), 7.50 (1H, d, J=7.3 Hz), 7.66 (1H, dd, J=7.7, 7.7 Hz), 7.94 (1H, d, J=7.7 Hz), 7.98 (1H, d, J=7.7 Hz), 8.25 (1H, dd, J=1.6, 1.6 Hz)

(+) APCI MASS: 266 (M+H)$^+$

PREPARATION 41

A mixture of dimethyl 5-(2,5-dichlorothiophen-3-yl)isophthalate (1.70 g) and potassium hydroxide (0.28 g) in methanol (50 ml) was heated to reflux for 48 hours. After being cooled to room temperature, the solvent was removed under reduced pressure. The residue was dissolved in water and was acidified with hydrochloric acid solution. The product was extracted with ethyl acetate and the organic layer was washed with brine, dried over magnesium sulfate and evaporated in vacuo. The residue was purified by column chromatography on silica gel eluting with a mixture of chloroform and methanol (10:1) to afford 3-methoxycarbonyl-5-(2,5-dichlorothiophen-3-yl)benzoic acid (1.43 g).

mp: 205–207° C.

IR (Nujol): 1720, 1700, 1540, 1270 cm$^{-1}$

NMR (DMSO-d$_6$, δ): 3.91 (3H, s), 7.49 (1H, s), 8.24 (1H, dd, J=1.7, 1.7 Hz), 8.36 (1H, dd, J=1.7, 1.7 Hz), 8.51 (1H, dd, J=1.7, 1.7 Hz)

(–) APCI MASS: 329 (M–H)$^-$

PREPARATION 42

To a mixture of 3-methoxycarbonyl-5-(2,5-dichlorothiophen-3-yl)benzoic acid (0.7 g), N,N-dimethylethylenediamine (0.186 g) and 1-hydroxybenzotriazole (0.314 g) in dichloromethane (25 ml) was added 1-ethyl-3-(3-dimethylaminopropyl)carbodiimide (0.446 g) under ice cooling, and the solution was stirred for 7 hours at room temperature. After evaporating the solvent, the residue was dissolved in a mixture of ethyl acetate and saturated aqueous sodium hydrogencarbonate solution with stirring. The organic layer was successively washed with water and brine, dried over magnesium sulfate and evaporated in vacuo. The residue was purified by column chromatography on silica gel eluting with a mixture of chloroform and methanol (20:1). The eluted fractions containing the desired product were collected and evaporated in vacuo to afford methyl 5-(2,5-dichlorothiophen-3-yl)-3-[(2-dimethylaminoethyl)carbamoyl]benzoate (0.57 g).

IR (Neat): 3300, 2950, 1720, 1640, 1530, 1440 cm$^{-1}$

NMR (DMSO-d$_6$, δ): 2.19 (6H, s), 2.42 (2H, t, J=6.8 Hz), 3.34–3.44 (2H, m), 3.92 (3H, s), 7.53 (1H, s), 8.27 (2H, dd, J=1.6, 1.6 Hz), 8.45 (1H, dd, J=1.6, 1.6 Hz), 8.72 (1H, t, J=5.6 Hz)

(+) APCI MASS: 401 (M+H)$^+$

PREPARATION 43

Methanol (20 ml) was added dropwise to a mixture of dimethyl 5-iodoisophthalate (20.0 g) and sodium borohydride (2.4 g) in tetrahydrofuran (200 ml) for 15 minutes at 45–50° C., and the mixture was stirred for 1 hour at same temperature. The reaction mixture was added to a mixture of ethyl acetate and water, and the separated organic layer was washed with brine, dried over magnesium sulfate and evaporated in vacuo. The residue was purified by column chromatography on silica gel with chloroform-methanol (19:1, V/V) as an eluent. The fractions containing the desired product were collected and evaporated in vacuo to give methyl 5-hydroxymethyl-3-iodobenzoate (15.11 g).

mp: 44–46° C.

IR (Nujol): 1725 cm$^{-1}$

NMR (DMSO-d$_6$, δ): 3.86 (3H, s), 4.54 (2H, d, J=5.8 Hz), 5.45 (1H, t, J=5.8 Hz), 7.90–7.97 (2H, m), 8.10 (1H, s)

PREPARATION 44

The mixture of methyl 5-hydroxymethyl-3-iodobenzoate (5.0 g) and manganese dioxide (30.0 g) in ethyl acetate (50.0 ml) was heated under reflux for 4 hours. The magnganese dioxide was removed by filtration and the filtrate was evaporated in vacuo to give methyl 5-formyl-3-iodobenzoate (2.77 g).

mp: 72–74° C.

IR (Nujol): 1718, 1684 cm$^{-1}$

NMR (DMSO-d$_6$, δ): 3.91 (3H, s), 8.40 (1H, s), 8.47 (2H, s), 10.02 (1H, s)

PREPARATION 45

The mixture of methyl 5-formyl-3-iodobenzoate (2.5 g), malonic acid (1.8 g) and piperidine (0.2 ml) in pyridine (25 ml) was stirred for 3 hours at 100° C. The mixture was added to water and adjusted to pH 2 with 6N-hydrochloric acid. The isolated precipitate was collected by filtration to give methyl 5-[(E)-2-carboxyethenyl]-3-iodobenzoate (2.4 g)

mp: 205–207° C.

IR (Nujol): 1720, 1680, 1628 cm$^{-1}$

NMR (DMSO-d$_6$, δ): 3.88 (3H, s), 6.67 (1H, d, J=16.1 Hz), 7.59 (1H, d, J=16.1 Hz), 8.19 (1H, s), 8.22 (1H, s), 8.33 (1H, s), 12.58 (1H, s)

PREPARATION 46 n-Butyllithium in hexane (1.66M solution, 5.2 ml) was added dropwise to a solution of 3-bromo-2,5-dichlorothiophene (2.0 g) and triisopropoxyborane (2.4 ml) in ether (20.0 ml) at −75–65° C. for 10 minutes and the mixture was stirred at same temperature for 1 hour. The reaction mixture was poured onto 1N-hydrochloric acid (30 ml) and the mixture was extracted with ether. The separated extract layer was washed with brine, dried over magnesium sulfate and evaporated in vacuo to give (2,5-dichlorothiophen-3-yl)-dihydroxyborane (1.13 g).

mp: 187–190° C.

IR (Nujol): 3170 cm$^{-1}$

NMR (DMSO-d$_6$, δ): 7.14 (1H, s)

PREPARATION 47

Ethyl glycolate (50.4 g) was added dropwise to a stirred suspension of sodium hydride (60% oil suspension, 38.7 g) in N,N-dimethylformamide (770 ml) for 8 minutes at 5–10° C. under nitrogen gas, and the mixture was stirred for 30 minutes at the same temperature. To the mixture was added dropwise over 10 minutes a solution of 6-fluoro-2-iodobenzaldehyde (110 g) in N,N-dimethylformamide (110 ml) at ambient temperature, and the mixture was stirred for 1.5 hours at 90–95° C. After cooling to 25° C., the reaction mixture was added 2N-sodium hydroxide (220 ml) and stirred for 1 hour at ambient temperature. The mixture was poured onto the mixture of water and ethyl acetate and the separated aqueous layer was adjusted to pH 2 with 6N-hydrochloric acid. The mixture was extracted with ethyl acetate and the extract layer was washed with brine, dried over magnesium sulfate and evaporated in vacuo to give 2-carboxy-4-iodobenzofuran. The mixture of the above residue and conc. sulfuric acid (20 ml) in methanol (200 ml) was heated under reflux for 16 hours. After evaporation of the solvent, the residue was added to water and the mixture was adjusted to pH 8 with potassium carbonate. The mixture was extracted with ethyl acetate and the extract layer was washed with brine, dried over magnesium sulfate and evaporated in vacuo. The residue was triturated with diisopropyl ether to give methyl 4-iodobenzofuran-2-carboxylate (16.13 g).

mp: 141–142° C.

IR (Nujol): 1700 cm$^{-1}$

NMR (DMSO-d$_6$, δ): 3.92 (3H, s), 7.33 (1H, dd, J=7.6, 8.4 Hz), 7.43 (1H, s), 7.78 (1H, d, J=8.4 Hz), 7.79 (1H, d, J=7.6 Hz)

PREPARATION 48

A mixture of 5-(2,5-dichlorothiophen-3-yl)-3-methoxycarbonylbenzoic acid (1.0 g) and thionyl chloride (0.44 ml) in benzene (10 ml) was refluxed for 6 hours. The solvent and excess thionyl chloride was evaporated in vacuo and the residue was dissolved in tetrahydrofuran (20 ml). To this solution was added 1-methylpiperazine (0.6 g) at 7° C. and the mixture was stirred for 2 hours at ambient temperature. After evaporating the solvent, the residue was dissolved in a mixture of ethyl acetate (50 ml) and water (50 ml). The organic layer was washed with brine, dried over magnesium sulfate and evaporated in vacuo. The residue was purified by column chromatography on silica gel eluting with a mixture of chloroform and methanol (10:1) to afford methyl 5-(2,5-dichlorothiophen-3-yl)-3-[(4-methylpiperazin-1-yl)carbonyl]benzoate (1.07 g) as an oil.

IR (Film): 1720, 1625, 1030, 905, 750 cm$^{-1}$

NMR (DMSO-d$_6$, δ): 2.20 (3H, s), 2.1–2.5 (4H, br), 3.2–3.8 (4H, br), 3.90 (3H, s), 7.53 (1H, s), 7.84 (1H, dd, J=1.6, 1.6 Hz), 7.94 (1H, dd, J=1.6, 1.6 Hz), 8.20 (1H, dd, J=1.6, 1.6 Hz)

(+) APCI MASS: 413, 415 (M+H)$^+$

PREPARATION 49

Methyl 3-(2-formyl-3,4-dihydro-1-naphthyl)benzoate (0.44 g) was added to a mixture of hydroxylamine hydrochloride (0.11 g) and 28 methanolic sodium methoxide (0.31 ml) in methanol (10 ml) and the whole was stirred for 19 hours at ambient temperature. The solvent was removed by concentration. To the residue was added a mixture of ethyl acetate, tetrahydrofuran and water and adjusted to pH 2 with 6N-hydrochloric acid. The separated organic layer was washed with brine, dried over magnesium sulfate. The solvent was evaporated in vacuo and the residue was purified by column chromatography on silica gel eluting a mixture of chloroform and methanol (50:1). The eluted fractions containing the desired product were collected and evaporated in vacuo to give methyl 3-(2-hydroxyiminomethyl-3,4-dihydro-1-naphthyl)benzoate (0.36 g).

mp: 171–172° C.

IR (Nujol): 1720 cm$^{-1}$

NMR (DMSO-d$_6$, δ): 2.7–3.0 (4H, m), 3.86 (3H, s), 6.51 (1H, d, J=7.4 Hz), 7.0–7.8 (7H, m), 8.04 (1H, dt, J=1.4, 7.8 Hz), 11.29 (1H, s)

(+) APCI MASS: 308 (M+H)$^+$

PREPARATION 50

The following compounds were obtained according to similar manners to those of Preparations 4 and 46.

(1) (Benzo[b]thiophen-4-yl)-dihydroxyborane
mp: 200° C. (dec.)
IR (Nujol): 3200 (br), 1400, 1350 cm$^{-1}$
NMR (DMSO-d$_6$, δ): 7.33 (1H, dd, J=7.5, 7.5 Hz), 7.72 (1H, d, J=5.5 Hz), 7.77 (1H, d, J=7.5 Hz), 7.93 (1H, d, J=5.5 Hz), 8.03 (1H, d, J=7.5 Hz), 8.23 (2H, s)

(2) (5-Hydroxymethyl-3-methoxycarbonylphenyl-dihydroxyborane
mp: 193–196° C.
IR (Nujol): 3400 (br), 1690, 1600, 1270 cm$^{-1}$
NMR (DMSO-d$_6$, δ): 3.86 (3H, s), 4.56 (2H, s), 5.32 (1H, br s), 7.98 (2H, s), 8.24 (2H, s), 8.30 (1H, s)

(3) (2-Difluoromethylbenzofuran-4-yl)-dihydroxyborane
mp: 117° C. (dec.)
IR (Nujol): 3300 (br), 1610, 1150 cm$^{-1}$
NMR (DMSO-d$_6$, δ): 7.29 (1H, t, J=52.9 Hz), 7.33–7.40 (2H, m), 7.71 (1H, d, J=7.6 Hz), 7.80 (1H, d, J=7.6 Hz), 8.24 (2H, br s)

(4) (2-Methylbenzofuran-3-yl)-dihydroxyborane
mp: 68–70° C.
IR (Nujol): 3200, 1590 cm$^{-1}$
NMR (DMSO-d$_6$, δ): 2.74 (3H, s), 7.12–7.25 (2H, m), 7.40–7.51 (1H, m), 7.92–8.04 (1H, m)

(5) (2-Methylbenzofuran-7-yl)-dihydroxyborane
mp: 208–211° C.
IR (Nujol): 1600, 1210, 1170, 1130, 930, 750 cm$^{-1}$
NMR (DMSO-d$_6$, δ): 2.44 (3H, s), 6.52 (1H, s), 7.14 (1H, dd, J=7.4, 7.4 Hz), 7.44 (1H, d, J=7.4 Hz), 7.53 (1H, d, J=7.4 Hz), 8.05 (2H, s)

PREPARATION 51

The following compounds were obtained according to a similar manner to that of Preparation 6.

(1) 3-(Benzo[b]thiophen-4-yl)benzoic acid
mp: 195–197° C.
IR (Nujol): 1680, 1310 cm$^{-1}$
NMR (DMSO-d$_6$, δ): 7.29–7.53 (3H, m), 7.67 (1H, dd, J=7.6, 7.6 Hz), 7.83–7.86 (2H, m), 8.01–8.12 (3H, m), 13.15 (1H, s)

(2) 3-(Benzo[b]thiophen-3-yl)benzoic acid
mp: 175–176° C.
IR (Nujol): 1700, 1310 cm$^{-1}$
NMR (DMSO-d$_6$, δ): 7.42–7.52 (2H, m), 7.67 (1H, dd, J=7.7, 7.7 Hz), 7.86–7.90 (2H, m), 7.95 (1H, s), 8.02 (1H, ddd, J=7.7, 1.5, 1.5 Hz), 8.11 (1H, ddd, J=7.7, 1.5, 1.5 Hz), 8.16 (1H, dd, J=1.5, 1.5 Hz), 13.17 (1H, br s)
(+) APCI MASS: 255 (M+H)$^+$
Elemental Analysis Calcd. for C$_{15}$H$_{10}$O$_2$S: C 70.85, H 3.96 Found: C 70.73, H 4.06

(3) 3-(2-Difluoromethylbenzofuran-4-yl)benzoic acid
mp: 163–164° C.
IR (Nujol): 1680, 1310 cm$^{-1}$
NMR (DMSO-d$_6$, δ): 7.35 (1H, t, J=52.8 Hz), 7.45–7.53 (2H, m), 7.67–7.75 (2H, m), 7.83 (1H, d, J=7.6 Hz), 8.04 (1H, d, J=7.9 Hz), 8.11 (1H, d, J=7.9 Hz), 8.43 (1H, s), 13.15 (1H, s)
(–) APCI MASS: 287 (M–H)$^-$ (4) 3-(2-Methylbenzofuran-3-yl)benzoic acid
mp: 183–184° C.
IR (Nujol): 1690, 1300 cm$^{-1}$
NMR (DMSO-d$_6$, δ): 2.55 (3H, s), 7.28–7.34 (2H, m), 7.55–7.63 (2H, m), 7.69 (1H, d, J=7.6 Hz), 7.81 (1H, ddd, J=7.6, 1.5, 1.5 Hz), 7.98 (1H, ddd, J=7.6, 1.5 1.5 Hz), 8.08 (1H, dd, J=1.5, 1.5 Hz)
(+) APCI MASS: 253 (M+H)$^+$ (5) 3-(3-Chlorothiophen-4-yl)benzoic acid
mp: 182–183° C.
IR (Nujol): 1680, 1300 cm$^{-1}$
NMR (DMSO-d$_6$, δ): 7.60 (1H, dd, J=7.7, 7.7 Hz), 7.75–7.80 (2H, m), 7.88 (1H, d, J=3.5 Hz), 7.97 (1H, d, J=7.7 Hz), 8.08 (1H, s), 13.14 (1H, s)
(+) APCI MASS: 239 (M+H)$^+$ (6) 3-(2-Methylbenzofuran-7-yl)benzoic acid
mp: 153–155° C.
IR (Nujol): 1685, 1305, 1270, 925, 750 cm$^{-1}$
NMR (DMSO-d$_6$, δ): 2.49 (3H, s), 6.68 (1H, s), 7.32 (1H, dd, J=7.6, 7.6 Hz), 7.46 (1H, dd, J=7.6, 1.2 Hz), 7.57 (1H, dd, J=7.6, 1.2 Hz), 7.67 (1H, dd, J=7.6, 7.6 Hz), 8.01 (1H, ddd, J=7.7, 1.6, 1.6 Hz), 8.10 (1H, ddd, J=7.7, 1.6, 1.6 Hz), 8.43 (1H, dd, J=1.6, 1.6 Hz)
(+) APCI MASS: 253 (M+H)$^+$ (7) 3-(Benzofuran-3-yl)benzoic acid
mp: 193–194° C.
IR (Nujol): 1700, 1120, 740 cm$^{-1}$
NMR (DMSO-d$_6$, δ): 7.36–7.49 (2H, m), 7.63–7.73 (2H, m), 7.87–8.04 (3H, m), 8.29–8.30 (1H, m), 8.50 (1H, s)

(8) Methyl 5-[(E)-2-carboxyethenyl]-3-(2,5-dichlorothiophen-3-yl)benzoate
mp: 142–145° C.
IR (Nujol): 1725, 1690 cm$^{-1}$
NMR (DMSO-d$_6$, δ): 3.90 (3H, s), 6.72 (1H, d, J=16.1 Hz), 7.55 (1H, s), 7.71 (1H, d, J=16.1 Hz), 8.18 (2H, s), 8.21 (1H, s), 12.57 (1H, br s)

PREPARATION 52

The following compounds were obtained according to a similar manner to that of Preparation 15.

(1) Methyl 3-(benzo[b]thiophen-4-yl)benzoate
mp: 90–92° C.
IR (Nujol): 1720, 13b0, 1250 cm$^{-1}$
NMR (DMSO-d$_6$, δ): 3.89 (3H, s), 7.39–7.44 (2H, m), 7.50 (1H, dd, J=7.6, 7.6 Hz), 7.69 (1H, dd, J=7.7, 7.7 Hz), 7.84–7.90 (2H, m), 8.02–8.12 (3H, m)
(+) APCI MASS: 269 (M+H)$^+$ (2) Methyl 3-(-benzo[b]thiophen-3-yl)benzoate
IR (Neat): 1720, 1580, 1430, 1280, 1210 cm$^{-1}$
NMR (DMSO-d$_6$, δ): 3.90 (3H, s), 7.42–7.52 (2H, m), 7.70 (1H, dd, J=7.7, 7.7 Hz), 7.84–7.94 (2H, m), 7.97 (1H, s), 8.03 (1H, d, J=7.7 Hz), 8.08–8.16 (2H, m)
(+) APCI MASS: 269 (M+H)$^+$ (3) Methyl 3-(2-difluoromethylbenzofuran-4-yl)benzoate
mp: 98–99° C.
IR (Nujol): 1710, 1300, 1260 cm$^{-1}$
NMR (DMSO-d$_6$, δ): 3.92 (3H, s), 7.35 (1H, t, J=52.8 Hz), 7.45–7.52 (2H, m), 7.70–7.77 (2H, m), 7.83 (1H, d, J=7.7 Hz), 8.04 (1H, d, J=7.7 Hz), 8.14 (1H, d, J=7.7 Hz), 8.43 (1H, s)
(+) APCI MASS: 303 (M+H)$^+$
Elemental Analysis Calcd. for C$_{17}$H$_{12}$F$_2$O$_3$: C 67.55, H 4.00 Found: C 67.32, H 3.87

(4) Methyl 3-(2-methylbenzofuran-3-yl)benzoate
  IR (Neat): 1720, 1620, 1450, 1290, 1200 cm$^{-1}$
  NMR (DMSO-d$_6$, δ): 2.55 (3H, s), 3.90 (3H, s), 7.25–7.38 (2H, m), 7.54–7.62 (2H, m), 7.70 (1H, dd, J=7.7, 7.7 Hz), 7.84 (1H, ddd, J=7.7, 1.5, 1.5 Hz), 7.99 (1H, ddd, J=7.7, 1.5, 1.5 Hz), 8.08 (1H, dd, J=1.5, 1.5 Hz)
  (+) APCI MASS: 267 (M+H)$^+$ (5) Methyl 3-(3-chlorothiophen-4-yl)benzoate
  IR (Neat): 1720, 1580, 1430, 1280, 1220 cm$^{-1}$
  NMR (DMSO-d$_6$, δ): 3.89 (3H, s), 7.63 (1H, dd, J=7.7, 7.7 Hz), 7.78–7.83 (2H, m), 7.89 (1H, d, J=3.5 Hz), 8.00 (1H, d, J=7.7 Hz), 8.09 (1H, s)
  (+) APCI MASS: 253 (M+H)$^+$ (6) Methyl 3-(2-methylbenzofuran-7-yl)benzoate
  IR (Film): 1720, 1600, 1435, 1245, 750 cm$^{-1}$
  NMR (DMSO-d$_6$, δ): 2.48 (3H, s), 3.91 (3H, s), 6.68 (1H, s), 7.32 (1H, dd, J=7.6, 7.6 Hz), 7.46 (1H, d, J=7.6 Hz), 7.57 (1H, d, J=7.6 Hz), 7.69 (1H, dd, J=7.7, 7.7 Hz), 8.00 (1H, d, J=7.7 Hz), 8.13 (1H, d, J=7.7 Hz), 8.41 (1H, s)

(7) Methyl 3-(benzofuran-3-yl)benzoate
  IR (Film): 1720, 1450, 1210, 1110, 740 cm$^{-1}$
  NMR (DMSO-d$_6$, δ): 3.91 (3H, s), 7.36–7.48 (2H, m), 7.65–7.75 (2H, m), 7.90–8.07 (3H, m), 8.28–8.30 (1H, m), 8.52 (1H, s)
  (+) APCI MASS: 253 (M+H)$^+$

PREPARATION 53

The following compounds were obtained according to a similar manner to that of Preparation 23.

(1) Methyl 3-(2-chlorobenzo[b]thiophen-3-yl)benzoate
  mp: 76–77° C.
  IR (Nujol): 1730, 1290, 1260 cm$^{-1}$
  NMR (DMSO-d$_6$, δ): 3.89 (3H, s), 7.40–7.53 (3H, m), 7.75 (1H, dd, J=7.5, 7.5 Hz), 7.82 (1H, d, J=7.5 Hz), 8.05–8.12 (3H, m)
  (+) APCI MASS: 303 (M+H)$^+$ (2) Methyl 3-(2-chlorobenzofuran-3-yl)benzoate
  mp: 62–64° C.
  IR (Nujol): 1730, 1280, 1260 cm$^{-1}$
  NMR (DMSO-d$_6$, δ): 3.91 (3H, s), 7.36–7.47 (2H, m), 7.64–7.77 (3H, m), 7.95 (1H, ddd, J=7.8, 1.6, 1.6 Hz), 8.05 (1H, ddd, J=7.8, 1.6, 1.6 Hz), 8.22 (1H, dd, J=1.6, 1.6 Hz)
  (+) APCI MASS: 287, 289 (M+H)$^+$

PREPARATION 54

The following compounds were obtained according to similar manners to those of Preparations 8 and 9.

(1) Methyl 3-(benzofuran-4-yl)-5-hydroxymethylbenzoate
  IR (Neat): 3350 (br), 1700, 1600, 1440, 1300 cm$^{-1}$
  NMR (DMSO-d$_6$, δ): 3.90 (3H, s), 4.69 (2H, d, J=5.8 Hz), 5.46 (1H, t, J=5.8 Hz), 7.06 (1H, d, J=2.3 Hz), 7.40–7.50 (2H, m), 7.67 (1H, dd, J=6.5, 2.6 Hz), 7.87 (1H, s), 8.00 (1H, s), 8.06 (1H, s), 8.12 (1H, d, J=2.3 Hz)
  (+) APCI MASS: 283 (M+H)$^+$ (2) Methyl 3-(indol-4-yl)benzoate
  mp: 103–105° C.
  IR (Nujol): 3350, 1700 cm$^{-1}$
  NMR (DMSO-d$_6$, δ): 3.90 (3H, s), 6.54 (1H, d, J=2.0 Hz), 7.13 (1H, d, J=7.3 Hz), 7.22 (1H, dd, J=7.3, 7.3 Hz), 7.45–7.49 (2H, m), 7.66 (1H, dd, J=7.7, 7.7 Hz), 7.93–7.99 (2H, m), 8.26 (1H, dd, J=1.5, 1.5 Hz), 11.37 (1H, s)
  (+) APCI MASS: 252 (M+H)$^+$ (3) Methyl 3-(1-oxoindan-4-yl)benzoate
  mp: 125–127° C.
  IR (Nujol): 1710, 1260 cm$^{-1}$
  NMR (DMSO-d$_6$, δ): 2.65 (2H, t, J=5.6 Hz), 3.14 (2H, t, J=5.6 Hz), 3.89 (3H, s), 7.57 (1H, dd, J=7.5, 7.5 Hz), 7.63–7.76 (3H, m), 7.87 (1H, ddd, J=7.7, 1.6, 1.6 Hz), 8.02 (1H, ddd, J=7.7, 1.6, 1.6 Hz), 8.08 (1H, dd, J=1.6, 1.6 Hz)
  (+) APCI MASS: 267 (M+H)$^+$ (4) Methyl 3-[2,3-(methylenedioxy)phenyl]benzoate
  IR (Nujol): 1717, 1670 cm$^{-1}$
  NMR (DMSO-d$_6$, δ): 3.89 (3H, s), 6.12 (2H, s), 6.95–7.00 (2H, m), 7.11–7.21 (1H, m), 7.57–7.69 (1H, m), 7.92–8.04 (2H, m), 8.30–8.34 (1H, m)
  (+) APCI MASS: 257 (M+H)$^+$ (5) Dimethyl 5-(2,5-dichlorothiophen-3-yl)isophthalate
  mp: 109–112° C.
  IR (Nujol): 1730 cm$^{-1}$
  NMR (DMSO-d$_6$, δ): 3.90 (6H, s), 7.56 (1H, s), 8.35 (2H, s), 8.48 (1H, s)
  (+) APCI MASS: 345 (M+H)$^+$ (6) Methyl 3-(2-hydroxymethyl-3,4-dihydro-1-naphthyl)benzoate
  IR (Film): 3350, 2950, 1710, 1600, 1580 cm$^{-1}$
  NMR (DMSO-d$_6$, δ): 2.4–2.6 (2H, m), 2.8–2.9 (2H, m), 3.8–3.9 (5H, m), 4.79 (1H, t, J=5.4 Hz), 6.40 (1H, d, J=7.3 Hz), 7.0–7.3 (3H, m), 7.45 (1H, d, J=7.6 Hz), 7.61 (1H, t, J=7.6 Hz), 7.70 (1H, d, J=0.5 Hz), 7.9–8.0 (1H, m)
  (+) APCI MASS: 277 (M−OH)$^+$ (7) Dimethyl 5-(benzofuran-4-yl)isophthalate
  mp: 148–150° C.
  IR (Nujol): 1730, 1255, 1005, 755 cm$^{-1}$
  NMR (DMSO-d$_6$, δ): 3.94 (6H, s), 7.05 (1H, d, J=1.8 Hz), 7.46–7.49 (2H, m), 7.69–7.75 (1H, m), 8.14 (1H, d, J=1.8 Hz), 8.39 (2H, s), 8.50 (1H, s)
  (+) APCI MASS: 311 (M+H)$^+$
  Elemental Analysis Calcd. for $C_{18}H_{14}O_5$: C 69.67, H 4.55
  Found: C 69.30, H 4.55

(8) Methyl 3-(2,3-dihydrobenzofuran-4-yl)benzoate
  IR (Film): 1720, 1580, 1110, 985, 750 cm$^{-1}$
  NMR (DMSO-d$_6$, δ): 3.27 (2H, t, J=8.6 Hz), 3.88 (3H, s), 4.53 (2H, t, J=8.6 Hz), 6.83 (1H, d, J=7.9 Hz), 6.94 (1H, d, J=7.9 Hz), 7.23 (1H, dd, J=7.9, 7.9 Hz), 7.62 (1H, dd, J=7.7 Hz), 7.82 (1H, d, J=7.7 Hz), 7.96 (1H, d, J=7.7 Hz), 8.05 (1H, s)
  (+) APCI MASS: 255 (M+H)$^+$

PREPARATION 55

The following compounds were obtained according to a similar manner to that of Preparation 26-(1).

(1) 4-Bromo-2-difluoromethylbenzofuran
  IR (Neat): 1610, 1570, 1420, 1360, 1150 cm$^{-1}$
  NMR (DMSO-d$_6$, δ): 7.32 (1H, dd, J=7.8, 7.8 Hz), 7.36 (1H, t, J=52.7 Hz), 7.55 (1H, t, J=2.2 Hz), 7.72 (1H, d, J=7.8 Hz), 7.80 (1H, d, J=7.8 Hz)

(2) Methyl 3-(2-difluoromethylbenzofuran-3-yl)benzoate
  IR (Neat): 1720, 1610, 1450, 1390, 1290, 1210 cm$^{-1}$
  NMR (DMSO-d$_6$, δ): 3.91 (3H, s), 7.29 (1H, t, J=51.4 Hz), 7.44 (1H, dd, J=7.8, 7.8 Hz), 7.58 (1H, dd, J=7.8, 7.8 Hz), 7.70 (1H, d, J=7.8 Hz), 7.75–7.89 (3H, m), 8.09 (1H, s), 8.11 (1H, d, J=7.8 Hz)

(3) Methyl 3-(2-difluoromethyl-3,4-dihydro-1-naphthyl)benzoate
  IR (Film): 2950, 1720 cm$^{-1}$
  NMR (DMSO-d$_6$, δ): 2.4–2.6 (2H, m), 2.9–3.0 (2H, m), 3.86 (3H, s), 6.13 (1H, t, J=55.2 Hz), 6.51 (1H, d, J=7.7 Hz), 7.1–7.4 (3H, m), 7.51 (1H, d, J=7.6 Hz), 7.6–7.8 (2H, m), 8.06 (1H, d, J=7.8 Hz)

PREPARATION 56

The following compounds were obtained according to a similar manner to that of Preparation 1.

(1) 4-Trifluoromethylsulfonyloxyindole

IR (Neat): 3450, 1630, 1500, 1410, 1350 cm$^{-1}$

NMR (DMSO-d$_6$, δ): 6.48 (1H, d, J=2.0 Hz), 7.08 (1H, d, J=7.9 Hz), 7.21 (1H, dd, J=7.9, 7.9 Hz), 7.52–7.57 (2H, m), 11.74 (1H, s)

(+) APCI MASS: 266 (M+H)$^+$ (2) 4-(Trifluoromethylsulfonyloxy)-1-oxoindan

IR (Neat): 1720, 1610, 1470, 1420, 1330 cm$^{-1}$

NMR (DMSO-d$_6$, δ): 2.73–2.80 (2H, m), 3.15–3.21 (2H, m), 7.65 (1H, dd, J=7.7, 7.7 Hz), 7.76–7.82 (2H, m)

(+) APCI MASS: 281 (M+H)$^+$ (3) 2,3-(Methylenedioxy)-1-trifluoromethylsulfonyloxybenzene IR (Film): 1630, 1420, 1135 cm$^{-1}$ NMR (DMSO-d$_6$, δ): 6.21 (2H, s), 6.93–7.11 (3H, m)

PREPARATION 57

A mixture of 3-bromo-2,5-dichlorothiophene (0.30 g), [3,5-bis(methoxycarbonyl)phenyl]-dihydroxyborane (0.37 g), lithium chloride (0.164 g), tetrakis(triphenylphosphine)palladium(0) (0.0747 g) and 2M aqueous sodium carbonate solution (1.55 ml) in 1,2-dimethoxyethane (3.6 ml) was heated at 85° C. and stirred vigorously for 4 hours under nitrogen. The reaction mixture was cooled to room temperature and to the mixture was added ethyl acetate (20 ml) and 2M sodium carbonate solution (20 ml). The layers were separated, and the organic layer was washed successively with water and brine, dried over magnesium sulfate and evaporated under reduced pressure. The residue was purified by column chromatography on silica gel eluting with a mixture of hexane and ethyl acetate (20:1). The fractions containing the desired product were collected and evaporated in vacuo to give dimethyl 5-(2,5-dichlorothiophen-3-yl)isophthalate (0.26 g).

mp: 109–112° C.

IR (Nujol): 1730, 1300, 1250 cm$^{-1}$

NMR (DMSO-d$_6$, δ): 3.90 (6H, s), 7.56 (1H, s), 8.35 (2H, s), 8.48 (1H, s)

(+) APCI MASS: 345 (M+H)$^+$

PREPARATION 58

The following compounds were obtained according to a similar manner to that of Preparation 42.

(1) Methyl 5-(2,5-dichlorothiophen-3-yl)-3-[(2-morpholinoethyl)carbamoyl]benzoate mp: 133–135° C.

IR (Nujol): 3250, 1720, 1630, 1540, 1260 cm$^{-1}$

NMR (DMSO-d$_6$, δ): 2.42 (4H, t, J=4.5 Hz), 2.48–2.52 (2H, m), 3.37–3.48 (2H, m), 3.57 (4H, t, J=4.5 Hz), 7.52 (1H, s), 8.27 (2H, dd, J=1.5, 1.5 Hz), 8.45 (1H, dd, J=1.5, 1.5 Hz), 8.73 (1H, t, J=5.5 Hz)

(+) APCI MASS: 443 (M+H)$^+$, 445 (M+H)$^+$

Elemental Analysis Calcd. for C$_{19}$H$_{20}$Cl$_2$N$_2$O$_4$S: C 51.47, H 4.55, N 6.32 Found: C 51.32, H 4.46, N 6.20

(2) Methyl 3-[(2-dimethylaminoethyl)carbamoyl]-5-(benzofuran-4-yl)benzoate

IR (Film): 3300, 1720, 1245, 750 cm$^{-1}$

NMR (DMSO-d$_6$, δ): 2.19 (6H, s), 2.43 (2H, t, J=6.8 Hz), 3.40 (2H, td, J=6.8, 6.5 Hz), 3.93 (3H, s), 7.06 (1H, d, J=2.2 Hz), 7.45–7.50 (2H, m), 7.65–7.75 (1H, m), 8.14 (1H, d, J=2.2 Hz), 8.30 (1H, s), 8.36 (1H, s), 8.47 (1H, s), 8.78 (1H, t, J=6.5 Hz)

(+) APCI MASS: 367 (M+H)$^+$

PREPARATION 59

The following compound was obtained according to a similar manner to that of Preparation 3.

Methyl 3-(2,5-dichlorothiophen-3-yl)-5-hydroxymethylbenzoate mp: 137–139° C.

IR (Nujol): 3460, 1705 cm$^{-1}$

NMR (DMSO-d$_6$, δ): 3.88 (3H, s), 4.62 (2H, d, J=5.8 Hz), 5.46 (1H, t, J=5.8 Hz), 7.45 (1H, s), 7.77 (1H, s), 7.98 (1H, s), 8.01 (1H, s)

Elemental Analysis Calcd. for C$_{13}$H$_{10}$O$_3$SCl$_2$: C 49.23, H 3.18 Found: C 48.91, H 2.95

PREPARATION 60

The following compound was obtained according to similar manners to those of Preparations 38 and 44.

Methyl 3-(2-formyl-3,4-dihydro-1-naphthyl)benzoate

IR (Nujol): 2950, 2850, 1720, 1660, 1600, 1560 cm$^{-1}$

NMR (DMSO-d$_6$, δ): 2.5–2.7 (2H, m), 2.8–3.0 (2H, m), 3.86 (3H, s), 6.69 (1H, d, J=7.6 Hz), 7.1–7.4 (3H, m), 7.6–7.7 (2H, m), 7.86 (1H, s), 8.0–8.2 (1H, m), 9.41 (1H, s)

(+) APCI MASS: 293 (M+H)$^+$

PREPARATION 61

A mixture of dimethyl 5-hydroxyisophthalate (2 g) and N,N-dimethylethylenediamine (1.04 ml) was heated at 100° C. for 2 hours. After being cooled to room temperature, the reaction mixture was evaporated in vacuo. The residue was purified by column chromatography on silica gel eluting with a mixture of chloform, methanol and triethylamine (100:10:1) to give methyl 3-[(2-dimethylaminoethyl)carbamoyl]- 5-hydroxybenzoate (1.11 g).

mp: 118–120° C.

IR (Nujol): 3370, 1710, 1630, 1590, 1540, 1230 cm$^{-1}$

NMR (DMSO-d$_6$, δ): 2.19 (6H, s), 2.42 (2H, t, J=6.8 Hz), 3.31–3.41 (2H, m), 3.87 (3H, s), 7.47–7.52 (2H, m), 7.89 (1H, dd, J=1.4, 1.4 Hz), 8.52 (1H, t, J=5.5 Hz), 10.05 (1H, br s)

(+) APCI MASS: 267 (M+H)$^+$

Elemental Analysis Calcd. for C$_{13}$H$_{18}$N$_2$O$_4$: C 58.64, H 6.81, N 10.52 Found: C 58.49, H 6.90, N 10.46

PREPARATION 62

To a mixture of methyl 3-[(2-dimethylaminoethyl)carbamoyl]-5-hydroxybenzoate (11.9 g), 2,6-lutidine (6.25 ml) and 4-(dimethylamino)pyridine (0.84 g) in dichloromethane (240 ml) was added dropwise trifluoromethanesulfonic anhydride (9.02 ml) at −30° C. over 30 minutes. After stirring at room temperature for 4 hours, water (100 ml) was added to the reaction mixture. Two phases were separated and the aqueous layer was extracted with dichloromethane. The organic layers were combined, washed with water, dried over magnesium sulfate and evaporated in vacuo. The residue was triturated with diethyl ether and the crystalline was collected and washed with diethyl ether to give methyl 3-[(2-dimethylaminoethyl)carbamoyl]-5-trifluoromethylsulfonyloxybenzoate trifluoromethanesulfonate (16.02 g).

mp: 120–122° C.

IR (Nujol): 3340, 3150, 1720, 1650, 1580, 1550 cm$^{-1}$

NMR (DMSO-d$_6$, δ): 2.87 (6H, s), 3.29 (2H, t, J=5.8 Hz), 3.61–3.70 (2H, m), 3.95 (3H, s), 8.16–8.21 (2H, m), 8.59 (1H, dd, J=1.4 Hz), 9.11 (1H, t, J=5.5 Hz), 9.26 (1H, br s)

Elemental Analysis Calcd. for C$_{14}$H$_{17}$F$_3$N$_2$O$_6$S.CF$_3$SO$_3$H: C 32.85, H 3.31, N 5.11 Found: C 32.90, H 3.30, N 5.10

PREPARATION 63

To a mixture of methyl 3-[(2-dimethylaminoethyl)carbamoylmethoxy]-5-hydroxybenzoate (1.30 g), 2,6-lutidine (0.613 ml) and 4-(dimethylamino)pyridine (0.083 g) in dichloromethane (26 ml) was added dropwise trifluoromethanesulfonic anhydride (0.886 ml) at −30° C. After stirring at room temperature for 4 hours, water was added to the reaction mixture and the mixture was adjusted to pH 8. Two layers were separated and the aqueous layer was extracted with dichloromethane. The organic layers were combined, washed with water, dried over magnesium sulfate and evaporated in vacuo. The residue was purified by column chromatography on silica gel eluting with a mixture of chloroform and methanol (20:1). The fractions containing the desired product were collected and evaporated in vacuo. The residue was triturated with n-hexane, collected by filtration and washed with n-hexane to give methyl 3-[(2-dimethylaminoethyl)carbamoylmethoxy]-5-trifluoromethylsulfonyloxybenzoate (1.47 g).

mp: 80–82° C.

IR (Nujol): 3400, 1730, 1670, 1530, 1300 cm$^{-1}$

NMR (DMSO-d$_6$, δ): 2.13 (6H, s), 2.30 (2H, t, J=6.7 Hz), 3.17–3.27 (2H, m), 3.90 (3H, s), 4.66 (2H, s), 7.46 (1H, dd, J=2.2, 2.2 Hz), 7.55 (1H, dd, J=2.2, 2.2 Hz), 7.62 (1H, dd, J=2.2, 2.2 Hz), 8.12 (1H, t, J=5.6 Hz)

(+) APCI MASS: 429 (M+H)$^+$

Elemental Analysis Calcd. for C$_{15}$H$_{19}$F$_3$N$_2$O$_7$S: C 42.06, H 4.47, N 6.54 Found: C 42.15, H 4.54, N 6.95

PREPARATION 64

Methyl 3-[(2-dimethylaminoethyl)carbamoyl]-5-trifluromethylsulfonyloxybenzoate trifluoromethanesulfonate (1.45 g) was dissolved in ethyl acetate (150 ml) and to the mixture water (50 ml) was added. The mixture was adjusted to pH 9 and two layers were separated. The organic layer was washed with brine, dried over magnesium sulfate and evaporated in vacuo to give methyl 3-[(2-dimethylaminoethyl)carbamoyl]-5-trifluoromethylsulfonyloxvbenzoate (1.14 g).

IR (CHCl$_3$): 3330, 1720, 1660, 1420, 1140, 990, 900 cm$^{-1}$

NMR (DMSO-d$_6$, δ): 2.22 (6H, s), 2.47 (2H, t, J=6.6 Hz), 3.36–3.46 (2H, m), 3.94 (3H, s), 8.13 (1H, dd, J=1.4, 1.4 Hz), 8.20 (1H, dd, J=1.4, 1.4 Hz), 8.56 (1H, dd, J=1,4, 1.4 Hz), 8.90 (1H, t, J=5.5 Hz)

PREPARATION 65

To a cold solution (−70° C.) of 2,3-dibromobenzofuran (9 g) in tetrahydrofuran (90 ml) was added dropwise n-butyllithium-hexane solution (22.0 ml) over 20 minutes. After stirring at −70° C. for 15 minutes, a solution of N,N-dimethylformamide (2.63 ml) in tetrahydrofuran (18 ml) was added to the reaction mixture over 10 minutes. After stirring at −70° C. for 2 hours, a solution of triisopropylborane (9.03 ml) in tetrahydrofuran (9 ml) was added to the reaction mixture and then n-butyllithium-hexane solution (20.0 ml) was added dropwise over 30 minutes. The mixture was stirred at −70° C. for 2 hours and was poured onto 2M hydrochloric acid solution (98 ml). The product was extracted with ethyl acetate (2×200 ml) and the organic layer was washed with brine, dried over magnesium sulfate, and concentrated under reduced pressure. The desired product was extracted with aqueous sodium carbonate solution (10 g/150 ml of water) and the aqueous layer was adjusted to pH 3 with 6N hydrochloric acid. The product was extracted with ethyl acetate (2×150 ml) and the organic layer was washed with brine, dried over magnesium sulfate and evaporated in vacuo. The residue was triturated with petroleum ether, collected and washed with petroleum ether to give (2-formylbenzofuran-3-yl-)dihydroxyborane (1.71 g).

mp: 167° C. (dec.)

IR (Nujol): 3300 (br), 1660, 1560, 1400, 1290, 1250 cm$^{-1}$

NMR (DMSO-d$_6$, δ): 7.38 (1H, dd, J=8.0, 7.1 Hz), 7.56 (1H, dd, J=8.3, 7.1 Hz), 7.72 (1H, d, J=8.0 Hz), 8.02 (1H, d, J=8.3 Hz), 10.04 (1H, s)

PREPARATION 66

The following compound was obtained according to a similar manner to that of Preparation 65.

(2-Formylbenzo[b]thiophen-3-yl)dihydroxyborane mp: 148° C. (dec.)

IR (Nujol): 3350 (br), 1650, 1500 cm$^{-1}$

NMR (DMSO-d$_6$, δ): 7.48 (1H, dd, J=7.1, 7.1 Hz), 7.55 (1H, dd, J=7.1, 7.1 Hz), 8.08 (1H, d, J=7.1 Hz), 8.15 (1H, d, J=7.1 Hz), 10.21 (1H, s)

PREPARATION 67

To a mixture of methyl 3,5-dihydroxybenzoate (20 g) in N,N-dimethylformamide (200 ml) was added sodium hydride (60% in mineral oil, 5.23 g) slowly at 10° C. After stirring at 10° C. for 30 minutes, benzyl bromoacetate (20.7 ml) was added dropwise to the mixture over 10 minutes. The reaction mixture was stirred at room temperature overnight and then evaporated in vacuo. Ethyl acetate (400 ml) and water (100 ml) was added to the residue and the mixture was adjusted to pH 5 with hydrochloric acid. Two layers were separated and the organic layer was washed successively with water and brine, dried over magnesium sulfate and evaporated in vacuo. The residue was purified by column chromatography on silica gel eluting with a mixture of toluene and ethyl acetate (20:1). The fractions containing the desired product were collected and evaporated in vacuo to give methyl 3-benzyloxycarbonylmethoxy-5-hydroxybenzoate (12.92 g).

mp: 95–97° C.

IR (Nujol): 3300, 1740, 1710, 1590, 1340, 1240, 1180 cm$^{-1}$

NMR (DMSO-d$_6$, δ): 3.81 (3H, s), 4.81 (2H, s), 5.21 (2H, s), 6.61 (1H, dd, J=2.3, 2.3 Hz), 6.91 (1H, dd, J=2.3, 2.3 Hz), 7.02 (1H, dd, J=2.3, 2.3 Hz), 7.36 (5H, s), 9.93 (1H, s)

(+) APCI MASS: 317 (M+H)$^+$

PREPARATION 68

10% palladium on carbon (0.1 g) was added to a mixture of methyl 3-benzyloxycarbonylmethoxy-5-hydroxybenzoate (1 g) in methanol (20 ml) and the mixture was subjected to catalytic reduction at ambient temperature under atmospheric pressure. The catalyst was removed by filtration and the filtrate was evaporated in vacuo to give methyl 3-carboxymethoxy-5-hydroxybenzoate (0.74 g).

mp: 170–172° C.

IR (Nujol): 3300, 1740, 1700, 1590 cm$^{-1}$

NMR (DMSO-d$_6$, δ): 3.82 (3H, s), 4.67 (2H, s), 6.57 (1H, dd, J=2.3, 2.3 Hz), 6.88 (1H, dd, J=2.3, 2.3 Hz), 6.99 (1H, dd, J=2.3, 2.3 Hz)

(+) APCI MASS: 227 (M+H)$^+$

PREPARATION 69

To a mixture of methyl 3-carboxymethoxy-5-hydroxybenzoate (2 g), N,N-dimethylethylenediamine (1.07 ml) and 1-hydroxybenzotriazole (1.31 g) in N,N-dimethylformamide (40 ml) was added 1-ethyl-3-(3-dimethylaminopropyl)carbodiimide (1.86 g) under ice cooling. After stirring at room temperature for 5 hours, the solvent of the reaction mixture was removed under reduced pressure. The residue was purified by column chromatography on aluminum eluting with a mixture of chloroform and methanol (20:1 to 5:1). The fractions containing the desired product were collected and evaporated in vacuo. Then the residue was triturated with diethyl ether, collected by filtration and washed with diethyl ether to give methyl 3-[(2-dimethylaminoethyl)carbamoylmethoxy]-5-hydroxybenzoate (1.94 g).

mp: 105–107° C.

IR (Nujol): 3300, 1710, 1650, 1590, 1550, 1240, 1170 cm$^{-1}$

NMR (DMSO-d$_6$, δ): 2.13 (6H, s), 2.30 (2H, t, J=6.7 Hz), 3.17–3.27 (2H, m), 3.82 (3H, s), 4.47 (2H, s), 6.62 (1H, dd, J=2.2, 2.2 Hz), 6.96 (1H, dd, J=2.2, 2.2 Hz), 7.00 (1H, dd, J=2.2, 2.2 Hz), 7.99 (1H, t, J=5.6 Hz), 10.00 (1H, br s)

(+) APCI MASS: 297 (M+H)$^+$

PREPARATION 70

The following compounds were obtained according to a similar manner to that of Preparation 8 or 9.

(1) Dimethyl 5-(2-formylbenzofuran-3-yl)isophthalate
mp: 197–199° C.
IR (Nujol): 1730, 1660, 1600, 1260 cm$^{-1}$
NMR (DMSO-d$_6$, δ): 3.94 (6H, s), 7.49 (1H, dd, J=7.9, 7.2 Hz), 7.70 (1H, dd, J=8.4, 7.2 Hz), 7.80 (1H, d, J=7.9 Hz), 7.87 (1H, d, J=8.4 Hz), 8.52 (2H, d, J=1.6 Hz), 8.61 (1H, dd, J=1.6, 1.6 Hz), 9.83 (1H, s)
(+) APCI MASS: 339 (M+H)$^+$ (2) Dimethyl 5-(2-formylbenzo[b]thiophen-3-yl)isophthalate
mp: 174–176° C.
IR (Nujol): 1710, 1660, 1300, 1250 cm$^{-1}$
NMR (DMSO-d$_6$, δ): 3.93 (6H, s), 7.53 (1H, dd, J=7.9, 7.9 Hz), 7.65 (1H, dd, J=7.9, 7.9 Hz), 7.72 (1H, d, J=7.9 Hz), 8.21 (1H, d, J=7.9 Hz), 8.40 (2H, d, J=1.6 Hz), 8.64 (1H, dd, J=1.6, 1.6 Hz), 9.84 (1H, s)
(+) APCI MASS: 355 (M+H)$^+$ (3) Methyl 5-(3,5-dichlorophenyl)-3-[(2-dimethylaminoethyl)carbamoyl]benzoate
IR (benzene): 3300, 1720, 1650 cm$^{-1}$
NMR (DMSO-d$_6$, δ): 2.29 (6H, s), 2.56 (2H, t, J=6.7 Hz), 3.41–3.51 (2H, m), 3.93 (3H, s), 7.68 (1H, dd, J=1.8, 1.8 Hz), 7.85 (2H, d, J=1.8 Hz), 8.33 (1H, dd, J=1.6, 1.6 Hz), 8.38 (1H, dd, J=1.6, 1.6 Hz), 8.47 (1H, dd, J=1.6, 1.6 Hz), 8.81 (1H, t, J=5.7 Hz)
(+) APCI MASS: 395 (M+H)$^+$, 397 (M+H)$^+$ (4) Methyl 5-(3,5-dichlorophenyl)-3-[(2-dimethylaminoethyl)carbamoylmethoxy]benzoate
IR (benzene): 3400, 1730, 1670, 1590, 1540, 1420 cm$^{-1}$
NMR (DMSO-d$_6$, δ): 2.24 (6H, s), 2.39–2.49 (2H, m), 3.21–3.30 (2H, m), 3.90 (3H, s), 4.66 (2H, s), 7.62 (1H, dd, J=1.9, 1.9 Hz), 7.66 (1H, dd, J=1.9, 1.9 Hz), 7.73 (1H, dd, J=1.9, 1.9 Hz), 7.81 (2H, d, J=1.9 Hz), 7.84 (1H, dd, J=1.9, 1.9 Hz), 8.16 (1H, t, J=5.6 Hz)
(+) APCI MASS: 425 (M+H)$^+$, 427 (M+H)$^+$ (5) Methyl 5-(2-difluoromethylbenzofuran-4-yl)-3-[(2-dimethylaminoethyl)carbamoylmethoxy]benzoate
IR (benzene) 3400, 1710, 1430, 1350, 1220 cm$^{-1}$
NMR (DMSO-d$_6$, δ): 2.16 (6H, s), 2.36 (2H, t, J=6.7 Hz), 3.20–3.30 (2H, m), 3.90 (3H, s), 4.68 (2H, s), 7.31 (1H, t, J=52.7 Hz), 7.45–7.62 (5H, m), 7.70–7.80 (2H, m), 8.14 (1H, t, J=5.6 Hz)
(+) APCI MASS: 447 (M+H)$^+$ (6) Methyl 5-(2,5-dichlorothiophen-3-yl)-3-[(2-dimethylaminoethyl)carbamoylmethoxy]benzoate
mp: 106–110° C.
IR (Nujol): 3400, 1710, 1670, 1530, 1290 cm$^{-1}$
NMR (DMSO-d$_6$, δ): 2.13 (6H, s), 2.30 (2H, t, J=6.7 Hz), 3.18–3.28 (2H, m), 3.88 (3H, s), 4.62 (2H, s), 7.43 (1H, dd, J=1.4, 1.4 Hz), 7.47 (1H, s), 7.55 (1H, dd, J=1.4, 1.4 Hz), 7.78 (1H, dd, J=1.4, 1.4 Hz), 8.08 (1H, t, J=5.6 Hz)
(+) APCI MASS: 431 (M+H) +, 433 (M+H)$^+$ (7) Methyl 3-(2-formylbenzo[b]thiophen-3-yl)benzoate
mp: 126–128° C.
IR (Nujol): 1720, 1650, 1510, 1270, 1250 cm$^{-1}$
NMR (DMSO-d$_6$, δ): 3.90 (3H, s), 7.53 (1H, dd, J=8.0, 8.0 Hz), 7.66 (1H, dd, J=7.1, 8.0 Hz), 7.72–7.82 (2H, m), 7.98 (1H, ddd, J=7.8, 1.5, 1.5 Hz), 8.14–8.22 (3H, m), 9.85 (1H, s)
(+) APCI MASS: 297 (M+H)$^+$ (8) Methyl 5-(benzofuran-3-yl)-3-[(2-dimethylaminoethyl)carbamoyl]benzoate
mp: 104–106° C.
IR (Nujol): 3250, 1710, 1640, 1600, 1540, 1260 cm$^{-1}$
NMR (DMSO-d$_6$, δ): 2.22 (6H, s), 2.47 (2H, t, J=6.9 Hz), 3.37–3.47 (2H, m), 3.96 (3H, s), 7.37–7.49 (2H, m), 7.68–7.74 (1H, m), 7.89–7.95 (1H, m), 8.39 (1H, dd, J=1.6, 1.6 Hz), 8.45 (2H, dd, J=1.6, 1.6 Hz), 8.55 (1H, s), 8.77 (1H, t, J=5 5 Hz)
(+) APCI MASS: 367 (M+H)$^+$ (9) Dimethyl 5-(2-formylthiophen-3-yl)isophthalate
mp: 167–170° C.
IR (Nujol): 1720, 1650, 1240 cm$^{-1}$
NMR (DMSO-d$_6$, δ): 3.93 (6H, s), 7.54 (1H, d, J=5.0 Hz), 8.24 (1H, d, J=5.0 Hz), 8.33 (2H, d, J=1.7 Hz), 8.54 (1H, dd, J=1.7, 1.7 Hz), 9.78 (1H, s)
(+) APCI MASS: 305 (M+H)$^+$

(10) Dimethyl 5-(furan-3-yl)isophthalate
mp: 141–143° C.
IR (Nujol): 1720, 1610, 1510, 1350, 1240 cm$^{-1}$
NMR (DMSO-d$_6$, δ): 3.92 (6H, s), 7.11 (1H, d, J=1.8 Hz), 7.81 (1H, dd, J=1.8, 1.6 Hz), 8.34 (1H, d, J=1.6 Hz), 8.35 (2H, s), 8.45 (1H, s)
(+) APCI MASS: 261 (M+H)$^+$
Elemental Analysis Calcd. for $C_{14}H_{12}O_5$: C 64.61, H 4.65
Found: C 64.30, H 4.52

(11) Methyl 5-(2-difluoromethylbenzofuran-4-yl)-3-[(2-dimethylaminoethyl)carbamoyl]benzoate
IR (Film): 3260, 1718, 1645 cm$^{-1}$
NMR (DMSO-d$_6$, δ): 2.20 (6H, s), 2.45 (2H, t, J=6.8 Hz), 3.30–3.48 (2H, m), 3.94 (3H, s), 7.33 (1H, t, J=52.6 Hz), 7.46–7.49 (1H, m), 7.55–7.75 (2H, m), 7.78–7.88 (1H, m), 8.28 (1H, s), 8.37 (1H, s), 8.50 (1H, s), 8.79 (1H, t, J=5.5 Hz)

PREPARATION 71

The following compounds were obtained according to a similar manner to that of Preparation 26-(1)

(1) Dimethyl 5-(2-difluoromethylbenzofuran-3-yl)isophthalate
mp: 146–148° C.
IR (Nujol):; 1720, 1610, 1410, 1250 cm$^{-1}$
NMR (DMSO-d$_6$, δ): 3.94 (6H, s), 7.31 (1H, t, J=51.6 Hz), 7.45 (1H, dd, J=7.8, 7.2 Hz), 7.59 (1H, dd, J=8.2, 7.2

Hz), 7.68 (1H, d, J=7.8 Hz), 7.84 (1H, d, J=8.2 Hz), 8.31 (2H, d, J=1.6 Hz), 8.58 (1H, dd, J=1.6, 1.6 Hz)

Elemental Analysis Calcd. for $C_{19}H_{14}F_2O_5$: C 63.34, H 3.92 Found: C 63.89, H 3.88

(2) Dimethyl 5-(2-difluoromethylbenzo[b]thiophen-3-yl) isophthalate mp: 148–150° C.

IR (Nujol): 1720, 1300, 1250 cm$^{-1}$

NMR (DMSO-d$_6$, δ): 3.93 (6H, s), 7.20 (1H, t, J=53.7 Hz), 7.50–7.62 (3H, m), 8.20 (1H, d, J=7.0 Hz), 8.22 (2H, d, J=1.6 Hz), 8.61 (1H, dd, J=1.6, 1.6 Hz)

Elemental Analysis Calcd. for $C_{19}H_{14}F_2O_4S$: C 60.63, H 3.75 Found: C 60.72, H 3.62

(3) Methyl 3-(2-difluoromethylbenzo[b]thiophen-3-yl) benzoate mp:70–72° C.

IR (Nujol): 1720, 1530, 1270 cm$^{-1}$

NMR (DMSO-d$_6$, δ): 3.90 (3H, s), 7.17 (1H, t, J=53.8 Hz), 7.45–7.62 (3H, m), 7.75–7.78 (2H, m), 8.00 (1H, s), 8.10–8.21 (2H, m)

Elemental Analysis Calcd. for $C_{17}H_{12}F_2O_2S$: C 64.14, H 3.80 Found: C 64.30, H 3.66

(4) Dimethyl 5-(2-difluoromethylthiophen-3-yl)isophthalate mp: 142–144° C.

IR (Nujol): 1710, 1600, 1320, 1250 cm$^{-1}$

NMR (DMSO-d$_6$, δ): 3.93 (6H, s), 7.20 (1H, t, J=54.1 Hz), 7.42 (1H, d, J=5.1 Hz), 7.96 (1H, d, J=5.1 Hz), 8.21 (2H, d, J=1.6 Hz), 8.51 (1H, dd, J=1.6, 1.6 Hz)

Elemental Analysis Calcd. for $C_{15}H_{12}F_2O_4S$: C 55.21, H 3.71 Found: C 55.42, H 3.54

(5) Dimethyl 5-(2-difluoromethylfuran-3-yl)isophthalate mp: 122–124° C.

IR (Nujol): 1720, 1250 cm$^{-1}$

NMR (DMSO-d$_6$, δ): 3.93 (6H, s), 7.08 (1H, d, J=1.8 Hz), 7.20 (1H, t, J=51.9 Hz), 8.02 (1H, d, J=1.8 Hz), 8.23 (2H, d, J=1.6 Hz), 8.48 (1H, dd, J=1.6, 1.6 Hz)

Elemental Analysis Calcd. for $C_{15}H_{12}F_2O_5$: C 58.07, H 3.90 Found: C 58.37, H 3.67

(6) 2-Difluoromethyl-4-iodobenzofuran mp: 38–39° C.

IR (Nujol): 1608 cm$^{-1}$

NMR (DMSO-d$_6$, δ): 7.20–7.25 (1H, m), 7.28 (1H, dd, J=7.9, 7.9 Hz), 7.30 (1H, t, J=52.6 Hz), 7.77 (2H, d, J=7.9 Hz)

PREPARATION 72

The following compounds were obtained according to a similar manner to that of Preparation 41.

(1) 5-(2-Difluoromethylbenzofuran-3-yl)-3-methoxycarbonylbenzoic acid mp: 212–214° C. (dec.)

IR (Nujol): 1720, 1690, 1600, 1260 cm$^{-1}$

NMR (DMSO-d$_6$, δ): 3.94 (3H, s), 7.30 (1H, t, J=51.6 Hz), 7.45 (1H, dd, J=7.5, 7.5 Hz), 7.59 (1H, dd, J=8.2, 7.5 Hz), 7.68 (1H, d, J=7.5 Hz), 7.83 (1H, d, J=8.2 Hz), 8.27 (1H, dd, J=1.6, 1.6 Hz), 8.30 (1H, dd, J=1.6, 1.6 Hz), 8.59 (1H, dd, J=1.6, 1.6 Hz)

Elemental Analysis Calcd. for $C_{18}H_{12}F_2O_5$: C 62.43, H 3.49 Found: C 62.50, H 3.46

(2) 5-(2-Difluoromethylbenzo[b]thiophen-3-yl)-3-methoxycarbonylbenzoic acid mp: 193–195° C.

IR (Nujol): 1720, 1680, 1600 cm$^{-1}$

NMR (DMSO-d$_6$, δ): 3.93 (3H, s), 7.19 (1H, t, J=53.8 Hz), 7.50–7.62 (3H, m), 8.16–8.22 (3H, m), 8.62 (1H, dd, J=1.7, 1.7 Hz)

Elemental Analysis Calcd. for $C_{18}H_{12}F_2O_4S$: C 59.67, H 3.34 Found: C 59.35, H 3.27

(3) 5-(2-Difluoromethylthiophen-3-yl)-3-methoxycarbonylbenzoic acid mp: 166–168° C.

IR (Nujol): 1730, 1690, 1600, 1270 cm$^{-1}$

NMR (DMSO-d$_6$, δ): 3.92 (3H, s), 7.20 (1H, t, J=54.2 Hz), 7.41 (1H, d, J=5.1 Hz), 7.95 (1H, d, J=5.1 Hz), 8.18 (1H, dd, J=1.7, 1.7 Hz), 8.20 (1H, dd, J=1.7, 1.7 Hz), 8.51 (1H, dd, J=1.7, 1.7 Hz)

Elemental Analysis Calcd. for $C_{14}H_{10}F_2O_4S$: C 53.85, H 3.23 Found: C 53.82, H 3.08

(4) 5-(2-Difluoromethylfuran-3-yl)-3-methoxycarbonylbenzoic acid mp: 130° C. (dec.)

IR (Nujol): 1720, 1690, 1330, 1250 cm$^{-1}$

NMR (DMSO-d$_6$, δ): 3.93 (3H, s), 7.07 (1H, d, J=1.7 Hz), 7.20 (1H, t, J=52.0 Hz), 8.02 (1H, d, J=1.7 Hz), 8.21 (1H, dd, J=1.5, 1.5 Hz), 8.23 (1H, dd, J=1.5, 1.5 Hz), 8.48 (1H, dd, J=1.5, 1.5 Hz), 13.47 (1H, br s)

Elemental Analysis Calcd. for $C_{14}H_{10}F_2O_5$: C 56.77, H 3.40 Found: C 56.79, H 3.36

PREPARATION 73

The following compounds were obtained according to a similar manner to that of Preparation 42.

(1) Methyl 5-(2-difluoromethylbenzofuran-3-yl)-3-[(2-dimethylaminoethyl)carbamoyl]benzoate IR (benzene): 3300, 1720, 1660, 1250 cm$^{-1}$ NMR (DMSO-d$_6$, δ): 2.20 (6H, s), 2.44 (2H, t, J=6.8 Hz), 3.37–3.47 (2H, m), 3.95 (3H, s), 7.31 (1H, t, J=51.4 Hz), 7.45 (1H, dd, J=7.7, 7.3 Hz), 7.59 (1H, dd, J=8.2, 7.3 Hz), 7.70 (1H, d, J=7.7 Hz), 7.84 (1H, d, J=8.2 Hz), 8.19 (1H, dd, J=1.5, 1.5 Hz), 8.28 (1H, dd, J=1.5, 1.5 Hz), 8.57 (1H, dd, J=1.5, 1.5 Hz), 8.79 (1H, t, J=5.5 Hz)

(+) APCI MASS: 417 (M+H)$^+$ (2) Methyl 5-(2-difluoromethylbenzo[b]thiophen-3-yl)-3-[(2-dimethylaminoethyl)carbamoyl]benzoate IR (Nujol): 1720, 1630, 1250 cm$^{-1}$ NMR (DMSO-d$_6$, δ): 2.18 (6H, s), 2.42 (2H, t, J=6.8 Hz), 3.35–3.45 (2H, m), 3.93 (3H, s), 7.20 (1H, t, J=53.7 Hz), 7.50–7.63 (3H, m), 8.10 (1H, dd, J=1.6, 1.6 Hz), 8.18–8.22 (2H, m), 8.60 (1H, dd, J=1.6, 1.6 Hz), 8.75 (1H, t, J=5.6 Hz)

(+) APCI MASS: 433 (M+H)$^+$ (3) Methyl 5-(2,5-dichlorothiophen-3-yl)-3-[(4-methylpiperazin-1-yl)carbamoyl]benzoate mp: 193–195° C.

IR (Nujol): 3150, 1720, 1640, 1540, 1260, 1210 cm$^{-1}$

NMR (DMSO-d$_6$, δ): 2.20 (3H, s), 2.39–2.45 (4H, m), 2.90 (4H, t, J=4.6 Hz), 3.92 (3H, s), 7.53 (1H, s), 8.19 (1H, s), 8.27 (1H, s), 8.38 (1H, s), 9.68 (1H, s)

(+) APCI MASS: 428 (M+H)$^+$, 430 (M+H)$^+$ (4) Methyl 5-(2-difluoromethylthiophen-3-yl)-3-[(2-dimethylaminoethyl)carbamoyl]benzoate IR (benzene): 3300, 1720, 1530, 1250 cm$^{-1}$ NMR (DMSO-d$_6$, δ): 2.18 (6H, s), 2.42 (2H, t, J=6.8 Hz), 3.34–3.44 (2H, m), 3.92 (3H, s), 7.21 (1H, t, J=54.1 Hz), 7.40 (1H, d, J=5.1 Hz), 7.96 (1H, d, J=5.1 Hz), 8.08 (1H, dd, J=1.6, 1.6 Hz), 8.16 (1H, dd, J=1.6, 1.6 Hz), 8.46 (1H, dd, J=1.6, 1.6 Hz), 8.73 (1H, t, J=5.5 Hz)

(+) APCI MASS: 383 (M+H)$^+$ (5) Methyl 5-(2-difluoromethylfuran-3-yl)-3-[(2-dimethylaminoethyl)carbamoyl]benzoate hydrochloride mp: 166–168° C.

IR (Nujol): 3300, 2600, 1720, 1670, 1550, 1270 cm$^{-1}$

NMR (DMSO-d$_6$, δ): 2.83 (6H, s), 3.24–3.34 (2H, m), 3.64–3.74 (2H, m), 3.92 (3H, s), 7.13 (1H, d, J=1.7 Hz), 7.27 (1H, t, J=51.8 Hz), 8.03 (1H, d, J=1.7 Hz), 8.15 (1H, dd, J=1.5, 1.5 Hz), 8.32 (1H, dd, J=1.5, 1.5 Hz), 8.47 (1H, dd, J=1.5, 1.5 Hz), 9.22 (1H, t, J=5.5 Hz), 10.23 (1H, s)

(+) APCI MASS: 367 (M+H)$^+$

Elemental Analysis Calcd. for C$_{18}$H$_{20}$F$_2$N$_2$O$_4$·HCl C 53.67, H 5.25, N 6.95 Found: C 54.17, H 5.26, N 6.88

(6) Methyl 5-(2-difluoromethylfuran-3-yl)-3-[(4-methylpiperazin-1-yl)carbamoyl]benzoate hydrochloride
mp: 155° C. (dec.)

IR (Nujol): 3350 (br), 1720, 1650, 1250 cm$^{-1}$

NMR (DMSO-d$_6$, δ): 2.77 (3H, s), 3.15–3.50 (8H, m), 3.92 (3H, s), 7.08 (1H, d, J=1.8 Hz), 7.23 (1H, t, J=51.8 Hz), 8.02 (1H, d, J=1.8 Hz), 8.13 (1H, dd, J=1.5, 1.5 Hz), 8.16 (1H, dd, J=1.5, 1.5 Hz), 8.40 (1H, dd, J=1.5, 1.5 Hz), 10.22 (1H, s), 11.04 (1H, s)

(+) APCI MASS: 394 (M+H)$^+$ (7) Methyl 3-[(2-diethylaminoethyl)carbamoyl]-5-(2-difluoromethylfuran-3-yl)benzoate IR (Neat): 3300, 1720, 1650, 1250 cm$^{-1}$ NMR (DMSO-d$_6$, δ): 0.98 (6H, t, J=7.1 Hz), 2.46–2.61 (6H, m), 3.30–3.40 (2H, m), 3.92 (3H, s), 7.04 (1H, d, J=1.8 Hz), 7.20 (1H, t, J=51.8 Hz), 8.02 (1H, d, J=1.8 Hz), 8.11 (1H, dd, J=1.6, 1.6 Hz), 8.14 (1H, dd, J=1.6, 1.6 Hz), 8.43 (1H, dd, J=1.6, 1.6 Hz), 8.73 (1H, t, J=5.7 Hz)

(+) APCI MASS: 395 (M+H)$^+$ (8) Methyl 5-(2-difluoromethylbenzofuran-3-yi)-3-[(2-diethylaminoethyl)carbamoyl]benzoate IR (Neat): 3300, 1720, 1650, 1540 cm$^{-1}$ NMR (DMSO-d$_6$, δ): 0.97 (6H, t, J=7.1 Hz), 2.46–2.61 (6H, m), 3.26–3.36 (2H, m), 3.94 (3H, s), 7.31 (1H, t, J=51.4 Hz), 7.45 (1H, dd, J=7.6, 7.6 Hz), 7.60 (1H, dd, J=7.6, 7.6 Hz), 7.70 (1H, d, J=7.6 Hz), 7.84 (1H, d, J=7.6 Hz), 8.18 (1H, dd, J=1.5, 1.5 Hz), 8.26 (1H, dd, J=1.5, 1.5 Hz), 8.55 (1H, dd, J=1.5, 1.5 Hz), 8.78 (1H, t, J=5.5 Hz)

(+) APCI MASS: 445 (M+H)$^+$ (9) Methyl 5-(2-difluoromethylbenzofuran-3-yl)-3-[(1-hydroxymethyl-2-hydroxyethyl)carbamoyl]benzoate
mp: 152–154° C.

IR (Nujol): 3400, 3300, 1720, 1650, 1540, 1280, 1260 cm$^{-1}$

NMR (DMSO-d$_6$, δ): 3.56 (4H, dd, J=5.7, 8.0 Hz), 3.95 (3H, s), 3.95–4.15 (1H, m), 4.71 (2H, t, J=5.7 Hz), 7.28 (1H, t, J=51.5Hz), 7.46 (1H, dd, J=7.8, 7.8 Hz), 7.60 (1H, dd, J=7.8, 7.8 Hz), 7.70 (1H, d, J=7.8 Hz), 7.84 (1H, d, J=7.8 Hz), 8.18 (1H, dd, J=1.5, 1.5 Hz), 8.32 (1H, dd, J=1.5, 1.5 Hz), 8.43 (1H, d, J=8.0 Hz), 8.60 (1H, dd, J=1.5, 1.5 Hz)

(+) APCI MASS: 420 (M+H)$^+$

(10) Methyl 5-(2-difluoromethylbenzofuran-3-yl)-3-[(3-dimethylaminopropyl)carbamoyl]benzoate hydrochloride
mp: 172–174° C.

IR (Nujol): 3250, 2650, 1730, 1660, 1530, 1250, 1210 cm$^{-1}$

NMR (DMSO-d$_6$, δ): 1.90–2.05 (2H, m), 2.74 (6H, s), 3.11 (2H, t, J=7.7 Hz), 3.35–3.45 (2H, m), 3.94 (3H, s), 7.36 (1H, t, J=51.3 Hz), 7.46 (1H, dd, J=7.6, 7.6 Hz), 7.60 (1H, dd, J=7.6, 7.6 Hz), 7.73 (1H, d, J=7.6 Hz), 7.85 (1H, d, J=7.6 Hz), 8.20 (1H, dd, J=1.5, 1.5 Hz), 8.32 (1H, dd, J=1.5, 1.5 Hz), 8.58 (1H, dd, J=1.5, 1.5 Hz), 9.09 (1H, t, J=5.5 Hz), 10.53 (1H, s)

(+) APCI MASS: 431 (M+H)$^+$

(11) Methyl 5-(2-difluoromethylbenzofuran-3-yl)-3-[(4-methylpiperazin-1-yl)carbamoyl]benzoate
mp: 174–176° C.

IR (Nujol): 3200, 1730, 1640, 1550, 1260, 1210 cm$^{-1}$

NMR (DMSO-d$_6$, δ): 2.19 (3H, s), 2.38–2.48 (4H, m), 2.92 (4H, t, J=4.6 Hz), 3.94 (3H, s), 7.32 (1H, t, J=51.4 Hz), 7.45 (1H, dd, J=7.5, 7.5 Hz), 7.59 (1H, dd, J=7.5, 7.5 Hz), 7.71 (1H, d, J=7.5 Hz), 7.84 (1H, d, J=7.5 Hz), 8.18–8.20 (2H, m), 8.49 (1H, dd, J=1.5, 1.5 Hz), 9.78 (1H, s)

(+) APCI MASS: 444 (M+H)$^+$

(12) Methyl 5-(3,5-dichlorophenyl)-3-[(4-methylpiperazin-1-yl)carbamoyl]benzoate
mp: 214–216° C.

IR (Nujol): 3150, 1730, 1640, 1270, 1240, 900, 795 cm$^{-1}$

NMR (DMSO-d$_6$, δ): 2.23 (3H, s), 2.35–2.60 (4H, m), 2.9–3.0 (4H, m), 3.93 (3H, s), 7.7 (1H, s), 7.88 (2H, s), 8.3–8.4 (3H, m), 9.76 (1H, s)

(+) APCI MASS: 422 (M+H)$^+$, 424 (M+H)$^+$

(13) Methyl 5-(2,5-dichlorothiophen-3-yl)-3-[(3-diethylaminopropyl)carbamoyl]benzoate IR (Film): 720, 1030, 905, 825 cm$^{-1}$ NMR (DMSO-d$_6$, δ): 0.96 (6H, t, J=7.1 Hz), 1.55–1.8 (2H, m), 2.3–2.6 (4H, m), 3.2–3.4 (4H, m), 3.92 (3H, s), 7.53 (1H, s), 8.27 (2H, s), 8.44 (1H, s), 8.82 (1H, s)

(+) APCI MASS: 443 (M+H)$^+$, 445 (M+H)$^+$

(14) Methyl 5-(2,5-dichlorothiophen-3-yl)-3-[(3-dimethylaminopropyl)carbamoyl]benzoate IR (Film): 3300, 1720, 1635, 1030, 990, 910 cm$^{-1}$ NMR (DMSO-d$_6$, δ): 1.6–1.8 (2H, m), 2.14 (6H, s), 2.27 (2H, t, J=7.1 Hz), 3.2–3.4 (2H, m), 3.92 (3H, s), 7.53 (1H, s), 8.27 (2H, s), 8.45 (1H, s), 8.82 (1H, m)

(+) APCI MASS: 415 (M+H)$^+$, 417 (M+H)$^+$

(15) Methyl 5-(2,5-dichlorothiophen-3-yl)-3-[(2-diethylaminoethyl)carbamoyl]benzoate NMR (DMSO-d$_6$, δ): 0.97 (6H, t, J=7.1 Hz), 2.4–2.65 (6H, m), 3.3–3.45 (2H, m), 3.92 (3H, s), 7.51 (1H, s), 8.26 (2H, s), 8.45 (1H, s), 8.69 (1H, t, J=5.5 Hz)

PREPARATION 74

The following compound was obtained according to a similar manner to that of Preparation 23.

Methyl 5-(2-chlorobenzofuran-3-yl)-3-[(2-dimethylaminoethyl)carbamoyl]benzoate mp: 114–116° C.

IR (Nujol): 3250, 1720, 1640, 1550, 1270 cm$^{-1}$

NMR (DMSO-d$_6$, δ): 2.20 (6H, s), 2.44 (2H, t, J=6.8 Hz), 3.36–3.46 (2H, m), 3.95 (3H, s), 7.41 (1H, dd, J=7.3, 7.3 Hz), 7.48 (1H, dd, J=7.3, 7.1 Hz), 7.68 (1H, d, J=7.3 Hz), 7.72 (1H, d, J=7.1 Hz), 8.32 (1H, dd, J=1.6, 1.6 Hz), 8.39 (1H, dd, J=1.6, 1.6 Hz), 8.52 (1H, dd, J=1.6, 1.6 Hz), 8.78 (1H, t, J=5.5 Hz)

(+) APCI MASS: 401 (M+H)$^+$, 403 (M+H)$^+$

Elemental Analysis Calcd. for C$_{21}$H$_{21}$ClN$_2$O$_4$: C 62.92, H 5.28, N 6.99 Found: C 62.80, H 5.30, N 6.84

PREPARATION 75

The following compound was obtained according to a similar manner to that of Preparation 24.

Dimethyl 5-(2-formylfuran-3-yl)isophthalate mp: 150–153° C.

IR (Nujol): 1720, 1680, 1250 cm$^{-1}$

NMR (DMSO-d$_6$, δ): 3.93 (6H, s), 7.24 (1H, d, J=1.8 Hz), 8.22 (1H, d, J=1.8 Hz), 8.46–8.51 (3H, m), 9.73 (1H, s)

(+) APCI MASS: 289 (M+H)$^+$

Elemental Analysis Calcd. for C$_{15}$H$_{12}$O$_6$: C 62.50, H 4.20 Found: C 62.28, H 4.17

PREPARATION 76

The following compound was obtained according to a similar manner to that of Preparation 37.

2-Hydroxymethyl-4-iodobenzofuran mp: 81–83° C.

IR (Nujol): 3260 cm$^{-1}$

NMR (DMSO-d$_6$, δ): 4.59 (2H, d, J=5.9 Hz), 5.54 (1H, t, J=5.9 Hz), 6.58 (1H, s), 7.09 (1H, dd, J=8.0 Hz, 8.0 Hz), 7.55–7.66 (2H, m)

PREPARATION 77

The following compound was obtained according to a similar manner to that of Preparation 38.

4-Iodo-2-benzofurancarbaldehyde mp: 83–84° C.

IR (Nujol): 1673 cm$^{-1}$

NMR (DMSO-d$_6$, δ): 7.38 (1H, dd, J=8.2, 8.2 Hz), 7.76–7.86 (3H, m), 9.89 (1H, s)

PREPARATION 78

The following compound was obtained according to a similar manner to that of Preparation 4.

(2-Difluoromethylbenzofuran-4-yl)dihydroxyborane mp: 117° C. (dec.)

IR (DMSO-d$_6$): 3300 (br), 1610 cm$^{-1}$

NMR (DMSO-d$_6$, δ): 7.29 (1H, t, J=52.9 Hz), 7.33–7.40 (2H, m), 7.71 (1H, d, J=7.6 Hz), 7.80 (1H, d, J=7.6 Hz), 8.24 (2H, br s)

PREPARATION 79

The following compound was obtained according to a similar manner to that of Preparation 6.

5-(3,5-Dichlorophenyl)-3-methoxycarbonylbenzoic acid mp: 204–206° C.

IR (Nujol): 3250, 1735, 1700, 1310, 1190, 990 cm$^{-1}$

NMR (DMSO-d$_6$, δ): 3.93 (3H, s), 7.73 (1H, s), 7.80 (2H, s), 8.34 (1H, s), 8.40 (1H, s), 8.51 (1H, s)

PREPARATION 80

The following compound was obtained according to a similar manner to that of Preparation 8 or 9.

Methyl 5-(2,5-dichlorothiophen-3-yl)-3-[(2-dimethylaminoethyl)carbamoyl]benzoate.

IR (Neat): 3300, 2950, 1720, 1640, 1530, 1440 cm$^{-1}$

NMR (DMSO-d$_6$, δ): 2.19 (6H, s), 2.42 (2H, t, J=6.8 Hz), 3.34–3.44 (2H, m), 3.92 (3H, s), 7.53 (1H, s), 8.27 (2H, dd, J=1.6, 1.6 Hz), 8.45 (1H, dd, J=1.6, 1.6 Hz), 8.72 (1H, , J=5.6 Hz)

(+) APCI MASS: 401 (M+H)$^+$

PREPARATION 81

The following compound was obtained according to a similar manner to that of Preparation 61.

Methyl 5-hydroxy-3-[(2-pyrrolidinoethyl)carbamoyl]benzoate mp: 113–115° C.

IR (Nujol): 3350, 1710, 1630, 1590, 1540, 1230 cm$^{-1}$

NMR (DMSO-d$_6$, δ): 1.65–1.75 (4H, m), 2.45–2.55 (4H, m), 2.57 (2H, t, J=6.9 Hz), 3.30–3.45 (2H, m), 3.87 (3H, s), 7.48 (1H, dd, J=1.4, 1.4 Hz), 7.50 (1H, dd, J=1.4, 1.4 Hz), 7.89 (1H, dd, J=1.4, 1.4 Hz), 8.59 (1H, t, J=5.5 Hz), 10.13 (1H, br s)

(+) APCI MASS: 293 (M+H)$^+$

PREPARATION 82

The following compound was obtained according to a similar manner to that of Preparation 62 or 63.

Methyl 3-[(2-pyrrolidinoethyl)carbamoyl]-5-trifluoromethylsulfonyloxybenzoate

IR (Neat): 3300, 2950, 1730, 1640, 1540, 1420 cm$^{-1}$

NMR (DMSO-d$_6$, δ): 1.65–1.75 (4H, m), 2.50–2.58 (4H, m), 2.61 (2H, t, J=6.8 Hz), 3.38–3.48 (2H, m), 3.94 (3H, s), 8.13 (1H, dd, J=1.4, 1.4 Hz), 8.22 (1H, dd, J=1.4, 1.4 Hz), 8.56 (1H, dd, J=1.4, 1.4 Hz), 8.95 (1H, t, J=5.5 Hz)

PREPARATION 83

The following compounds were obtained according to a similar manner to that of Preparation 42.

(1) Methyl 5-(2,5-dichlorothiophen-3-yl)-3-[(2-pyrrolidinoethyl)carbamoyl]benzoate hydrochloride mp: 70–72° C.

IR (Nujol): 3400 (br), 1720, 1640, 1540, 1280 cm$^{-1}$

NMR (DMSO-d$_6$, δ): 1.80–2.10 (4H, m), 2.95–3.10 (2H, m), 3.30–3.42 (2H, m), 3.57–3.70 (4H, m), 3.92 (3H, s), 7.65 (1H, s), 8.33 (1H, dd, J=1.5, 1.5 Hz), 8.44 (1H, dd, J=1.5, 1.5 Hz), 8.49 (1H, dd, J=1.5, 1.5 Hz), 9.24 (1H, t, J=5.5 Hz), 10.69 (1H, s)

(+) APCI MASS: 427 (M+H)$^+$, 429 (M+H)$^+$ (2) Methyl 5-(2-difluoromethylthiophen-3-yl)-3-[(4-methylpiperazin-1-yl)carbamoyl]benzoate mp: 165–168° C.

IR (Nujol): 3150, 1720, 1640, 1540, 1330, 1240 cm$^{-1}$

NMR (DMSO-d$_6$, δ): 2.19 (3H, s), 2.37–2.47 (4H, m), 2.85–2.95 (4H, m), 3.92 (3H, s), 7.22 (1H, t, J=54.0 Hz), 7.41 (1H, d, J=5.1 Hz), 7.96 (1H, d, J=5.1 Hz), 8.08 (1H, s), 8.09 (1H, s), 8.40 (1H, s), 9.72 (1H, s)

(3) Methyl 5-(2,5-dichlorothiophen-3-yl)-3-[(2-piperidinoethyl)carbamoyl]benzoate hydrochloride mp: 170–171° C.

IR (Nujol): 1725, 1665, 1590, 1025, 720 cm$^{-1}$

NMR (DMSO-d$_6$, δ): 1.2–1.6 (1H, br), 1.6–2.0 (5H, m), 2.8–3.1 (2H, m), 3.2–3.35 (2H, m), 3.4–3.65 (2H, m), 3.65–3.8 (2H, m), 3.92 (3H, s), 7.64 (1H, s), 8.33 (1H, s), 8.43 (1H, s), 8.49 (1H, s), 9.29 (1H, m), 10.37 (1H, br s)

(+) APCI MASS: 441 (M+H)$^+$, 443 (M+H)$^+$

EXAMPLE 1

To a solution of guanidine hydrochloride (0.87 g) in N,N-dimethylformamide (5 ml) was added sodium methoxide (1.6 ml, 28% in methanol) under nitrogen atmosphere. After being stirred for 30 minutes at room temperature, to the reaction mixture was added a solution of 2-methyl-2-trifluoromethylsulfonylaminopropyl 3-(3,4-dihydro-1-naphthyl)benzoate (0.59 g) in N,N-dimethylformamide (5 ml). After being stirred for 21 hours at room temperature, the reaction mixture was poured into a mixture of ethyl acetate and water. The organic layer was successively washed with brine and dried over magnesium sulfate. The solvent was evaporated in vacuo, and the residue was dissolved in ethyl acetate and crystallized from slight excess 4N-hydrogen chloride-ethyl acetate. The crystalline was triturated with diethyl ether to give [3-(3,4-dihydro-1-naphthyl)benzoyl] guanidine hydrochloride (0.25 g).

mp: 168–170° C.

IR (Nujol): 3200, 1720, 1690, 1570 cm$^{-1}$

NMR (DMSO-d$_6$, δ): 2.3–2.5 (2H, m), 2.7–2.9 (2H, m), 6.29 (1H, t, J=4.6 Hz), 6.8–6.9 (1H, m), 7.1–7.4 (3H, m), 7.6–7.7 (2H, m), 8.0–8.2 (2H, m), 8.63 (2H, br s), 8.76 (2H, br s), 12.08 (1H, s)

(+) APCI MASS: 292 (M+H)$^+$

Elemental Analysis Calcd. for $C_{18}H_{17}N_3O \cdot HCl$: C 65.95, H 5.53, N 12.82 Found: C 65.97, H 5.59, N 12.66

EXAMPLE 2

To a solution of guanidine hydrochloride (1.54 g) in N,N-dimethylformamide (5 ml) was added sodium methoxide (2.8 ml, 28% in methanol) under nitrogen atmosphere. After being stirred for 30 minutes at room temperature, to the reaction mixture was added a solution of 2-methyl-2-trifluoromethylsulfonylaminopropyl 3-(1H-inden-3-yl)benzoate (1.01 g) in N,N-dimethylformamide (5 ml). After being stirred for 23 hours at room temperature, the reaction mixture was poured into a mixture of ethyl acetate and water. The organic layer was successively washed with brine and dried over magnesium sulfate. The solvent was evaporated in vacuo and the residue was purified by column chromatography on silica gel eluting with a mixture of chloroform and methanol (10:1). The eluted fractions containing the desired product were collected and evaporated in vacuo. The residue was dissolved in ethanol and crystallized from slight excess methanesulfonic acid. The crystalline was recrystallized from ethanol to give [3-(1H-inden-3-yl)benzoyl]guanidine methanesulfonate (0.22 g).

mp: 192–194° C.

IR (Nujol): 3350, 3120, 1710, 1650, 1590 cm$^{-1}$

NMR (DMSO-d$_6$, δ): 2.39 (3H, s), 3.5–3.7 (2H, m), 6.8–6.9 (1H, m), 7.2–8.2 (8H, m), 8.44 (4H, br s), 11.36 (1H, s)

(+) APCI MASS: 278 (M+H)$^+$

Elemental Analysis Calcd. for $C_{17}H_{15}N_3O \cdot CH_4O_3S$: C 56.53, H 5.27, N 10.99 Found: C 56.72, H 5.09, N 10.81

EXAMPLE 3

To a solution of guanidine hydrochloride (1.33 g) in N,N-dimethylformamide (7 ml) was added sodium methoxide (2.4 ml, 28% in methanol) under nitrogen atmosphere. After being stirred for 15 minutes at room temperature, to the reaction mixture was added a solution of methyl 3-(benzofuran-4-yl)benzoate (0.7 g) in N,N-dimethylformamide (5 ml). After being stirred for 18 hours at room temperature, the solvent was evaporated in vacuo. The residue was dissolved in a mixture of ethyl acetate (50 ml) and water (50 ml). The organic layer was successively washed with 10% sodium hydroxide aqueous solution, brine and dried over magnesium sulfate. After being evaporated in vacuo, the residue was dissolved in ethanol and crystallized from slight excess methanesulfonic acid. The crystalline was recrystallized from ethanol to give [3-(benzofuran-4-yl)benzoyl]guanidine methanesulfonate (0.85 g).

mp: 208–210° C.

IR (Nujol): 3325, 3100, 1710, 1040 cm$^{-1}$

NMR (DMSO-d$_6$, δ): 2.38 (3H, s), 7.14–7.15 (1H, m), 7.43–7.52 (2H, m), 7.66–7.82 (2H, m), 7.98–8.04 (2H, m), 8.13–8.19 (2H, m), 8.2–8.4 (4H, br), 11.36 (1H, s)

(+) APCI MASS: 280 (M+H)$^+$

Elemental Analysis Calcd. for $C_{17}H_{17}N_3O_5S$: C 54.39, H 4.56, N 11.19 Found: C 54.03, H 4.71, N 10.93

EXAMPLE 4

The following compounds were obtained according to similar manners to those of Examples 1, 2 and 3.

(1) [3-(6,7-Dihydro-5H-benzocyclohepten-9-yl)benzoyl]guanidine hydrochloride mp: 207–208° C.

IR (Nujol): 3300, 1690, 1620, 1560 cm$^{-1}$

NMR (DMSO-d$_6$, δ): 1.8–2.2 (4H, m), 2.5–2.7 (2H, m), 6.72 (1H, t, J=7.2 Hz), 6.8–7.0 (1H, m), 7.2–7.6 (5H, m), 8.0–8.2 (2H, m), 8.61 (2H, br s), 8.79 (2H, br s), 12.16 (1H, s)

(+) APCI MASS: 306 (M+H)$^+$

Elemental Analysis Calcd. for $C_{19}H_{19}N_3O \cdot HCl$: C 66.76, H 5.90, N 12.29 Found: C 67.17, H 5.97, N 12.27

(2) [3-(6-Fluoro-2H-1-benzopyran-4-yl)benzoyl]guanidine methanesulfonate mp: 200–201° C.

IR (Nujol): 3320, 1700, 1635, 1580 cm$^{-1}$

NMR (DMSO-d$_6$, δ): 2.39 (3H, s), 4.86 (2H, d, J=3.9 Hz), 6.17 (1H, t, J=3.9 Hz), 6.64 (1H, dd, J=2.9, 9.4 Hz), 6.9–7.0 (2H, m), 7.6–8.1 (4H, m), 8.39 (4H, br s)

(+) APCI MASS: 312 (M+H)$^+$

Elemental Analysis Calcd. for $C_{17}H_{14}FN_3O_2 \cdot CH_4O_3S$: C 53.07, H 4.45, N 10.31 Found: C 53.02, H 4.40, N 10.26

(3) [3-(4aRS,8aSR)-3,4,4a,5,6,7,8,8a-Octahydro-1-naphthyl)benzoyl]guanidine methanesulfonate mp: 194–195° C.

IR (Nujol): 3320, 3120, 1700, 1650, 1590 cm$^{-1}$

NMR (DMSO-d$_6$, δ): 0.5–0.8 (1H, m), 1.1–1.9 (10H, m), 2.1–2.5 (3H, m), 2.40 (3H, s), 5.82 (1H, m), 7.4–7.9 (4H, m), 8.39 (4H, br s), 11.22 (1H, s)

(+) APCI MASS: 298 (M+H)$^+$

Elemental Analysis Calcd. for $C_{18}H_{23}N_3O \cdot CH_4O_3S$: C 57.99, H 6.92, N 10.68 Found: C 58.04, H 6.81, N 10.62

(4) [3-(1-Phenylvinyl)benzoyl]guanidine methanesulfonate mp: 156–158° C.

IR (Nujol): 3350, 1700, 1600 cm$^{-1}$

NMR (DMSO-d$_6$, δ): 2.39 (3H, s), 5.64 (2H, d, J=4.5 Hz), 7.2–8.0 (9H, m), 8.35 (2H, br s), 8.50 (2H, br s), 11.33 (1H, s)

(+) APCI MASS: 266 (M+H)$^+$

Elemental Analysis Calcd. for $C_{16}H_{15}N_3O \cdot CH_4O_3S$: C 56.50, H 5.30, N 11.63 Found: C 56.64, H 5.27, N 11.56

(5) [3-(2-Methoxymethyl-3,4-dihydro-1-naphthyl)benzoyl]guanidine methanesulfonate mp: 166–168° C.

IR (Nujol): 3350, 3300, 1715, 1690, 1600 cm$^{-1}$

NMR (DMSO-d$_6$, δ): 2.36 (3H, s), 2.4–2.5 (2H, m), 2.8–3.0 (2H, m), 3.13 (3H, s), 3.79 (2H, s), 6.44 (1H, d, J=7.4 Hz), 7.0–7.3 (3H, m), 7.52 (1H, d, J=7.7 Hz), 7.6–7.8 (2H, m), 8.01 (1H, d, J=8.2 Hz), 8.35 (2H, br s), 8.47 (2H, br s), 11.22 (1H, s)

(+) APCI MASS: 336 (M+H)$^+$

Elemental Analysis Calcd. for $C_{20}H_{21}N_3O_2 \cdot CH_4O_3S$: C 58.45, H 5.84, N 9.74

Found: C 58.31, H 5.77, N 9.67

(6) [3-[Spiro[2H-1-benzopyran-2,1'-cyclopentane]-4-yl]benzoyl]guanidine methanesulfonate mp: 213–215° C.

IR (Nujol): 3250, 3050, 1705, 1590 cm$^{-1}$

NMR (DMSO-d$_6$, δ): 1.6–2.2 (8H, m), 2.38 (3H, s), 5.98 (1H, s), 6.8–7.0 (3H, m), 7.1–7.3 (1H, m), 7.6–8.0 (4H, m), 8.42 (4H, br s), 11.31 (1H, s)

(+) APCI MASS: 348 (M+H)$^+$

Elemental Analysis Calcd. for $C_{21}H_{21}N_3O_2 \cdot CH_4O_3S$: C 59.58, H 5.68, N 9.47 Found: C 59.63, H 5.71, N 9.41

(7) [3-(2,2-Dimethyl-2H-1-benzopyran-4-yl)benzoyl]guanidine methanesulfonate
mp: 225–226° C.
IR (Nujol): 3330, 3100, 1700, 1660, 1600 cm$^{-1}$
NMR (DMSO-d$_6$, δ): 1.46 (6H, s), 2.41 (3H, s), 5.91 (1H, s), 6.8–7.0 (3H, m), 7.1–7.3 (1H, m), 7.6–7.7 (2H, m), 7.8–8.1 (2H, m), 8.43 (4H, br s)
(+) APCI MASS: 322 (M+H)$^+$
Elemental Analysis Calcd. for $C_{19}H_{19}N_3O_2 \cdot CH_4O_3S$: C 57.54, H 5.55, N 10.06 Found: C 57.59, H 5.63, N 10.05

(8) [3-(2H-1-Benzopyran-4-yl)benzoyl]guanidine methanesulfonate
mp: 163–164° C.
IR (Nujol): 3320, 3120, 1700 cm$^{-1}$
NMR (DMSO-d$_6$, δ): 2.40 (3H, s), 4.86 (2H, d, J=3.9 Hz), 6.07 (1H, t, J=3.9 Hz), 6.8–9.0 (3H, m), 7.1–7.3 (1H, m), 7.6–7.7 (2H, m), 7.8–8.1 (2H, m), 8.50 (4H, br s), 11.32 (1H, s)
(+) APCI MASS: 294 (M+H)$^+$
Elemental Analysis Calcd. for $C_{17}H_{15}N_3O_2 \cdot CH_4O_3S$: C 55.52, H 4.92, N 10.79 Found: C 55.58, H 5.03, N 10.80

(9) [3-(3,5-Dimethylphenyl)benzoyl]guanidine methanesulfonate
mp: 214–215° C.
IR (Nujol): 3350, 1700, 1260, 1160, 1050 cm$^{-1}$
NMR (DMSO-d$_6$, δ): 2.37 (6H, s), 2.40 (3H, s), 7.08 (1H, s), 7.37 (2H, s), 7.69 (1H, dd, J=7.8, 7.8 Hz), 7.93 (1H, d, J=7.8 Hz), 8.00 (1H, d, J=7.8 Hz), 8.18 (1H, s), 8.–45 (4H, br s)
(+) APCI MASS: 268 (M+H)$^+$
Elemental Analysis Calcd. for $C_{16}H_{17}N_3O \cdot CH_3SO_3H$: C 56.18, H 5.82, N 11.56 Found: C 56.22, H 6.08, N 11.07

(10) [3-(3,5-Difluorophenyl)benzoyl]guanidine methanesulfonate
mp: 240–241° C.
IR (Nujol): 3350, 3150, 1700, 1600, 1270, 1160 cm$^{-1}$
NMR (DMSO-d$_6$, δ): 2.42 (3H, s), 7.27–7.39 (1H, m), 7.53–7.64 (2H, m), 7.73 (1H, dd, J=7.8, 7.8 Hz), 7.99 (1H, d, J=7.8 Hz), 8.11 (1H, d, J=7.8 Hz), 8.26 (1H, s), 8.49 (4H, br s), 11.45 (1H, s)
(+) APCI MASS: 276 (M+H)$^+$
Elemental Analysis Calcd. for $C_{14}H_{11}F_2N_3O \cdot CH_3SO_3H$: C 48.52, H 4.07, N 11.31 Found: C 48.69, H 4.13, N 11.16

(11) [3-[3,5-Bis(trifluoromethyl)phenyl]benzoyl]guanidine methanesulfonate
mp: 224–226° C.
IR (Nujol): 3350, 3200, 1700, 1610, 1280, 1200, 1120 cm$^{-1}$
NMR (DMSO-d$_6$, δ): 2.41 (3H, s), 7.78 (1H, dd, J=7.8, 7.8 Hz), 8.04 (1H, d, J=7.8 Hz), 8.18–8.26 (2H, m), 8.35 (1H, s), 8.45 (2H, s), 8.52 (4H, br s), 11.51 (1H, s)
(+) APCI MASS: 376 (M+H)$^+$
Elemental Analysis Calcd. for $C_{16}H_{11}F_6N_3O \cdot CH_3SO_3H$: C 43.32, H 3.21, N 8.91 Found: C 43.71, H 3.01, N 8.89

(12) [3-(2,3-Dichlorophenyl)benzoyl]guanidine methanesulfonate
mp: 208–210° C.
IR (Nujol): 3300, 3100, 1720, 1580, 1300, 1170 cm$^{-1}$
NMR (DMSO-d$_6$, δ): 2.43 (3H, s), 7.46–7.55 (2H, m), 7.69–7.79 (2H, m), 7.83 (1H, ddd, J=7.8, 1.5, 1.5 Hz), 8.00 (1H, dd, J=1.5, 1.5 Hz), 8.05 (1H, ddd, J=7.8, 1.5, 1.5 Hz), 8.44 (2H, br s), 8.59 (2H, br s), 11.39 (1H, s)
(+) APCI MASS: 308 (M+H)$^+$
Elemental Analysis Calcd. for $C_{14}H_{11}Cl_2N_3O \cdot CH_3SO_3H$: C 44.57, H 3.74, N 10.39 Found: C 44.67, H 3.67, N 10.30

(13) [3-(2,6-Dichlorophenyl)benzoyl]guanidine methanesulfonate
mp: 238–240° C.
IR (Nujol): 3300, 1710, 1580, 1170 cm$^{-1}$
NMR (DMSO-d$_6$, δ): 2.42 (3H, s), 7.46–7.55 (1H, m), 7.63–7.70 (3H, m), 7.77 (1H, dd, J=7.7, 7.7 Hz), 7.87 (1H, dd, J=1.5, 1.5 Hz), 8.08 (1H, dd, J=7.7, 1.5, 1.5 Hz), 8.39 (2H, br s), 8.61 (2H, br s), 11.33 (1H, s)
(+) APCI MASS: 308 (M+H)$^+$
Elemental Analysis Calcd. for $C_{14}H_{11}Cl_2N_3O \cdot CH_3SO_3H$: C 44.57, H 3.74, N 10.39 Found: C 44.42, H 3.70, N 10.29

(14) [3-(3,5-Dichlorophenyl)-5-hydroxymethylbenzoyl]guanidine methanesulfonate
mp: 209–211° C.
IR (Nujol): 3350, 3150, 1700, 1560, 1150 cm$^{-1}$
NMR (DMSO-d$_6$, δ): 2.40 (3H, s), 4.68 (2H, s), 7.69 (1H, dd, J=1.8, 1.8 Hz), 7.85 (2H, dd, J=1.8, 1.8 Hz), 7.98 (1H, s), 8.01 (1H, s), 8.12 (1H, s), 8.46 (4H, br s), 11.39 (1H, s)
(+) APCI MASS: 338 (M+H)$^+$

(15) [3-(3,5-Dichlorophenyl)benzoyl]guanidine methanesulfonate
mp: 219–221° C.
IR (Nujol): 3350, 3100, 1700, 1610, 1150 cm$^{-1}$
NMR (DMSO-d$_6$, δ): 2.45 (3H, s), 7.69 (1H, dd, J=1.9, 1.9 Hz), 7.72 (1H, dd, J=8.0, 8.0 Hz), 7.86 (2H, dd, J=1.9, 1.9 Hz), 8.00 (1H, d, J=8.0 Hz), 8.11 (1H, d, J=8.0 Hz), 8.25 (1H, s), 8.49 (4H, br s), 11.48 (1H, s)
(+) APCI MASS: 308 (M+H)$^+$
Elemental Analysis Calcd. for $C_{14}H_{11}Cl_2N_3O \cdot CH_3SO_3H$: C 44.57, H 3.74, N 10.39 Found: C 44.47, H 3.84, N 10.10

(16) [3-(3,5-Dimethoxyphenyl)benzoyl]guanidine methanesulfonate
mp: 180–182° C.
IR (Nujol): 3350, 1700, 1590, 1160 cm$^{-1}$
NMR (DMSO-d$_6$, δ): 2.42 (3H, s), 3.83 (6H, s), 6.58 (1H, dd, J=2.1, 2.1 Hz), 6.88 (2H, dd, J=2.1, 2.1 Hz), 7.69 (1H, dd, J=7.7, 7.7 Hz), 7.95 (1H, d, J=7.7 Hz), 8.10 (1H, d, J=7.7 Hz), 8.19 (1H, s), 8.42 (2H, br s), 8.57 (2H, br s), 11.42 (1H, s)
(+) APCI MASS: 300 (M+H)$^+$
Elemental Analysis Calcd. for $C_{16}H_{17}N_3O_3 \cdot CH_3SO_3H$: C 51.64, H 5.35, N 10.63 Found: C 52.03, H 5.57, N 10.56

(17) [3-(3,5-Dihydroxyphenyl)benzoyl]guanidine methanesulfonate
mp: 244° C. (dec.)
IR (Nujol): 3300, 1700, 1590, 1160 cm$^{-1}$
NMR (DMSO-d$_6$, δ): 2.38 (3H, s), 6.31 (1H, dd, J=2.1, 2.1 Hz), 6.57 (2H, dd, J=2.1, 2.1 Hz), 7.67 (1H, dd, J=7.7, 7.7 Hz), 7.88–7.93 (2H, m), 8.09 (1H, s), 8.36 (2H, br s), 8.48 (2H, br s), 9.50 (2H, br s), 11.31 (1H, s)
(+) APCI MASS: 272 (M+H)$^+$

(18) [3-(Benzofuran-7-yl)benzoyl]guanidine methanesulfonate
mp: 196–197° C.
IR (Nujol): 3325, 3125, 1710, 1265, 1155 cm$^{-1}$
NMR (DMSO-d$_6$, δ): 2.41 (3H, s), 7.10 (1H, d, J=2.2 Hz), 7.42 (1H, dd, J=7.6, 7.6 Hz), 7.63–7.83 (3H, m), 8.02 (1H, d, J=8.1 Hz), 8.12 (1H, d, J=2.2 Hz), 8.23 (1H, d, J=7.9 Hz), 8.3–8.7 (5H, m), 11.42 (1H, s)
(+) APCI MASS: 279 (M+H)$^+$

(19) [3-(8-Quinolyl)benzoyl]guanidine dimethanesulfonate
mp: 234–236° C.
IR (Nujol): 3300, 1700, 1210, 1160 cm$^{-1}$
NMR (DMSO-d$_6$, δ): 2.44 (6H, s), 7.73–7.89 (3H, m), 7.97–8.11 (3H, m), 8.20–8.24 (2H, m), 8.48 (2H, br s), 8.64 (2H br s), 8.79 (1H, dd, J=8.3, 1.6 Hz), 9.02 (1H, dd, J=4.6, 1.7 Hz), 10.22 (1H, br s), 11.44 (1H, s)

(+) APCI MASS: 291 (M+H)⁺

Elemental Analysis Calcd. for $C_{17}H_{14}N_4O \cdot 2CH_3SO_3H$: C 47.10, H 4.99, N 11.56 Found: C 47.24, H 4.59, N 11.24

(20) [3-(5-Isoquinolyl)benzoyl]guanidine dimethanesulfonate mp: 200–202° C.

IR (Nujol): 3300, 1700, 1590, 1160 cm⁻¹

NMR (DMSO-d₆, δ): 2.41 (6H, s), 7.81–7.95 (2H, m), 8.08–8.27 (5H, m), 8.50 (4H, br s), 8.62 (1H, d, J=8.1 Hz), 8.68 (1H, d, J=6.7 Hz), 9.98 (1H, s), 11.52 (2H, br s)

(+) APCI MASS: 291 (M+H)⁺

(21) 3-(5-Quinoxalinyl)benzoyl]guanidine methanesulfonate mp: 219° C. (dec.)

IR (Nujol): 3350, 3150, 1710, 1590, 1260 cm⁻¹

NMR (DMSO-d₆, δ): 2.37 (3H, s), 7.76 (1H, dd, J=7.7, 7.7 Hz), 7.99–8.07 (4H, m), 8.16–8.23 (2H, m), 8.44 (4H, br s), 8.98 (1H, d, J=1.8 Hz), 9.03 (1H, d, J=1.8 Hz), 11.33 (1H, s)

(+) APCI MASS: 292 (M+H)⁺

Elemental Analysis Calcd. for $C_{16}H_{13}N_5O \cdot CH_3SO_3H$: C 52.70, H 4.42, N 18.08 Found: C 52.60, H 4.42, N 17.58

(22) [3-(2-Methylimidazo[1,2-a]pyridin-8-yl)benzoyl]guanidine methanesulfonate mp: 200–202° C.

IR (Nujol): 3350, 3100, 1710, 1600, 1170 cm⁻¹

NMR (DMSO-d₆, δ): 2.36 (3H, s), 2.41 (3H, s), 7.17 (1H, dd, J=7.0, 6.9 Hz), 7.67 (1H, d, J=7.0 Hz), 7.78 (1H, dd, J=7.9, 7.9 Hz), 7.94 (1H, s), 8.03 (1H, d, J=7.9 Hz), 8.36 (1H, d, J=7.9 Hz), 8.43 (4H, br s), 8.52 (1H, s), 8.66 (1H, d, J=6.9 Hz)

(+) APCI MASS: 294 (M+H)⁺

(23) [3-(2-Cyano-1-cyclopenten-1-yl)benzoyl]guanidine methanesulfonate mp: 231–233° C.

IR (Nujol): 3300, 2200, 1710, 1260, 1050 cm⁻¹

NMR (DMSO-d₆, δ): 2.06 (2H, tt, J=7.5, 7.5 Hz), 2.39 (3H, s), 2.83 (2H, t, J=7.5 Hz), 3.02 (2H, t, J=7.5 Hz), 7.75 (1H, dd, J=7.8, 7.8 Hz), 7.99–8.06 (2H, m), 8.21 (1H, s), 8.39 (1H, br s), 8.51 (2H, br s), 11.42 (1H, s)

(+) APCI MASS: 255 (M+H)⁺

Elemental Analysis Calcd. for $C_{14}H_{14}N_4O \cdot CH_3SO_3H$: C 51.42, H 5.18, N 15.99 Found: C 51.47, H 5.05, N 15.77

(24) [3-(4-Cyano-2,5-dihydrothiophen-3-yl)benzoyl]guanidine methanesulfonate mp: 209° C. (dec.)

IR (Nujol): 3350, 3100, 2200, 1700, 1600 cm⁻¹

NMR (DMSO-d₆, δ): 2.42 (3H, s), 4.16 (2H, t-like, J=4.4 Hz), 4.42 (2H, t-like, J=4.4 Hz), 7.76 (1H, dd, J=7.8, 7.8 Hz), 7.98–8.07 (2H, m), 8.20 (1H, s), 8.42 (2H, br s), 8.52 (2H, br s), 11.43 (1H, s)

(+) APCI MASS: 273 (M+H)⁺

(25) [3-(4-Cyano-2,5-dihydrofuran-3-yl)benzoyl]guanidine methanesulfonate mp: 280° C. (dec.)

IR (Nujol): 3300, 2200, 1710, 1600 cm⁻¹

NMR (DMSO-d₆, δ): 2.37 (3H, s), 4.95 (2H, t-like, J=4.9 Hz), 5.24 (2H, t-like, J=4.9 Hz), 7.80 (1H, dd, J=7.8, 7.8 Hz), 8.01–8.09 (2H, m), 8.22 (1H, s), 8.41 (4H, br s), 11.43 (1H, s)

(+) APCI MASS: 257 (M+H)⁺

(26) [3-(2-Chlorothiophen-3-yl)benzoyl]guanidine methanesulfonate mp: 187–189° C.

IR (Nujol): 3350, 1710, 1600 cm⁻¹

NMR (DMSO-d₆, δ): 2.46 (3H, s), 7.37 (1H, d, J=5.8 Hz), 7.65 (1H, d, J=5.8 Hz), 7.73 (1H, dd, J=7.8, 7.8 Hz), 7.93–8.01 (2H, m), 8.14 (1H, dd, J=1.6, 1.6 Hz), 8.44 (2H, br s), 8.63 (2H, br s), 11.43 (1H, s)

(+) APCI MASS: 280 (M+H)⁺

Elemental Analysis Calcd. for $C_{12}H_{10}ClN_3OS \cdot CH_3SO_3H$: C 41.54, H 3.75, N 11.18 Found: C 41.24, H 3.45, N 11.00

(27) [3-(Benzoxazol-4-yl)benzoyl]guanidine methanesulfonate mp: 145–148° C. (dec.)

IR (Nujol): 1705, 1150, 1040, 720 cm⁻¹

NMR (DMSO-d₆, δ): 2.41 (3H, s), 7.56–8.05 (4H, m), 8.3–8.6 (7H, m), 8.88 (1H, s), 11.42 (1H, s)

(+) APCI MASS: 281 (M+H)⁺

EXAMPLE 5

The following compound was obtained by reacting methyl 3-(3,5-dichlorophenyl)-5-methoxycarbonylbenzoate with guanidine hydrochloride according to similar manners to those of Examples 1, 2 and 3.

[3-(3,5-Dichlorophenyl)-5-diaminomethyleneaminocarbonylbenzoyl]guanidine dimethanesulfonate mp: 245–247° C.

IR (Nujol): 3300, 1720, 1580, 1320, 1200 cm⁻¹

NMR (DMSO-d₆, δ): 2.44 (6H, s), 7.77 (1H, dd, J=1.8, 1.8 Hz), 7.99 (2H, dd, J=1.8, 1.8 Hz), 8.45 (1H, s), 8.52 (8H, br s), 8.54 (2H, dd, J=1.5, 1.5 Hz), 11.67 (2H, s)

(+) APCI MASS: 393 (M+H)⁺

EXAMPLE 6

The following compounds were obtained according to similar manners to those of Examples 1, 2 and 3.

(1) [3-(2-Chlorofuran-3-yl)benzoyl]guanidine methanesulfonate mp: 182–184° C.

IR (Nujol): 3300, 1700, 1590, 1250 cm⁻¹

NMR (DMSO-d₆, δ): 2.39 (3H, s), 7.15 (1H, d, J=2.2 Hz), 7.72 (1H, dd, J=7.8, 7.8 Hz), 7.88 (1H, d, J=2.2 Hz), 7.93 (1H, d, J=7.8 Hz), 8.01 (1H, d, J=7.8 Hz), 8.19 (1H, s), 8.48 (4H, br s), 11.39 (1H, s)

(+) APCI MASS (m/z): 264 (M of free compound+H)⁺

Elemental Analysis Calcd. for $C_{12}H_{10}ClN_3O_2 \cdot CH_3SO_3H$: C 43.40, H 3.92, N 11.68 Found: C 43.12, H 3.94, N 11.44

(2) [3-(2-Difluoromethylfuran-3-yl)benzoyl]guanidine methanesulfonate mp: 183° C. (dec.)

IR (Nujol): 3300, 3100, 1700, 1590, 1250, 1200 cm⁻¹

NMR (DMSO-d₆, δ): 2.37 (3H, s), 7.02 (1H, s), 7.22 (1H, t, J=51.7 Hz), 7.72 (1H, dd, J=7.6, 7.6 Hz), 7.82 (1H, d, J=7.6 Hz), 7.94–8.03 (3H, m), 8.40 (4H, br s), 11.39 (1H, s)

(+) APCI MASS (m/z): 280 (M of free compound+H)⁺

Elemental Analysis Calcd. for $C_{13}H_{11}F_2N_3O_2 \cdot CH_3SO_3H$: C 44.80, H 4.03, N 11.19 Found: C 44.96, H 3.74, N 11.08

(3) [3-(2-Acetylthiophen-3-yl)benzoyl]guanidine methanesulfonate mp: 165–166° C.

IR (Nujol): 3250, 1700, 1640, 1160 cm⁻¹

NMR (DMSO-d₆, δ): 2.21 (3H, s), 2.40 (3H, s), 7.29 (1H, d, J=5.0 Hz), 7.69 (1H, dd, J=7.9, 7.9 Hz), 7.82 (1H, d, J=7.9 Hz), 8.00–8.04 (3H, m), 8.40 (2H, br s), 8.57 (2H, br s), 11.35 (1H, s)

(+) APCI MASS (m/z): 288 (M of free compound+H)⁺

(4) [3-(2-Sulfamoylthiophen-3-yl)benzoyl]guanidine methanesulfonate mp: 209–210° C.

IR (Nujol): 3300, 1710, 1580, 1340 cm$^{-1}$

NMR (DMSO-d$_6$, δ): 2.38 (3H, s), 7.28 (1H, d, J=5.1 Hz), 7.68 (1H, dd, J=7.7, 7.7 Hz), 7.80 (2H, s), 7.88–7.98 (3H, m), 8.09 (1H, s), 8.38 (4H, br s), 11.31 (1H, s)

(+) APCI MASS (m/z): 325 (M of free compound+H)$^+$

Elemental Analysis Calcd. for C$_{12}$H$_{12}$N$_4$O$_3$S$_2$·CH$_3$SO$_3$H: C 37.13, H 3.84, N 13.32 Found: C 37.34, H 3.67, N 13.18

(5) [3-(5-Sulfamoylthiophen-3-yl)benzoyl]guanidine methanesulfonate mp: 240–246° C.

IR (Nujol): 3300, 1690, 1320, 1280 cm$^{-1}$

NMR (DMSO-d$_6$, δ): 2.41 (3H, s), 7.69 (1H, dd, J=7.8, 7.8 Hz), 7.75 (2H, s), 7.91 (1H, d, J=7.8 Hz), 8.07 (1H, d, J=1.6 Hz), 8.09 (1H, d, J=7.8 Hz), 8.25 (1H, s), 8.31 (1H, d, J=1.6 Hz), 8.44 (4H, br s), 11.39 (1H, s)

(+) APCI MASS (m/z): 325 (M of free compound+H)$^+$

Elemental Analysis Calcd. for C$_{12}$H$_{12}$N$_4$O$_3$S$_2$·CH$_3$SO$_3$H: C 37.13, H 3.84, N 13.32 Found: C 37.53, N 3.90, N 13.13

(6) [3-(2-Difluoromethylthiophen-3-yl)benzoyl]guanidine methanesulfonate mp: 184–187° C.

IR (Nujol): 3300, 1710, 1280, 1170 cm$^{-1}$

NMR (DMSO-d$_6$, δ): 2.41 (3H, s), 7.26 (1H, t, J=54.1 Hz), 7.40 (1H, d, J=5.1 Hz), 7.73 (1H, dd, J=7.7, 7.7 Hz), 7.81 (1H, d, J=7.7 Hz), 7.95–8.02 (3H, m), 8.42 (2H, br s), 8.54 (2H, br s), 11.41 (1H, s)

(+) APCI MASS (m/z): 296 (M of free compound+H)$^+$ (7) [3-(2,5-Dichlorothiophen-3-yl)benzoyl]guanidine methanesulfonate mp: 182–184° C.

IR (Nujol): 3300, 1700, 1590, 1270 cm$^{-1}$

NMR (DMSO-d$_6$, δ): 2.40 (3H, s), 7.49 (1H, s), 7.74 (1H, dd, J=7.8, 7.8 Hz), 7.92–8.01 (2H, m), 8.11 (1H, dd, J=1.6, 1.6 Hz), 8.45 (4H, br s), 11.36 (1H, s)

(+) APCI MASS (m/z): 314 (M of free compound+H)$^+$

Elemental Analysis Calcd. for C$_{12}$H$_9$Cl$_2$N$_3$OS·CH$_3$SO$_3$H: C 38.06, H 3.19, N 10.24 Found: C 38.06, H 3.15, N 10.06

(8) [3-(5-Chlorothiophen-3-yl)benzoyl]guanidine methanesulfonate mp: 216–219° C.

IR (Nujol): 3350, 3150, 1700, 1580, 1270 cm$^{-1}$

NMR (DMSO-d$_6$, δ): 2.43 (3H, s), 7.66 (1H, dd, J=7.8, 7.8 Hz), 7.74 (1H, d, J=1.7 Hz), 7.89 (1H, d, J=7.8 Hz), 7.96 (1H, d, J=1.7 Hz), 8.05 (1H, d, J=7.8 Hz), 8.23 (1H, s), 8.45 (4H, br s), 11.41 (1H, s)

(+) APCI MASS (m/z): 280 (M of free compound+H)$^+$

Elemental Analysis Calcd. for C$_{12}$H$_{10}$ClN$_3$OS·CH$_3$SO$_3$H: C 41.54, H 3.75, N 11.18 Found: C 41.95, H 3.69, N 10.95

(9) [3-(2-Chlorothiophen-3-yl)-5-hydroxymethylbenzoyl]guanidine hydrochloride mp: 195–197° C.

IR (Nujol): 3350, 3100, 1690, 1620, 1570, 1250 cm$^{-1}$

NMR (DMSO-d$_6$, δ): 4.66 (2H, s), 7.47 (1H, d, J=5.8 Hz), 7.62 (1H, d, J=5.8 Hz), 7.92 (1H, s), 8.04 (1H, s), 8.19 (1H, s), 8.61 (2H, br s), 8.71 (2H, br s), 12.07 (1H, s)

(+) APCI MASS (m/z): 310 (M of free compound+H)$^+$

Elemental Analysis Calcd. for C$_{13}$H$_{12}$ClN$_3$O$_2$S·HCl: C 45.10, H 3.78, N 12.14 Found: C 45.00, H 3.67, N 11.90

(10) [3-(3-Chlorothiophen-2-yl)benzoyl]guanidine methanesulfonate mp: 191–193° C.

IR (Nujol): 3300, 1710, 1040, 720 cm$^{-1}$

NMR (DMSO-d$_6$, δ): 2.40 (3H, s), 7.25 (1H, d, J=5.4 Hz), 7.74 (1H, dd, J=7.8, 7.8 Hz), 7.82 (1H, d, J=5.4 Hz), 7.96–8.02 (2H, m), 8.38 (1H, s), 8.2–8.7 (4H, m), 11.40 (1H, s)

(+) APCI MASS: 280 (M of free compound+H)$^+$

Elemental Analysis Calcd. for C$_{12}$H$_{10}$ClN$_3$OS·CH$_4$OS: C 41.54, H 3.75, N 11.18 Found: C 41.58, H 3.47, N 11.05

(11) [3-(5-Chlorothiophen-2-yl)benzoyl]guanidine methanesulfonate mp: 256–258° C.

IR (Nujol): 3350, 1700, 1170, 1045 cm$^{-1}$

NMR (DMSO-d$_6$, δ): 2.40 (3H, s), 7.25 (1H, d, J=3.9 Hz), 7.56 (1H, d, J=3.9 Hz), 7.67 (1H, dd, J=7.8 Hz), 7.88,(1H, d, J=7.8 Hz), 7.96 (1H, d, J=7.8 Hz), 8.11 (1H, s), 8.2–8.6 (4H, m), 11.42 (1H, s)

(+) APCI MASS: 280 (M of free compound+H)$^+$

Elemental Analysis Calcd. for C$_{12}$H$_{10}$ClN$_3$OS·CH$_4$O$_3$S: C 41.54, H 3.75, N 11.18 Found: C 41.48, H 3.68, N 11.29

(12) [3-(5-Methylthiophen-2-yl)benzoyl]guanidine isethionate mp: 154–156° C.

IR (Nujol): 3300, 3150, 1700, 1590, 1180, 1035 cm$^{-1}$

NMR (DMSO-d$_6$, δ): 2.50 (3H, s), 2.68 (2H, t, J=6.9 Hz), 3.65 (2H, t, J=6.9 Hz), 6.86–6.92 (1H, m), 7.46 (1H, d, J=3.6 Hz), 7.63 (1H, dd, J=8.0, 8.0 Hz), 7.82 (1H, d, J=8.0 Hz), 7.93 (1H, d, J=8.0 Hz), 7.08 (1H, s), 8.39 (4H, s), 11.34 (1H, s)

(+) APCI MASS: 260 (M of free compound+H)$^+$

Elemental Analysis Calcd. for C$_{13}$H$_{13}$N$_3$OS·C$_2$H$_6$O$_4$S: C 46.74, H 4.97, N 10.90 Found: C 47.08, H 4.90, N 10.97

(13) [3-(3-Methylthiophen-2-yl)benzoyl]guanidine methanesulfonate mp: 169–170° C.

IR (Nujol): 3300, 3150, 1713, 1175, 1040 cm$^{-1}$

NMR (DMSO-d$_6$, δ): 2.31 (3H, s), 2.39 (3H, s), 7.06 (1H, d, J=5.1 Hz), 7.57 (1H, d, J=5.1 Hz), 7.70 (1H, dd, J=7.7, 7.7 Hz), 7.83 (1H, d, J=7.7 Hz), 7.94 (1H, d, J=7.7 Hz), 7.99 (1H, s), 8.37 (2H, s), 8.51 (2H, s), 11.34 (1H, s)

(+) APCI MASS: 260 (M of free compound+H)$^+$

Elemental Analysis Calcd. for C$_{13}$H$_{13}$N$_3$OS·CH$_4$O$_3$S: C 47.31, H 4.82, N 11.82 Found: C 47.21, H 4.68, N 11.72

(14) [3-(2-Methylthiophen-3-yl)benzoyl]guanidine methanesulfonate mp: 163–164° C.

IR (Nujol): 3330, 3130, 1697, 1165, 1048 cm$^{-1}$

NMR (DMSO-d$_6$, δ): 2.39 (3H, a), 2.50 (3H, s), 7.21 (1H, d, J=5.3 Hz), 7.43 (1H, d, J=5.3 Hz), 7.68 (1H, dd, J=7.6, 7.6 Hz), 7.80 (1H, d, J=7.6 Hz), 7.91 (1H, d, J=7.6 Hz), 7.97 (1H, s), 8.25–8.70 (4H, br), 11.31 (1H, s)

(+) APCI MASS: 260 (M of free compound+H)$^+$

Elemental Analysis Calcd. for C$_{13}$H$_{13}$N$_3$OS·CH$_4$O$_3$S: C 47.31, H 4.82, N 11.82 Found: C 47.12, H 4.79, N 11.73

(15) [3-(4-Methylthiophen-3-yl)benzoyl]guanidine methanesulfonate mp: 167–168° C.

IR (Nujol): 3350, 3080, 1705, 1600, 1210, 1045 cm$^{-1}$

NMR (DMSO-d$_6$, δ): 2.25 (3H, s), 2.43 (3H, s), 7.33–7.37 (1H, m), 7.62–7.73 (2H, m), 7.80 (1H, d, J=7.6 Hz), 7.95 (1H, d, J=7.6 Hz), 7.99 (1H, s), 8.42 (2H, s), 8.59 (2H, s), 11.36 (1H, s)

(+) APCI MASS: 260 (M of free compound+H)$^+$

Elemental Analysis Calcd. for C$_{13}$H$_{13}$N$_3$OS·CH$_4$O$_3$S: C 47.31, H 4.82, N 11.82 Found: C 47.06, H 4.56, N 11.70

EXAMPLE 7

The following compound was obtained by reacting methyl 3-(2-chlorothiophen-3-yl)-5-methoxycarbonylbenzoate with guanidine hydrochloride according to similar manners to those of Examples 1, 2 and 3.

[3-(2-Chlorothiophen-3-yl)-5-diaminomethyleneaminocarbonylbenzoyl]guanidine dimethanesulfonate mp: 259–260° C.

IR (Nujol): 3350, 3100, 1720, 1610, 1310, 1200 cm$^{-1}$

NMR (DMSO-d$_6$, δ): 2.42 (6H, s), 7.47 (1H, d, J=5.8 Hz), 7.71 (1H, d, J=5.8 Hz), 8.42 (2H, s), 8.47 (1H, s), 8.59 (8H, br s), 11.59 (2H, s)

(+) APCI MASS (m/z): 365 (M of free compound+H)$^+$

Elemental Analysis Calcd. for C$_{14}$H$_{13}$ClN$_6$O$_2$S.2CH$_3$SO$_3$H: C 34.50, H 3.80, N 15.09 Found: C 34.68, H 3.66, N 14.89

EXAMPLE 8

The following compounds were obtained according to similar manners to those of Examples 1,2 and 3.

(1) [3-(Benzo[b]thiophen-4-yl)benzoyl]guanidine methanesulfonate mp: 184–186° C.

IR (Nujol): 3350, 3150, 1710, 1600, 1250 cm$^{-1}$

NMR (DMSO-d$_6$, δ): 2.41 (3H, s), 7.44–7.56 (3H, m), 7.77 (1H, dd, J=7.7, 7.7 Hz), 7.87 (1H, d, J=5.5 Hz), 7.95 (1H, d, J=7.7 Hz), 8.04 (1H, d, J=7.7 Hz), 8.08–8.13 (2H, m), 8.41 (2H, br s), 8.55 (2H, br s), 11.35 (1H, s)

(+) APCI MASS: 296 (M+H)$^+$ (2) [3-(Benzo[b]thiophen-3-yl)benzoyl]guanidine methanesulfonate mp: 221–223° C.

IR (Nujol): 3350, 1700, 1570, 1250 cm$^{-1}$

NMR (DMSO-d$_6$, δ): 2.40 (3H, s), 7.46–7.53 (2H, m), 7.78 (1H, dd, J=7.7, 7.7 Hz), 7.90–8.04 (4H, m), 8.08–8.18 (2H, m), 8.41 (2H, br s), 8.54 (2H, br s), 11.38 (1H, s)

(+) APCI MASS: 296 (M+H)$^+$

Elemental Analysis Calcd. for C$_{16}$H$_{13}$N$_3$OS.CH$_3$SO$_3$H: C 52.16, H 4.38, N 10.73 Found: C 51.91, H 4.37, N 10.48

(3) [3-(2-Chlorobenzo[b]thiophen-3-yl)benzoyl]guanidine methanesulfonate mp: 228–230° C.

IR (Nujol): 3330, 3100, 1710, 1250, 1180, 1150 cm$^{-1}$

NMR (DMSO-d$_6$, δ): 2.37 (3H, s), 7.41–7.57 (3H, s), 7.83 (1H, dd, J=7.5, 7.5 Hz), 7.90 (1H, d, J=7.5 Hz), 8.06–8.12 (3H, m), 8.35 (2H, br s), 8.53 (2H, br s), 11.32 (1H, s)

(+) APCI MASS: 330 (M+H)$^+$ (4) [3-(Benzofuran-4-yl)-5-hydroxymethylbenzoyl]guanidine methanesulfonate mp: 217–220° C.

IR (Nujol): 3300, 3100, 1700, 1570, 1310 cm$^{-1}$

NMR (DMSO-d$_6$, δ): 2.40 (3H, s), 4.72 (2H, s), 7.16 (1H, d, J=2.1 Hz), 7.42–7.52 (2H, m), 7.65–7.72 (1H, m), 7.93 (1H, s), 7.97 (1H, s), 8.07 (1H, s), 8.14 (1H, d, J=2.1 Hz), 8.53 (4H, br s), 11.37 (1H, s)

(+) APCI MASS: 310 (M+H)$^+$

Elemental Analysis Calcd. for C$_{17}$H$_{15}$N$_3$O$_3$.CH$_3$SO$_3$H: C 53.33, H 4.72, N 10.36 Found: C 53.73, H 4.80, N 10.07

(5) [3-(2-Difluoromethylbenzofuran-4-yl)benzoyl]guanidine methanesulfonate mp: 216–218° C.

IR (Nujol): 3350, 3150, 1710, 1150 cm$^{-1}$

NMR (DMSO-d$_6$, δ): 2.38 (3H, s), 7.34 (1H, t, J=52.8 Hz), 7.48–7.56 (2H, m), 7.76–7.88 (3H, m), 8.04 (1H, d, J=7.8 Hz), 8.22 (1H, d, J=7.8 Hz), 8.39 (1H, s), 8.45 (4H, br s.), 11.40 (1H, s)

(+) APCI MASS: 330 (M+H)$^+$

Elemental Analysis Calcd. for C$_{17}$H$_{13}$F$_2$N$_3$O$_2$.CH$_3$SO$_3$H: C 50.82, H 4.03, N 9.88 Found: C 50.91, H 3.73, N 9.68

(6) [3-(2-Chlorobenzofuran-3-yl)benzoyl]guanidine methanesulfonate

212–214° C.

IR (Nujol): 3350, 3150, 1710, 1260, 1180, 1160 cm$^{-1}$

NMR (DMSO-d$_6$, δ): 2.36 (3H, s), 7.37–7.52 (2H, m), 7.71–7.87 (3H, m), 8.04 (2H, ddd, J=7.8, 1.7, 1.7 Hz), 8.21 (1H, s), 8.38 (2H, br s), 8.48 (2H, br s), 11.38 (1H, s)

(+) APCI MASS: 314, 316 (M+H)$^+$ (7) [3-(2-Difluoromethylbenzofuran-3-yl)benzoyl]guanidine methanesulfonate mp: 207–208° C.

IR (Nujol): 3350, 3100, 1710, 1150 cm$^{-1}$

NMR (DMSO-d$_6$, δ): 2.35 (3H, s), 7.33 (1H, t, J=51.4 Hz), 7.45 (1H, dd, J=7.9, 7.9 Hz), 7.60 (1H, dd, J=7.9, 7.9 Hz), 7.75–7.95 (4H, m), 8.06–8.10 (2H, m), 8.40 (4H, br s), 11.38 (1H, s)

(+) APCI MASS: 330 (M+H)$^+$ (8) [3-(2-Methylbenzofuran-3-yl)benzoyl]guanidine methanesulfonate mp: 213–215° C.

IR (Nujol): 3300, 3150, 1700, 1590, 1170 cm$^{-1}$

NMR (DMSO-d$_6$, δ): 2.36 (3H, s), 2.57 (3H, s), 7.26–7.38 (2H, m), 7.59–7.65 (2H, m), 7.78 (1H, dd, J=7.7, 7.7 Hz), 7.91 (1H, d, J=7.7 Hz), 7.98 (1H, d, J=7.7 Hz), 8.09 (1H, s), 8.37 (2H, br s), 8.47 (2H, br s), 11.32 (1H, s)

(+) APCI MASS: 294 (M+H)$^+$

Elemental Analysis Calcd. for C$_{17}$H$_{15}$N$_3$O$_2$.CH$_3$SO$_3$H: C 55.52, H 4.92, N 10.79 Found: C 55.17, H 5.01, N 10.55

(9) [3-(Indol-4-yl)benzoyl]guanidine methanesulfonate mp: 235° C. (dec.)

IR (Nujol): 3250 (br), 1700, 1580, 1200 cm$^{-1}$

NMR (DMSO-d$_6$, δ): 2.38 (3H, s), 6.59 (1H, s), 7.18 (1H, d, J=7.0 Hz), 7.24 (1H, dd, J=7.0, 7.0 Hz), 7.45–7.50 (2H, m), 7.74 (1H, dd, J=7.7, 7.7 Hz), 7.96 (1H, d, J=7.7 Hz), 8.02 (1H, d, J=7.7 Hz), 8.23 (1H, s), 8.44 (4H, br s), 11.31 (1H, s), 11.37 (1H, s)

(+) APCI MASS: 279 (M+H)$^+$

Elemental Analysis Calcd. for C$_{16}$H$_{14}$N$_4$O.CH$_3$SO$_3$H: C 54.54, H 4.85, N 14.96 Found: C 54.14, H 4.79, N 14.78

(10) [3-(1-Methylindol-4-yl)benzoyl]guanidine methanesulfonate mp: 214° C. (dec.)

IR (Nujol): 3300, 1710, 1250, 1170 cm$^{-1}$

NMR (DMSO-d$_6$, δ): 2.39 (3H, s), 3.86 (3H, s), 6.57 (1H, d, J=3.2 Hz), 7.23 (1H, d, J=7.3 Hz), 7.31 (1H, dd, J=7.3, 7.3 Hz), 7.45 (1H, d, J=3.2 Hz), 7.53 (1H, d, J=7.3 Hz), 7.74 (1H, dd, J=7.7, 7.7 Hz), 7.97 (1H, d, J=7.7 Hz), 8.02 (1H, d, J=7.7 Hz), 8.22 (1H, s), 8.44 (4H, br s), 11.33 (1H, s)

(+) APCI MASS: 293 (M+H)$^+$

Elemental Analysis Calcd. for C$_{17}$H$_{16}$N$_4$O.CH$_3$SO$_3$H: C 55.66, H 5.19, N 14.42 Found: C 55.83, H 5.16, N 14.15

(11) [3-(1-Oxoindan-4-yl)benzoyl]guanidine methanesulfonate mp: 241–243° C.

IR (Nujol): 3300, 1710, 1260 cm$^{-1}$

NMR (DMSO-d$_6$, δ): 2.34 (3H, s), 2.68 (2H, t, J=5.8 Hz), 3.17 (2H, t, J=5.8 Hz), 7.60 (1H, dd, J=7.4, 7.4 Hz), 7.72–7.80 (3H, m), 7.94–8.03 (2H, m), 8.08 (1H, s), 8.39 (4H, br s), 11.31 (1H, m)

(+) APCI MASS: 294 (M+H)$^+$

(12) [3-(3-Chlorothiophen-4-yl)benzoyl]guanidine methanesulfonate mp: 197–198° C.

IR (Nujol): 3350, 1700, 1590, 1260 cm$^{-1}$

NMR (DMSO-d$_6$, δ): 2.43 (3H, s), 7.72 (1H, dd, J=7.7, 7.7 Hz), 7.83 (1H, d, J=3.5 Hz), 7.88 (1H, d, J=7.7 Hz), 7.94 (1H, d, J=3.5 Hz), 7.99 (1H, d, J=7.7 Hz), 8.08 (1H, s), 8.41 (2H, br s), 8.58 (2H, br s), 11.40 (1H, s)

(+) APCI MASS: 280 (M+H)$^+$

Elemental Analysis Calcd. for C$_{12}$H$_{10}$ClN$_3$OS.CH$_3$SO$_3$H: C 41.54, H 3.75, N 11.18 Found: C 41.65, H 3.55, N 11.06

(13) [5-(2,5-Dichlorothiophen-3-yl)-3-[(2-dimethylaminoethyl)carbamoyl]benzoyl]guanidine dihydrochloride
mp:245–247° C.
IR (Nujol): 3200, 1700, 1660, 1250 cm$^{-1}$
NMR (DMSO-d$_6$, δ): 2.84 (6H, s), 3.38–3.49 (2H, m), 3.64–3.74 (2H, m), 7.76 (1H, s), 8.45 (1H, s), 8.50 (1H, s), 8.62 (1H, s), 8.69 (4H, br s), 9.14 (1H, t, J=5.5 Hz), 10.14 (1H, br s), 12.33 (1H, s)
(+) APCI MASS: 428 (M+H)$^+$
(14) [5-(2,5-Dichlorothiophen-3-yl)-3-[(2-morpholinoethyl)carbamoyl]benzoyl]guanidine dihydrochloride
mp: 173° C. (dec.)
IR (Nujol): 3300 (br), 1700, 1250 cm$^{-1}$
NMR (DMSO-d$_6$, δ): 3.10–3.24 (2H, m), 3.40–3.57 (4H, m), 3.74–4.01 (6H, m), 7.77 (1H, s), 8.48 (1H, s), 8.51 (1H, s), 8.62 (1H, s), 8.73 (4H, s), 9.23 (1H, t, J=5.5 Hz), 11.05 (1H, br s), 12.38 (1H, s)
(+) APCI MASS: 470 (M+H)$^+$, 472 (M+H)$^+$
(15) [3-[2,3-(Methylenedioxy)phenyl]benzoyl]guanidine methanesulfonate
mp: 163–165° C.
IR (Nujol): 3325, 3120, 1710, 1155, 1045 cm$^{-1}$
NMR (DMSO-d$_6$, δ): 2.42 (3H, s), 6.12 (2H, s), 6.97–7.03 (2H, m), 7.18–7.28 (1H, m), 7.71 (1H, dd, J=7.8, 7.8 Hz), 7.95 (1H, d, J=7.8 Hz), 8.08 (1H, d, J=7.8 Hz), 8.10 (1H, s), 8.42 (2H, s), 8.56 (2H, s), 11.41 (1H, s)
Elemental Analysis Calcd. for C$_{15}$H$_{13}$N$_3$O$_3$.CH$_4$O$_3$S: C 50.65, H 4.52, N 11.08 Found: C 50.41, H 4.66, N 11.13
(16) [3-(2,5-Dichlorothiophen-3-yl)-5-hydroxtmethylbenzoyl]guanidine methanesulfonate
mp: 201–202° C.
IR (Nujol): 3310, 3120, 1707, 1690, 1197, 1045 cm$^{-1}$
NMR (DMSO-d$_6$, δ): 2.39 (3H, s), 4.66 (2H, s), 7.48 (1H, s), 7.86 (1H, s), 7.96 (1H, s), 7.99 (1H, s), 8.44 (4H, s), 11.34 (1H, s)
Elemental Analysis Calcd. for C$_{13}$H$_{11}$N$_3$O$_2$SCl$_2$.CH$_4$O$_3$S: C 38.19, H 3.43, N 9.54 Found: C 38.29, H 3.27, N 9.57
(17) [3-(2-Methylbenzofuran-7-yl)benzoyl]guanidine methanesulfonate
mp: 187–189° C.
IR (Nujol): 3350, 1710, 1155, 730 cm$^{-1}$
NMR (DMSO-d$_6$, δ): 2.38 (3H, s), 2.49 (3H, s), 6.70 (1H, s), 7.34 (1H, dd, 7.6, 7.6 Hz), 7.52 (1H, d, J=7.6 Hz), 7.59 (1H, d, J=7.6 Hz), 7.78 (1H, dd, J=7.8, 7.8 Hz), 7.99 (1H, d, J=7.8 Hz), 8.21 (1H, d, J==7.8 Hz), 8.38 (1H, s), 8.3–8.6 (4H, br), 11.38 (1H, s)
(+) APCI MASS: 294 (M+H)$^+$
Elemental Analysis Calcd. for C$_{17}$H$_{15}$N$_3$O$_2$.CH$_4$O$_3$S: C 55.52, H 4.92, N 10.72 Found: C 55.10, H 4.72, N 10.62
(18) [3-(Benzofuran-3-yl)benzoyl]guanidine methanesulfonate
mp: 227–228° C.
IR (Nujol): 3300, 1680, 1600, 1050, 740 cm$^{-1}$
NMR (DMSO-d$_6$, δ): 2.45 (3H, s), 7.36–7.50 (2H, m), 7.65–7.80 (2H, m), 7.95–8.13 (3H, m), 8.29 (1H, s), 8.35–8.70 (4H, m), 8.54 (1H, s), 11.48 (1H, s)
(+) APCI MASS: 280 (M+H)$^+$
Elemental Analysis Calcd. for C$_{16}$H$_{13}$N$_3$O$_2$.CH$_4$O$_3$S: C 54.39, H 4.56, N 11.19 Found: C 54.57, H 4.49, N 11.13
(19) [3-(2,3-Dihydrobenzofuran-4-yl)benzoyl]guanidine methanesulfonate
mp: 188–191° C.
IR (Nujol): 1700, 1300, 1165, 1040 cm$^{-1}$
NMR (DMSO-d$_6$, δ): 2.42 (3H, s), 3.29 (2H, t, J=8.5 Hz), 4.55 (2H, t, J=8.5 Hz), 6.85 (1H, d, J=7.8 Hz), 7.00 (1H, d, J=7.8 Hz), 7.25 (1H, dd, J=7.8, 7.8 Hz), 7.70 (1H, dd, J=7.7, 7.7 Hz), 7.88 (1H, d, J=7.7 Hz), 7.96 (1H, d, J=7.7 Hz), 8.06 (1H, s), 8.41, 8.58 (total 4H, each br s), 11.37 (1H, s)
(+) APCI MASS: 282 (M+H)$^+$
Elemental Analysis Calcd. for C$_{16}$H$_{15}$N$_3$O$_2$.CH$_4$SO$_3$: C 54.10, H 5.07, O 11.13 Found: C 53.70, H 5.22, O 11.04
(20) [5-(Benzofuran-4-yl)-3-[(2-dimethylaminoethyl)carbamoyl]benzoyl]guanidine dihydrochloride
mp: 253–255° C.
IR (Nujol): 3250, 1700, 1240, 840 cm$^{-1}$
NMR (DMSO-d$_6$, δ): 2.83 (3H, s), 2.85 (3H, s), 3.25–3.35 (2H, m), 3.70–3.75 (2H, m), 7.26 (1H, d, J=2.1 Hz), 7.48 (1H, dd, J=7.9, 7.9 Hz), 7.68 (1H, d, J=7.9 Hz), 7.71 (1H, d, J=7.9 Hz), 8.15 (1H, d, J=2.1 Hz), 8.46 (1H, s), 8.54 (1H, s), 8.62 (1H, s), 8.78 (4H, s), 9.20 (1H, t, J=5.4 Hz), 10.44 (1H, br s), 12.37 (1H, s)
(+) APCI MASS: 394 (M+H)$^+$
(21) [5-(2,5-Dichlorothiophen-3-yl)-3-[(4-methylpiperazin-1-yl)carbonyl3benzoyl]guanidine dihydrochloride
mp: 291–294° C. (dec.)
IR (Nujol): 3325, 1700, 1635, 1260, 1030 cm$^{-1}$
NMR (DMSO-d$_6$, δ): 2.51 (2H, s), 2.78 (3H, s), 2.8–3.8 (6H, br), 7.71 (1H, s), 8.01 (1H, s), 8.26 (1H, s), 8.45 (1H, s), 8.75, 8.86 (total 4H, each br s), 11.43 (1H, s), 12.52 (1H, s)
(+) APCI MASS: 440, 442 (M+H)$^+$
(22) [3-(2-Difluoromethyl-3,4-dihydro-1-naphthyl)benzoyl]guanidine methanesulfonate
mp: 177–178° C.
IR (Nujol): 3070, 1710, 1690, 1590 cm$^{-1}$
NMR (DMSO-d$_6$, δ): 2.37 (3H, s), 2.5–2.6 (2H, m), 2.9–3.0 (2H, m), 6.16 (1H, t, J=55.1 Hz), 6.54 (1H, d, J=7.6 Hz), 7.1–7.4 (3H, m), 7.57 (1H, d, J=7.7 Hz), 7.7–7.9 (2H, m), 8.07 (1H, d, J=7.9 Hz), 8.39 (4H, br s), 11.27 (1H, s)
(+) APCI MASS: 342 (M+H)$^+$
Elemental Analysis Calcd. for C$_{19}$H$_{17}$F$_2$N$_3$O.CH$_4$O$_3$S: C 54.91, H 4.84, N 9.61 Found: C 54.54, H 4.58, N 9.50
(23) [3-(2-Hydroxymethyl-3,4-dihydro-1-naphthyl)benzoyl]guanidine methanesulfonate
mp: 177–178° C.
IR (Nujol): 1700, 1645, 1610 cm$^{-1}$
NMR (DMSO-d$_6$, δ): 2.39 (3H, s), 2.4–2.6 (2H, m), 2.8–2.9 (2H, m), 3.85 (2H, s), 6.43 (1H, d, J=7.3 Hz), 7.0–7.3 (3H, m), 7.52 (1H, d, J=7.6 Hz), 7.6–7.8 (2H, m), 8.00 (1H, d, J=8.0 Hz), 8.38 (2H, br s), 8.53 (2H, br s)
(+) APCI MASS: 322 (M+H)$^+$
Elemental Analysis Calcd. for C$_{19}$H$_{19}$N$_3$O$_2$.CH$_4$O$_3$S: C 57.54, H 5.55, N 10.06 Found: C 57.69, H 5.59, N 10.03
(24) [3-(2-Hydroxyiminomethyl-3,4-dihydro-1-naphthyl)benzoyl]guanidine methanesulfonate
mp: 220–222° C.
IR (Nujol): 3300, 3150, 1710, 1690 cm$^{-1}$
NMR (DMSO-d$_6$, δ): 2.37 (3H, s), 2.7–3.0 (4H, m), 6.53 (1H, d, J=7.2 Hz), 7.0–7.3 (3H, m), 7.46 (1H, s), 7.57 (1H, d, J=7.7 Hz), 7.7–7.8 (2H, m), 8.05 (1H, d, J=8.1 Hz), 8.36 (2H, br s), 8.48 (2H, br s)
(+) APCI MASS: 335 (M+H)$^+$
Elemental Analysis Calcd. for C$_{19}$H$_{18}$N$_4$O$_2$.CH$_4$O$_3$S: C 55.80, H 5.15, N 13.01 Found: C 55.68, H 5.12, N 12.85

EXAMPLE 9

The following compound was obtained by reacting dimethyl 5-(2,5-dichlorothiophen-3-yl)isophthalate with guanidine hydrochloride according to similar manners to those of Examples 1, 2 and 3.

[3-(Diaminomethyleneaminocarbonyl)-5-(2,5-dichlorothiophen-3-yl)benzoyl]guanidine dimethanesulfonate mp: 242–243° C.

IR (Nujol): 3100, 1720, 1600, 1240, 1210 cm$^{-1}$

NMR (DMSO-d$_6$, δ): 2.45 (6H, s), 7.62 (1H, s), 8.42 (2H, s), 8.48 (2H, br s), 8.49 (1H, s), 8.63 (2H, br s), 11.63 (2H, s)

Elemental Analysis Calcd. for C$_{14}$H$_{12}$Cl$_2$N$_6$O$_2$S.2CH$_3$SO$_3$H: C 32.49, H 3.41, N 14.21 Found: C 32.36, H 3.27, N 14.00

EXAMPLE 10

The following compound was obtained by reacting dimethyl 5-(benzofuran-4-yl)isophthalate with guanidine hydrochloride according to similar manners to those of Examples 1, 2 and 3.

[5-(Diaminomethyleneaminocarbonyl)-3-(benzofuran-4-yl)benzoyl]guanidine dimethanesulfonate mp: 252–254° C.

IR (Nujol): 3325, 1720, 1205, 1050 cm$^{-1}$

NMR (DMSO-d$_6$, δ): 2.42 (6H, s), 7.30 (1H, d, J=2.1 Hz), 7.52 (1H, dd, J=7.8, 7.8 Hz), 7.63 (1H, d, J=7.8 Hz), 7.75 (1H, d, J=7.8 Hz), 8.19 (1H, d, J=2.1 Hz), 8.47 (3H, s), 8.47, 8.64 (total 8H, br s), 11.62 (2H, s)

(+) APCI MASS: 365 (M+H)$^+$

Elemental Analysis Calcd. for C$_{18}$H$_{16}$N$_6$O$_3$.C$_2$H$_8$O$_6$S$_2$: C 43.16, H 4.35, N 15.10 Found: C 42.99, H 4.12, N 14.80

EXAMPLE 11

The mixture of methyl 5-[(E)-2-carboxyethenyl]-3-(2,5-dichlorothiophen-3-yl)benzoate (0.6 g), N,N-dimethylethylenediamine (0.22 ml), 1-hydroxybenzotriazole (0.27 g) and 1-(3-dimethylaminopropyl)-3-ethylcarbodiimide hydrochloride (0.35 g) in N,N-dimethylformamide (10 ml) was stirred for 4 hours at ambient temperature. To the above mixture was added a mixture of guanidine hydrochloride (0.8 g) in N,N-dimethylformamide (10 ml) and 28 methanolic sodium methoxide (1.5 ml). The mixture was stirred for 16 hours at same temperature and the mixture was poured onto water. The mixture was extracted with the solution of ethyl acetate and tetrahydrofuran and the extracted layer was washed with brine, dried over magnesium sulfate and evaporated in vacuo. To the residue in methanol (10 ml) was added slight excess 4N-hydrogen chloride-ethyl acetate, and the isolated precipitate was collected by filtration. The precipitate was recrystallized from methanol to give [3-(2,5-dichlorothiophen-3-yl)-5-[(E)-2-[(2-dimethylaminoethyl) carbamoyl]ethenyl]benzoyl]guanidine dihydrochloride (0.44 g).

mp: 225–226° C.

IR (Nujol): 3350–3200 (br), 2660, 1705, 1668, 1625, 1593 cm$^{-1}$

NMR (DMSO-d$_6$, δ): 2.81 (6H, s), 3.15–3.30 (2H, m), 3.53–3.66 (2H, m), 6.89 (1H, d, J=15.8 Hz), 7.60 (1H, d, J=15.8 Hz), 7.70 (1H, s), 8.15 (1H, s), 8.32 (1H, s), 8.39 (1H, s), 8.60–8.73 (3H, m), 8.85 (2H, s), 10.22 (1H, s), 12.55 (1H, s)

Elemental Analysis Calcd. for C$_{19}$H$_{21}$N$_5$O$_2$S.2HCl: C 43.28, H 4.40, N 13.28 Found: C 43.04, H 4.55, N 13.11

EXAMPLE 12

The following compounds were obtained according to a similar manner to that of Example 1, 2 or 3.

(1) [5-(2-Difluoromethylbenzofuran-3-yl)-3-[(2-dimethylaminoethyl)carbamoyl]benzoyl]guanidine dihydrochloride mp: 227–231° C. (dec.)

IR (Nujol): 3350, 1700, 1640, 1550, 1260 cm$^{-1}$

NMR (DMSO-d$_6$, δ): 2.84 (6H, s), 3.25–3.40 (2H, m), 3.67–3.77 (2H, m), 7.45 (1H, dd, J=7.6, 7.6 Hz), 7.50 (1H, t, J=51.3 Hz), 7.70 (1H, dd, J=7.7, 7.6 Hz), 7.80–7.87 (2H, m), 8.34 (1H, s), 8.39 (1H, s), 8.71 (4H,s), 8.74 (1H, s), 10.27 (1H, s), 12.35 (1H, s)

(+) APCI MASS: 444 (M+H)$^+$ (2) [5-(2-Difluoromethylbenzo[b]thiophen-3-yl)-3-[(2-dimethylaminoethyl)carbamoyl]benzoyl]guanidine dihydrochloride mp: 175–190° C. (dec.)

IR (Nujol): 3350 (br), 1700, 1650, 1530, 1250 cm$^{-1}$

NMR (DMSO-d$_6$, δ): 2.83 (6H, s), 3.30–3.40 (2H, m), 3.65–3.75 (2H, m), 7.47 (1H, t, J=53.9 Hz), 7.49–7.60 (3H, m), 8.21 (1H, d, J=8 Hz), 8.27 (1H, s), 8.35 (1H, s), 8.73 (4H, br s), 8.79 (1H, s), 9.16 (1H, t, J=5.6 Hz), 10.37 (1H, s), 12.32 (1H, s)

(+) APCI MASS: 460 (M+H)$^+$ (3) [5-(2,5-Dichlorothiophen-3-yl)-3-[(4-methylpiperazin-1-yl)carbamoyl]benzoyl]guanidine dihydrochloride mp: 228–230° C.

IR (Nujol): 3400, 1710, 1680, 1550, 1260 cm$^{-1}$

NMR (DMSO-d$_6$, δ): 2.79 (3H, s), 3.20–3.50 (8H, m), 7.70 (1H, s), 8.32 (1H, s), 8.45 (1H, s), 8.54 (1H, s), 8.66 (4H, br s), 10.10 (1H, s), 10.77 (1H, s), 12.31 (1H, s)

(+) APCI MASS: 455 (M+H)$^+$, 457 (M+H)$^+$ (4) [5-(3,5-Dichlorophenyl)-3-[(2-dimethylaminoethyl) carbamoyl]benzoyl]guanidine dihydrochloride mp: 278–280° C.

IR (Nujol): 3450, 3200, 2700, 1700, 1640, 1540, 1270, 1250 cm$^{-1}$

NMR (DMSO-d$_6$, δ): 2.85 (6H, s), 3.25–3.35 (2H, m), 3.65–3.75 (2H, m), 7.69 (1H, dd, J=1.8, 1.8 Hz), 8.18 (2H, d, J=1.8 Hz), 8.52 (1H, s), 8.63 (1H, s), 8.70 (2H, br s), 8.76 (1H, s), 9.00 (2H, br s), 9.29 (1H, t, J=5.7 Hz), 10.37 (1H, br s), 12.58 (1H, s)

(+) APCI MASS: 422 (M+H)$^+$, 424 (M+H)$^+$ (5) [5-(3,5-Dichlorophenyl)-3-[(2-dimethylaminoethyl) carbamoylmethoxy]benzoyl]guanidine dihydrochloride mp: 257–259° C.

IR (Nujol): 3350, 1700, 1580, 1320, 1240 cm$^{-1}$

NMR (DMSO-d$_6$, δ): 2.79 (6H, s), 3.15–3.25 (2H, m), 3.49–3.59 (2H, m), 4.79 (2H, s), 7.67 (1H, dd, J=1.8, 1.8 Hz), 7.70 (1H, dd, J=1.8, 1.8 Hz), 7.74 (1H, dd, J=1.8, 1.8 Hz), 8.03 (2H, d, J=1.8 Hz), 8.19 (1H, dd, J=1.8, 1.8 Hz), 8.51 (1H, t, J=5.6 Hz), 8.60 (2H, br s), 8.85 (2H, br s), 10.16 (1H, br s), 12.43 (1H, s)

(+) APCI MASS: 452 (M+H)$^+$, 454 (M+H)$^+$ (6) [5-(2-Difluoromethylbenzofuran-4-yl)-3-[(2-dimethylaminoethylcarbamoylmethoxy]benzoyl] guanidine dihydrochloride mp: 131–134° C.

IR (Nujol): 3300 (br), 1690, 1650, 1560, 1240 cm$^{-1}$

NMR (DMSO-d$_6$, δ): 2.79 (6H, s), 3.17–3.23 (2H, m), 3.49–3.59 (2H, m), 4.80 (2H, s), 7.32 (1H, t, J=52.7 Hz), 7.55–7.70 (4H, m), 7.77–7.84 (2H, m), 7.99 (1H, s), 8.56 (1H, t, J=5.6 Hz), 8.59 (2H, br s), 8.79 (2H, br s), 10.18 (1H, br s), 12.29 (1H, s)

(+) APCI MASS: 474 (M+H)$^+$ (7) [5-(2,5-Dichlorothiophen-3-yl)-3-[(2-dimethylaminoethyl)carbamoylmethoxy]benzoyl] guanidine dihydrochloride mp: 192° C. (dec.)

IR (Nujol): 3200 (br), 1700, 1660, 1520, 1280 cm$^{-1}$

NMR (DMSO-d$_6$, δ): 2.78 (6H, s), 3.15–3.25 (2H, m), 3.48–3.58 (2H, m), 4.75 (2H, s), 7.60 (1H, s), 7.66 (1H, s), 7.76 (1H, s), 7.98 (1H, s), 8.54 (1H, t, J=5, 6 Hz), 8.66 (2H, br s), 8.83 (2H, br s), 10.29 (1H, br s), 12.38 (1H, s)

(+) APCI MASS: 458 (M+H)$^+$, 460 (M+H)$^+$ (8) [3-(2-Difluoromethylbenzo[b]thiophen-3-yl)benzoyl] guanidine methanesulfonate mp: 238–240° C.

IR (Nujol): 3300, 1710, 1600, 1290, 1270, 1260 cm$^{-1}$

NMR (DMSO-d$_6$, δ): 2.34 (3H, s), 7.22 (1H, t, J=53.8 Hz), 7.47–7.63 (3H, m), 7.83–7.86 (2H, m), 8.01 (1H, s), 8.09–8.14 (1H, m), 8.21 (1H, d, J=7.7 Hz), 8.39 (4H, br s), 11.28 (1H, s)

(+)APCI MASS: 346 (M+H)$^+$

Elemental Analysis Calcd. for C$_{17}$H$_{13}$F$_2$N$_3$OS.CH$_3$SO$_3$H: C 48.97, H 3.88, N 9.52 Found: C 48.76, H 3.74, N 9.25

(9) [5-(2-Chlorobenzofuran-3-yl)-3-[(2-dimethylaminoethyl)carbamoyl]benzoyl]guanidine dihydrochloride mp: 254–258° C. (dec.)

IR (Nujol): 3300, 1700, 1650, 1530 cm$^{-1}$

NMR (DMSO-d$_6$, δ): 2.85 (6H, s), 3.28–3.38 (2H, m), 3.66–3.76 (2H, m), 7.41 (1H, dd, J=7.6, 7.5 Hz), 7.49 (1H, dd, J=7.6, 7.0 Hz), 7.74 (1H, d, J=7.5 Hz), 7.83 (1H, d, J=7.0 Hz), 8.44 (1H, s), 8.50 (1H, s), 8.70 (4H, s), 8.77 (1H, s), 9.13 (1H, t, J=5.5 Hz), 10.19 (1H, br s), 12.28 (1H, s)

(+) APCI MASS: 428 (M+H)$^+$, 430 (M+H)$^+$

(10) [5-(2-Difluoromethylthiophen-3-yl)-3-[(2-dimethylaminoethyl)carbamoyl]benzoyl]guanidine dihydrochloride mp: 148–158° C.

IR (Nujol): 3250 (br), 1700, 1650, 1530, 1250 cm$^{-1}$

NMR (DMSO-d$_6$, δ): 2.84 (6H, s), 3.32–3.42 (2H, m), 3.60–3.70 (2H, m), 7.47 (1H, t, J=54.2 Hz), 7.56 (1H, d, J=5.1 Hz), 7.97 (1H, d, J=5.1 Hz), 8.27 (1H, s), 8.36 (1H, s), 8.61 (1H, s), 8.68 (4H, s), 9.15 (1H, t, J=5.5 Hz), 10.15 (1H, s), 12.30 (1H, s)

(+) APCI MASS: 410 (M+H)$^+$

(11) [5-(2-Difluoromethylfuran-3-yl)-3-[(2-dimethylaminoethyl)carbamoyl]benzoyl]guanidine dihydrochloride mp: 144–147° C.

IR (Nujol): 3400 (br), 1700, 1650, 1570, 1530, 1250 cm$^{-1}$

NMR (DMSO-d$_6$, δ): 2.85 (6H, s), 3.25–3.35 (2H, m), 3.63–3.73 (2H, m), 7.27 (1H, d, J=1.7 Hz), 7.44 (1H, t, J=51.5 Hz), 8.05 (1H, d, J=1.7 Hz), 8.30 (1H, s), 8.40 (1H, s), 8.57 (1H, s), 8.72 (4H, br s), 9.20 (1H, t, J=5.5 Hz), 10.22 (1H, br s), 12.38 (1H, s)

(+) APCI MASS: 394 (M+H)$^+$

(12) [5-(2-Difluoromethylfuran-3-yl)-3-[(4-methylpiperazin-1-yl)carbamoyl]benzoyl]guanidine dihydrochloride mp: 225° C.

IR (Nujol): 3400, 1700, 1660, 1540, 1250 cm$^{-1}$

NMR (DMSO-d$_6$, δ): 2.79 (3H, s), 3.15–3.50 (8H, m), 7.24 (1H, d, J=1.7 Hz), 7.39 (1H, t, J=51.5 Hz), 8.04 (1H, d, J=1.7 Hz), 8.15 (1H, s), 8.40 (1H, s), 8.51 (1H, s), 8.77 (4H, s), 10.18 (1H, s), 10.89 (1H, br s), 12.50 (1H, s)

(+) APCI MASS: 421 (M+H)$^+$

(13) [3-[(2-Diethylaminoethyl)carbamoyl]-5-(2-difluoromethylfuran-3-yl)benzoyl]guanidine dihydrochloride mp: 135–137° C.

IR (Nujol): 3300 (br), 1700, 1570, 1250 cm$^{-1}$

NMR (DMSO-d$_6$, δ): 1.25 (6H, t, J=7.2 Hz), 3.15–3.35 (6H, m), 3.67–3.77 (2H, m), 7.28 (1H, d, J=1.7 Hz), 7.46 (1H, t, J=51.6 Hz), 8.04 (1H, d, J=1.7 Hz), 8.30 (1H, s), 8.42 (1H, s), 8.56 (1H, s), 8.74 (4H, br s), 9.30 (1H, t, J=5.5 Hz), 10.34 (1H, s), 12.42 (1H, s)

(+) APCI MASS: 422 (M+H)$^+$

(14) 5-(2-Difluoromethylbenzofuran-3-yl)-3-[(2-diethylaminoethyl)carbamoyl)benzoyl]guanidine dihydrochloride mp: 248–250° C.

IR (Nujol): 3200, 1700, 1670, 1570, 1210 cm$^{-1}$

NMR (DMSO-d$_6$, δ): 1.25 (6H, t, J=7.1 Hz), 3.18–3.36 (6H, m), 3.67–3.77 (2H, m), 7.45 (1H, dd, J=7.5, 7.5 Hz), 7.52 (1H, t, J=51.2 Hz), 7.60 (1H, dd, J=7.5, 7.5 Hz), 7.82–7.87 (2H, m), 8.35 (1H, s), 8.41 (1H, s), 8.73 (1H, s), 8.75 (4H, s), 9.26 (1H, t, J=5.5 Hz), 10.42 (1H, s), 12.38 (1H, s)

(+) APCI MASS: 472 (M+H)$^+$

(15) [5-(2-Difluoromethylbenzofuran-3-yl)-3-[(2-hydroxy-1-hydroxymethylethyl)carbamoyl]benzoyl]guanidine hydrochloride mp: 197–200° C.

IR (Nujol): 3300, 3150, 1710, 1630, 1540, 1250 cm$^{-1}$

NMR (DMSO-d$_6$, δ): 3.56 (4H, dd, J=5.8, 8.0 Hz), 3.93–4.13 (1H, m), 7.42 (1H, t, J=51.3 Hz), 7.45 (1H, dd, J=7.5, 7.5 Hz), 7.60 (1H, dd, J=7.5, 7.5 Hz), 7.77 (1H, d, J=7.5 Hz), 7.85 (1H, d, J=7.5 Hz), 8.30 (1H, s), 8.33 (1H, s), 8.40 (1H, d, J=8.0 Hz), 8.62 (4H, s), 8.71 (1H, s), 12.12 (1H, s)

(+) APCI MASS: 447 (M+H)$^+$

(16) [5-(2-Difluoromethylbenzofuran-3-yl)-3-[(3-dimethylaminopropyl)carbamoyl]benzoyl]guanidine dihydrochloride mp: 274–276° C. (dec.)

IR (Nujol): 3250 (br), 1700, 1620, 1250 cm$^{-1}$

NMR (DMSO-d$_6$, δ): 1.90–2.05 (2H, m), 2.76 (6H, s), 3.10–3.25 (2H, m), 3.30–3.45 (2H, m), 7.45 (1H, t, J=51.3 Hz), 7.45 (1H, dd, J=7.8, 7.8 Hz), 7.60 (1H, dd, J=7.8, 7.8 Hz), 7.80 (1H, d, J=7.8 Hz), 7.85 (1H, d, J=7.8 Hz), 8.29 (1H, s), 8.34 (1H, s), 8.72 (4H, s), 8.76 (1H, s), 8.98 (1H, t, J=5.6 Hz), 10.22 (1H, s), 12.40 (1H, s)

(+) APCI MASS: 458 (M+H)$^+$

(17) [5-(2-Difluoromethylbenzofuran-3-yl)-3-[(4-methylpiperazin-1-yl)carbamoyl]benzoyl]guanidine dihydrochloride mp: 230° C. (dec.)

IR (Nujol): 3350, 1700, 1670, 1250, 1210 cm$^{-1}$

NMR (DMSO-d$_6$, δ): 2.78 (3H, s), 3.17–3.37 (4H, m), 3.42–3.52 (4H, m), 7.46 (1H, t, J=51.2 Hz), 7.46 (1H, dd, J=7.5, 7.5 Hz), 7.60 (1H, dd, J=7.5, 7.5 Hz), 7.80 (1H, d, J=7.5 Hz), 7.84 (1H, d, J=7.5 Hz), 8.24 (1H, s), 8.36 (1H, s), 8.67 (1H, s), 8.73 (4H, s), 10.14 (1H, s), 10.81 (1H, s), 12.41 (1H, s)

(+) APCI MASS: 471 (M+H)$^+$

(18) [5-(2-Difluoromethylbenzofuran-4-yl)-3-[(2-dimethylaminoethyl)carbamoyl]benzoyl]guanidine dihydrochloride mp: 186–188° C.

IR (Nujol): 3250 (br), 1700, 1645 cm$^{-1}$

NMR (DMSO-d$_6$, δ): 2.84 (3H, s), 2.85 (3H, s), 3.28–3.40 (2H, m), 3.66–3.76 (2H, m), 7.32 (1H, t, J=52.6 Hz), 7.63 (1H, dd, J=8.0, 8.0 Hz), 7.72–7.74 (1H, m), 7.78 (1H, d, J=8.0 Hz), 7.83 (1H, d, J=8.0 Hz), 8.46 (1H, s), 8.54 (1H, s), 8.64 (1H, s), 8.73 (4H, s), 9.18 (1H, t, J=5.5 Hz), 10.29 (1H, br s), 12.34 (1H, s)

(+) APCI MASS: 444 (M+H)$^+$

Elemental Analysis Calcd. for C$_{22}$H$_{23}$N$_5$O$_3$F$_2$.2HCl: C 51.17, H 4.88, N 13.56 Found: C 51.33, H 4.95, N 13.40

(19) [5-(3,5-Dichlorophenyl)-3-[(4-methylpiperazin-1-yl)carbamoyl]benzoyl]guanidine dihydrochloride
mp: >300° C.
IR (Nujol): 1710, 1665, 1370, 1240, 855 cm⁻¹
NMR (DMSO-d$_6$, δ): 2.79 (3H, s), 3.1–3.6 (8H, m), 7.71 (1H, s), 8.10 (2H, s), 8.42 (1H, s), 8.45 (1H, s), 8.71 (1H, s), 8.5–9.0 (4H, m), 10.21 (1H, s), 10.75 (1H, br s), 12.53 (1H, s)
(+) APCI MASS: 449 (M+H)⁺, 451 (M+H)⁺

(20) [5-(2,5-Dichlorothiophen-3-yl)-3-[(3-diethylaminopropyl)carbamoyl]benzoyl]guanidine dihydrochloride
mp: 242–244° C.
IR (Nujol): 1720, 1640, 1250, 1035, 820 m⁻¹
NMR (DMSO-d$_6$, δ): 1.21 (6H, t, J=7.2 Hz), 1.8–2.1 (2H, m), 3.0–3.25 (6H, m), 3.3–3.55 (2H, m), 7.73 (1H, s), 8.40 (1H, s), 8.46 (1H, s), 8.64 (1H, s), 8.72 (4H, s), 8.98 (1H, m), 10.20 (1H, br s), 12.41 (1H, s)
APCI MASS: 470 (M+H)⁺, 472 (M+H)⁺
Elemental Analysis Calcd. for $C_{20}H_{25}Cl_2N_5O_2S\cdot 2HCl$: C 44.21, H 5.01, N 12.89 Found: C 43.91, H 5.03, N 12.64

(21) [5-(2,5-Dichlorothiophen-3-yl)-3-[(3-dimethylaminopropyl)carbamoyl]benzoyl]guanidine dihydrochloride
mp: 186–189° C.
IR (Nujol): 3250, 1690, 1645, 1305, 1035 cm⁻¹
NMR (DMSO-d$_6$, δ): 1.85–2.10 (2H, m), 2.75 (3H, s), 2.76 (3H, s), 3.05–3.25 (2H, m), 3.2–3.5 (2H, m), 7.72 (1H, s), 8.39 (1H, s), 8.46 (1H, s), 8.65 (1H, s), 8.74 (4H, s), 8.97 (1H, m), 10.36 (1H, br), 12.44 (1H, s)
(+) APCI MASS: 442 (M+H)⁺, 444 (M+H)⁺

(22) [5-(2,5-Dichlorothiophen-3-yl)-3-[(2-diethylaminoethyl)carbamoyl]benzoyl]guanidine dihydrochloride
mp: 201–203° C. (dec.)
IR (Nujol): 1705, 1640, 1250, 1210, 1035, 830, 740 cm⁻¹
NMR (DMSO-d$_6$, δ): 1.24 (6H, t, J=7.2 Hz), 3.1–3.4 (6H, m), 3.6–3.8 (2H, m), 7.74 (1H, s), 8.45 (1H, s), 8.49 (1H, s), 8.61 (1H, s), 8.5–8.8 (4H, s), 9.19 (1H, m), 10.1 (1H, br), 12.29 (1H, s)
(+) APCI MASS: 456 (M+H)⁺, 458 (M+H)⁺

(23) [5-(2,5-Dichlorothiophen-3-yl)-3-[(2-pyrrolidinoethyl)carbamoyl]benzyl]guanidine benzoyl]guanidine dihydrochloride
mp: 162–165° C.
IR (Nujol): 3350 (br), 1700, 1650, 1250 cm⁻¹
NMR (DMSO-d$_6$, δ): 1.85–2.10 (4H, m), 2.98–3.18 (2H, m), 3.30–3.40 (2H, m), 3.60–3.80 (4H, m), 7.78 (1H, s), 8.47 (1H, s), 8.51 (1H, s), 8.63 (1H, s), 8.72 (4H, s), 9.19 (1H, t, J=5.5 Hz), 10.51 (1H, s), 12.35 (1H, s)

(24) [5-(2-Difluoromethylthiophen-3-yl)-3-[(4-methylpiperazin-1-yl)carbamoyl]benzoyl]guanidine dihydrochloride
mp: 210° C. (dec.)
IR (Nujol): 3400, 1700, 1650, 1540, 1240 cm⁻¹
NMR (DMSO-d$_6$, δ): 2.79 (3H, s), 3.15–3.45 (8H, m), 7.42 (1H, t, J=54.0 Hz), 7.54 (1H, d, J=5.1 Hz), 7.97 (1H, d, J=5.1 Hz), 8.14 (1H, s), 8.34 (1H, s), 8.55 (1H, s), 8.71 (4H, s), 10.13 (1H, s), 10.73 (1H, s), 12.37 (1H, s)
(+) APCI MASS: 437 (M+H)⁺

(25) [5-(2,5-Dichlorothiophen-3-yl)-3-[(2-piperidinoethyl)carbamoyl]benzoyl]guanidine dihydrochloride
mp: 197–199° C.
IR (Nujol): 1710, 1655, 1035 cm⁻¹
NMR (DMSO-d$_6$, δ): 1.3–1.5 (1H, br), 1.6–2.0 (5H, m), 2.8–3.1 (2H, m), 3.2–3.4 (2H, m), 3.5–3.65 (2H, m), 3.65–3.8 (2H, m), 7.78 (1H, s), 8.48 (1H, s), 8.52 (1H, s), 8.62 (1H, s), 8.75 (4H, m), 9.25 (1H, m), 10.32 (1H, br), 12.39 (1H, s)
(+) APCI MASS: 468 (M+H)⁺, 470 (M+H)⁺

We claim:
1. A compound of the formula:

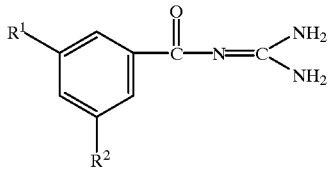

wherein
$R^1$ is hydrogen, hydroxy(lower)alkyl, protected hydroxy(lower)alkyl, acyloxy(lower)alkyl; (di(lower)alkylamino(lower)alkyl)carbamoyl(lower)alkoxy; (di(lower)alkylamino(lower)alkyl)carbamoyl(lower)alkenyl; carbamoyl which may have diamino(lower)alkylidene, di(lower)alkylamino(lower)alkyl, heterocyclic(lower)alkyl, dihydroxy(lower)alkyl or lower alkylpiperazinyl; or heterocycliccarbonyl which may have lower alkyl; and $R^2$ is ar(lower)alkenyl; aryl substituted with two suitable substituents; indenyl, indanyl, dihydrobenzocycloheptenyl, di(or tetra or hexa or octa or deca)hydronaphthyl, cyclopentenyl, dihydrothienyl, dihydrofuryl or heterobicyclic group, each of which may have suitable substituent(s);

lower alkylthienyl; mono(or di)halothienyl; mono(or di or tri)halo(lower)alkylthienyl; acylthienyl; halofuryl; or mono(or di or tri)halo(lower)alkylfuryl;

and a pharmaceutically acceptable salt thereof.

2. A compound of claim 1, wherein
$R^1$ is hydrogen; hydroxy(lower)alkyl; acyloxy(lower)alkyl; [di(lower)alkylamino(lower)alkyl]carbamoyl(lower)alkoxy; [di(lower)alkylamino(lower)alkyl]carbamoyl(lower)alkenyl; carbamoyl which may have diamino(lower)alkylidene, di(lower)alkylamino(lower)alkyl, heterocyclic(lower)alkyl, dihydroxy(lower)alkyl or lower alkylpiperazinyl; or heterocycliccarbonyl which may have lower alkyl; and $R^2$ is phenyl(lower)alkenyl; phenyl substituted with two substituents selected from the group consisting of halogen, lower alkoxy, hydroxy, lower alkyl and mono (or di or tri)halo(lower)alkyl; indenyl, indanyl, dihydrobenzocycloheptenyl, di(or tetra or hexa or octa or deca)hydronaphthyl, cyclopentenyl, dihydrothienyl, dihydrofuryl, benzofuryl, dihydrobenzofuryl, benzopyranyl, lower alkylenedioxyphenyl, quinolyl, isoquinolyl, quinoxalinyl, benzoxazolyl, imidazopyridyl, benzothienyl or indolyl, each of which may have 1 to 3 substituent(s) selected from the group consisting of oxo, hydroxyimino(lower)alkyl, protected hydroxyimino(lower)alkyl, hydroxy(lower)alkyl, protected hydroxy(lower)alkyl, mono(or di or tri)halo(lower)alkyl, halogen, lower alkylene, lower alkyl, lower alkoxy(lower)alkyl and cyano; lower alkylthienyl; mono(or di)halothienyl; [dihalo(lower)alkyl]thienyl; lower alkanoylthienyl; sulfamoylthienyl; halofuryl; or [dihalo(lower)alkyl]furyl.

3. A compound of claim 2, wherein
$R^1$ is hydrogen; hydroxy(lower)alkyl; acyloxy(lower)alkyl; [di(lower)alkylamino(lower)alkyl]carbamoyl(lower)alkoxy; [di(lower)alkylamino(lower)alkyl]carbamoyl(lower)alkenyl; carbamoyl which may have diamino(lower)alkylidene, di(lower)alkylamino(lower) alkyl, morpholinyl(lower)alkyl, pyrrolidinyl (lower)alkyl, piperidyl(lower)alkyl, dihydroxy(lower)
alkyl or lower alkylpiperazinyl; or piperazinylcarbonyl
which may have lower alkyl, and $R^2$ is phenyl(lower)alkenyl; phenyl substituted with two substituents selected from the group consisting of halogen, lower alkoxy, hydroxy, lower alkyl and mono (or di or tri)halo(lower)alkyl; indenyl, indanyl, dihydrobenzocycloheptenyl, di(or tetra or hexa or octa or deca)hydronaphthyl, cyclopentenyl, dihydrothienyl, dihydrofuryl, benzofuryl, dihydrobenzofuryl, benzopyranyl, lower alkylenedioxyphenyl, quinolyl, isoquinolyl, quinoxalinyl, benzoxazolyl, imidazopyridyl, benzothienyl or indolyl, each of which may have one or two substituent(s) selected from the group consisting of oxo, hydroxyimino(lower)alkyl, acyloxyimino(lower)alkyl, hydroxy(lower)alkyl, acyloxy(lower)alkyl, mono(or di or tri)halo(lower) alkyl, halogen, lower alkylene, lower alkyl, lower alkoxy(lower)alkyl and cyano; lower alkylthienyl; mono(or di)halothienyl; [dihalo(lower)alkyl]thienyl; lower alkanoylthienyl; sulfamoylthienyl; halofuryl; or [dihalo(lower)alkyl]furyl.

4. A compound of claim 3, wherein $R^1$ is hydrogen; hydroxy(lower)alkyl; acyloxy(lower)alkyl; [di(lower)alkylamino(lower)alkyl]carbamoyl (lower)alkoxy; [di(lower)alkylamino(lower)alkyl] carbamoyl(lower)alkenyl; diamino(lower) alkylidenecarbamoyl; [di(lower)alkylamino(lower) alkyl]carbamoyl; [morpholinyl(lower)alkyl] carbamoyl; [pyrrolidinyl(lower)alkyl]carbamoyl; [piperidyl(lower)alkyl]carbamoyl; [dihydroxy(lower) alkyl]carbamoyl; [lower alkylpiperazinyl]carbamoyl; or lower alkylpiperazinylcarbonyl; and $R^2$ is phenyl(lower)alkenyl; dihalophenyl; di(lower) alkoxyphenyl; dihydroxyphenyl; di(lower)alkylphenyl; bis(trihalo(lower)alkyl)phenyl; indenyl; indanyl which may have oxo; dihydrobenzocycloheptenyl; dihydronaphthyl which may have hydroxyimino(lower) alkyl, hydroxy(lower)alkyl, dihalo(lower)alkyl or lower alkoxy(lower)alkyl; octahydronaphthyl; cyclopentenyl which may have cyano; dihydrothienyl which may have cyano; dihydrofuryl which may have cyano; benzofuryl which may have lower alkyl, halogen or dihalo(lower)alkyl; dihydrobenzofuryl; benzopyranyl which may have one or two substituent(s) selected from the group consisting of lower alkyl, lower alkylene and halogen; methylenedioxyphenyl; quinolyl; isoquinolyl; quinoxalinyl; benzoxazolyl; imidazopyridyl which may have lower alkyl; benzothienyl which may have halogen or dihalo(lower)alkyl; indolyl which may have lower alkyl; lower alkylthienyl; mono(or di)halothienyl; [dihalo(lower)alkyl]thienyl; lower alkanoylthienyl; sulfamoylthienyl; halofuryl; or [dihalo(lower)alkyl]furyl.

5. A compound of claim 4, wherein $R^2$ is phenyl(lower)alkenyl, dihalophenyl, di(lower) alkoxyphenyl, dihydroxyphenyl, di(lower) alkylphenyl, bis(trihalo(lower)alkyl)phenyl, indenyl, oxoindanyl, dihydrobenzocycloheptenyl, dihydronaphthyl, [hydroxyimino(lower)alkyl] dihydronaphthyl, [hydroxy(lower)alkyl] dihydronaphthyl, [dihalo(lower)alkyl] dihydronaphthyl, [lower alkoxy(lower)alkyl] dihydronaphthyl, octahydronaphthyl, cyanocyclopentenyl, cyanodihydrothienyl, cyanodihydrofuryl, benzofuryl, lower alkylbenzofuryl, halobenzofuryl, [dihalo(lower) alkyl]benzofuryl, dihydrobenzofuryl, benzopyranyl, di(lower) alkylbenzopyranyl, lower alkylenebenzopyranyl, halobenzopyranyl, methylenedioxyphenyl, quinolyl, isoquinolyl, quinoxalinyl, benzoxazolyl, lower alkylimidazopyridyl, benzothienyl, halobenzothienyl, dihalo(lower)alkylbenzothienyl, indolyl, lower alkylindolyl, lower alkylthienyl, mono(or di)halothienyl, [dihalo(lower)alkyl]thienyl, lower alkanoylthienyl, sulfamoylthienyl, halofuryl, or [dihalo(lower)alkyl]furyl.

6. A compound of claim 5, wherein $R^1$ is [pyrrolidinyl(lower)alkyl]carbamoyl, [piperidyl(lower)alkyl]carbamoyl, [di(lower)alkylamino(lower)alkyl]carbamoyl, and $R^2$ is dihalothienyl.

7. A compound of claim 5, wherein $R^1$ is [di(lower)alkylamino(lower)alkyl]carbamoyl or [lower alkylpiperazinyl]carbamoyl, and $R^2$ is [dihalo(lower)alkyl]thienyl.

8. A process for preparing a compound of the formula:

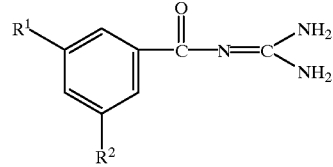

wherein $R^1$ is hydrogen, hydroxy(lower)alkyl, protected hydroxy(lower)alkyl, acyl(lower)alkoxy, acyl(lower)alkenyl, or acyl, and $R^2$ is ar(lower)alkenyl; aryl substituted with two suitable substituents; indenyl, indanyl, dihydrobenzocycloheptenyl, di(or tetra or hexa or octa or deca)hydronaphthyl, cyclopentenyl, dihydrothienyl, dihydrofuryl or heterobicyclic group, each of which may have suitable substituent s); lower alkylthienyl; mono(or di)halothienyl; mono(or di or tri)halo(lower)alkylthienyl; acylthienyl; halofuryl; or mono(or di or tri)halo(lower)alkylfuryl;

or a salt thereof which comprises reacting a compound of the formula:

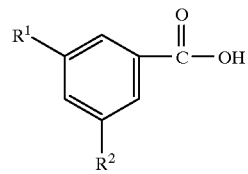

wherein $R^1$ and $R^2$ are each as defined above, or its reactive derivative at the carboxy group, or a salt thereof with a compound of the formula:

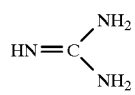

or its reactive derivative at the imino group, or a salt thereof.

9. A pharmaceutical composition which comprises, as an active ingredient, a compound of claim 1 or a pharmaceutically acceptable salt thereof in admixture with pharmaceutically acceptable carriers.

10. A use of a compound of claim 1 or a pharmaceutically acceptable salt thereof as an inhibitor on $Na^+/H^+$ exchange in cells.

11. A method for the prophylactic or therapeutic treatment of cardiovascular diseases, cerebrovascular diseases, renal diseases, arteriosclerosis or shock which comprises administering a compound of claim 1 or a pharmaceutically acceptable salt thereof to human or animals.

12. A process for preparing a pharmaceutical composition which comprises admixing a compound of claim 1 or a pharmaceutically acceptable salt thereof with a pharmaceutically acceptable carrier.

* * * * *